US012331107B2

(12) United States Patent
Neil et al.

(10) Patent No.: US 12,331,107 B2
(45) Date of Patent: *Jun. 17, 2025

(54) METHODS OF TREATING PNEUMONIA OR RESPIRATORY FAILURE ASSOCIATED WITH COVID-19 BY ADMINISTERING AN ANTI-LIGHT ANTIBODY

(71) Applicant: Avalo Therapeutics, Inc., Rockville, MD (US)

(72) Inventors: Garry A. Neil, Havertown, PA (US); Inbal Zafir-Lavie, Misgav (IL)

(73) Assignee: Avalo Therapeutics, Inc., Rockville, MD (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/329,069

(22) Filed: Jun. 5, 2023

(65) Prior Publication Data
US 2024/0002492 A1    Jan. 4, 2024

Related U.S. Application Data

(63) Continuation of application No. 17/218,449, filed on Mar. 31, 2021, now Pat. No. 11,708,406.

(60) Provisional application No. 63/133,636, filed on Jan. 4, 2021, provisional application No. 63/027,127, filed on May 19, 2020, provisional application No. 63/003,826, filed on Apr. 1, 2020.

(51) Int. Cl.
| C07K 16/24 | (2006.01) |
| A61K 31/706 | (2006.01) |
| A61K 39/00 | (2006.01) |
| A61K 39/395 | (2006.01) |
| A61K 45/06 | (2006.01) |
| A61P 1/00 | (2006.01) |
| A61P 29/00 | (2006.01) |
| A61P 31/14 | (2006.01) |
| G01N 33/68 | (2006.01) |

(52) U.S. Cl.
CPC .......... C07K 16/241 (2013.01); A61K 31/706 (2013.01); A61K 39/3955 (2013.01); A61K 45/06 (2013.01); A61P 1/00 (2018.01); A61P 29/00 (2018.01); A61P 31/14 (2018.01); G01N 33/6863 (2013.01); A61K 2039/505 (2013.01); C07K 2317/565 (2013.01); C07K 2317/90 (2013.01); G01N 2333/525 (2013.01)

(58) Field of Classification Search
CPC ............ C07K 16/241; C07K 2317/565; A61K 39/3955; A61K 2039/505; A61P 29/00
See application file for complete search history.

(56) References Cited

U.S. PATENT DOCUMENTS

| 6,998,108 | B1 | 2/2006 | Ware |
| 7,575,745 | B2 | 8/2009 | Ware |
| 8,058,402 | B2 | 11/2011 | Granger et al. |
| 8,153,123 | B2 | 4/2012 | Ware et al. |
| 8,263,081 | B2 | 9/2012 | Fu |
| 8,349,320 | B2 | 1/2013 | Ware et al. |
| 8,461,307 | B2 | 6/2013 | Granger et al. |
| 8,524,869 | B2 | 9/2013 | Smith et al. |
| 8,974,787 | B2 | 3/2015 | Granger et al. |
| 9,301,994 | B2 | 4/2016 | Croft et al. |
| 9,623,116 | B2 | 4/2017 | Fu |
| 9,700,606 | B2 | 7/2017 | Ware et al. |
| 10,407,725 | B2 | 9/2019 | Hakonarson et al. |
| 10,525,130 | B2 | 1/2020 | Schnieders et al. |
| 11,242,564 | B2 | 2/2022 | Galon et al. |
| 2013/0315913 | A1 | 11/2013 | Zhang |
| 2013/0323240 | A1 | 12/2013 | Smith et al. |
| 2014/0004106 | A1 | 1/2014 | Schnieders et al. |
| 2015/0056182 | A1 | 2/2015 | Igawa et al. |
| 2015/0307620 | A1 | 10/2015 | Vella et al. |
| 2015/0337046 | A1 | 11/2015 | Granger et al. |
| 2017/0051352 | A1 | 2/2017 | Hakonarson et al. |
| 2019/0315876 | A1 | 10/2019 | Holmes |

FOREIGN PATENT DOCUMENTS

| EP | 1274840 B1 | 6/2007 |
| EP | 1674575 B1 | 10/2010 |
| EP | 1003782 B1 | 1/2011 |
| EP | 2207597 B1 | 2/2020 |
| WO | 2008027338 A3 | 7/2008 |
| WO | 2015107331 A3 | 10/2015 |

OTHER PUBLICATIONS

Steinberg, M. W., et al., "Regulating the mucosal immune system: the contrasting roles of LIGHT, HVEM, and their various partners" Seminars in immunopathology 31, 207-221 (2009).
Veauthier and Hornecker, "Crohn's Disease: Diagnosis and Management" Am. Fam. Physician, 98(11):661-669 (2018).

(Continued)

Primary Examiner — Robert S Landsman
(74) Attorney, Agent, or Firm — McNeill PLLC

(57) ABSTRACT

The present disclosure relates to methods of detecting free (active) LIGHT in biological samples to diagnose conditions associated with elevated free LIGHT, as well as to predict the effectiveness of anti-LIGHT therapies. The disclosure also relates to treating such conditions with anti-LIGHT antibodies. Conditions include acute lung injury (ALI) and acute respiratory distress syndrome (ARDS), optionally wherein the ALI and ARDS are associated with viral infection, including coronavirus infection. Conditions also include Crohn's Disease or an inflammatory condition associated with Crohn's Disease.

8 Claims, 13 Drawing Sheets
Specification includes a Sequence Listing.

(56) References Cited

OTHER PUBLICATIONS

Vincent JL, et al. "The SOFA (Sepsis-related Organ Failure Assessment) score to describe organ dysfunction/failure. On behalf of the Working Group on Sepsis-Related Problems of the European Society of Intensive Care Medicine" Intensive Care Med., 22(7):707-710 (1996).
Wang et al., "The critical role of LIGHT in promoting intestinal inflammation and Crohn's disease" J. Immunol., 174;8173-82 (2005).
Wang, D. et al., "Clinical Characteristics of 138 Hospitalized Patients With 2019 Novel Coronavirus-Infected Pneumonia in Wuhan, China" JAMA, 323(11):1061-1069 (2020).
Ware, C. F. "Targeting the LIGHT-HVEM pathway" Therapeutic Targets of the TNF Superfamily, 146-155 (2009).
Ware, C.F. "Targeting lymphocyte activation through the lymphotoxin and LIGHT pathways" Immunological reviews 223, 186-201 (2008).
Ware, C.F., "Network Communications: Lymphotoxins, LIGHT and TNF" Annual Rev. Immunol., 23:787-819 (2005).
Ware, Carl F. et al., "Realigning the LIGHT signaling network to control dysregulated inflammation", Journal of Experimental Medicine, 2022, vol. 219, No. 7.
Wroblewski, V. J. et al. "Decoy receptor 3 (DcR3) is proteolytically processed to a metabolic fragment having differential activities against Fas ligand and LIGHT" Biochemical pharmacology 65, 657-667 (2003).
Wu, F. et al. "A new coronavirus associated with human respiratory disease in China" Nature 579, 265-269 (2020).
Xiao, F. et al. "Evidence for Gastrointestinal Infection of SARS-CoV-2" Gastroenterology, 158(6):1831-1833 (2020).
Xu et al., "Transcriptome Sequencing Identifies Novel Immune Response Genes Highly Related to the Severity of Human Adenovirus Type 55 Infection" Front Microbiol 6(10):130 (2019).
Xu, Z. et al. "Pathological findings of COVID-19 associated with acute respiratory distress syndrome" The Lancet. Respiratory medicine, (4):420-422 (2020).
Yu et al., "A newly identified member of tumor necrosis factor receptor superfamily (TR6) suppresses LIGHT-mediated apoptosis" J. Biol. Chem., 274(20):13733-6 (1999).
Cerecor Press Release on Feb. 3, 2020, retrieved from internet at https://ir.cerecor.com/press-releases/detail/87/cerecor-and-aevigenomic-medicine-complete-merger, on Jul. 7, 2021.
Cerecor Press Release on Mar. 11, 2020, retrieved from internet at https://ir.cerecor.com/press-releases/detail/89/cerecor-reports-2019-results, on Jul. 7, 2021.
Cerecor Press Release on Mar. 26, 2020, retrieve from internet at: https://ir.cerecor.com/press-releases/detail/90/cerecor-announces-exploration-of-the-role-of-an, on Jul. 7, 2021.
Chan, JF, et al., "A familial cluster of pneumonia associated with the 2019 novel coronavirus indicating person-to-person transmission: a study of a family cluster" Lancet, 395(10223):514-523 (2020).
Channappanavar, R. & Perlman, S. "Pathogenic human coronavirus infections: causes and consequences of cytokine storm and immunopathology" Seminars in Immunopathology 39, 529-539, (2017).
Channappanavar, R. et al. "Dysregulated Type I Interferon and Inflammatory Monocyte-Macrophage Responses Cause Lethal Pneumonia in SARS-CoV-Infected Mice" Cell Host & Microbe 19, 181-193 (2016).
Clinical Trials, History of Changes for Study: NCT03169894; Evaluation of the Safety, Tolerability, and Efficacy of MDGN-002 in Adults With Moderate to Severe Active Crohn's Disease, May 25, 2017; retrieved from internet at https://clinicaltrials.gov/ct2/history/NCT03169894?A=1&B=1&C=merged#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease, Sep. 25, 2017; retrieved from internet at https://clinicaltrials.gov/ct2/history/NCT03169894?V_5=View#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease, Jun. 1, 2018; retrieved from internet at https://clinicaltrials.gov/ct2/history/NCT03169894?V_7=View#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease, Nov. 6, 2018; retrieved from internet at https://clinicaltrials.gov/ct2/history/NCT03169894?V_9=View#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease, Mar. 7, 2019; retrieved from internet at https://clinicaltrials.gov/ct2/history/NCT03169894?V_11=View#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease, Jul. 2, 2021; retrieved from internet at https://clinicaltrials.gov/ct2/history/NCT03169894?V_12=View#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease, Dec. 17, 2021; retrieved from internet at https://clinicaltrials.gov/ct2/history/NCT03169894?V_13=View#StudyPageTop on Jan. 12, 2022.
Clinical Trials, History of Changes for Study: NCT03169894; Evaluation of the Safety, Tolerability, and Efficacy of MDGN-002 in Adults With Moderate to Severe Active Crohn's Disease or Ulcerative Colitis, Jan. 19, 2022; retrieved from internet at https://clinicaltrials.gov/ct2/history/NCT03169894?V_14=View#StudyPageTop on Oct. 27, 2022.
Clinical Trials, History of Changes for Study: NCT03169894; Evaluation of the Safety, Tolerability, and Efficacy of MDGN-002 in Adults With Moderate to Severe Active Crohn's Disease or Ulcerative Colitis, Feb. 24, 2022; retrieved from internet at https://clinicaltrials.gov/ct2/history/NCT03169894?V_15=View#StudyPageTop on Oct. 27, 2022.
Clinical Trials, History of Changes for Study: NCT04412057; Clinical Trial to Evaluate CERC-002 in Adults with COVID-19 Pneumonia and Acute Lung Injury, May 29, 2020; retrieved from internet at https://clinicaltrials.gov/ct2/history/NCT04412057?V_1=View#StudyPageTop on Jan. 12, 2022.
Clinical Trials, History of Changes for Study: NCT04412057; Clinical Trial to Evaluate CERC-002 in Adults with COVID-19 Pneumonia and Acute Lung Injury, Mar. 1, 2021; retrieved from internet at https://clinicaltrials.gov/ct2/history/NCT04412057?V_7=View#StudyPageTop on Jan. 12, 2022.
Clinical Trials, History of Changes for Study: NCT04412057; Clinical Trial to Evaluate CERC-002 in Adults with COVID-19 Pneumonia and Acute Lung Injury, Feb. 24, 2022; retrieved from internet at https://clinicaltrials.gov/ct2/history/NCT04412057?V_8=View#StudyPageTop on Oct. 27, 2022.
Clinical Trials, History of Changes for Study: NCT04412057; Clinical Trial to Evaluate CERC-002 in Adults with COVID-19 Pneumonia and Acute Lung Injury, Mar. 22, 2022; retrieved from internet at https://clinicaltrials.gov/ct2/history/NCT04412057?V_9-View#StudyPageTop on Oct. 27, 2022.
Cohavy et al., "LIGHT expression by mucosal T cells may regulate IFN-gamma expression in the intestine" J. Immunol., 2004;173(1):251-8.
Cohavy et al., "LIGHT is constitutively expressed on T and NK cells in the human gut and can be induced by CD2-mediated signaling" J. Immunol., 2005:174:646-53.
Da Silva Antunes, R. et al. "The TNF Family Molecules LIGHT and Lymphotoxin αβ Induce a Distinct Steroid-Resistant Inflammatory Phenotype in Human Lung Epithelial Cells" Journal of immunology 195(5): 2429-2441 (2015).
Da Silva Antunes, R., et al. "TNFSF14 (LIGHT) Exhibits Inflammatory Activities in Lung Fibroblasts Complementary to IL-13 and TGF-β" Front Immunol. 9:576 (2018).
Daperno M, et al."Development and validation of a new, simplified endoscopic activity score for Crohn's disease: the SES-CD" Gastroinest Endosc. Oct. 2004;60(4):505-12.

(56) References Cited

OTHER PUBLICATIONS

Doherty, T. A. et al. "The tumor necrosis factor family member LIGHT is a target for asthmatic airway remodeling" Nature medicine 17, 596-603, (2011).
Fehr, A. R., et al., "Middle East Respiratory Syndrome: Emergence of a Pathogenic Human Coronavirus" S. Annual review of medicine 68, 387-399 (2017).
Freeman, "Natural history and long-term clinical course of Crohn's disease" World J. Gastroenterol., 2014:20(1);31-36.
Funke et al., "Functional characterisation of decoy receptor 3 in Crohn's disease" Gut, Apr. 2009;58(4):483-91.
Graham, R. L., et al. "A decade after SARS: strategies for controlling emerging coronaviruses" Nature reviews. Microbiology 11(12): 836-848 (2013).
Gralinski, L. E. & Baric, R. S. "Molecular pathology of emerging coronavirus infections" The Journal of pathology 235, 185-195 (2015).
Granger et al., "Genomic characterization of light reveals linkage to an immune response locus on chromosome 19p13.3 and distinct isoforms generated by alternate splicing or proteolysis" J. Immunol., 2001:167:5122-28.
Guyatt et al., "A new measure of health status for clinical trials in inflammatory bowel disease" Gastroenterol., 1989:96;804-10.
Herro, R. & Croft, M. "The control of tissue fibrosis by the inflammatory molecule LIGHT (TNF Superfamily member 14)" Pharmacol Res 104, 151-155(2016).
Herro, R., et al. "Tumor necrosis factor superfamily 14 (LIGHT) controls thymic stromal lymphopoietin to drive pulmonary fibrosis" The Journal of allergy and clinical immunology 136(3): 757-768 (2015).
https://www.guidetopharmacology.org/GRAC/LigandDisplayForward?tab=clinical&ligandId=11774 (accessed from the internet Nov. 15, 2022).
Huang, C. et al. "Clinical features of patients infected with 2019 novel coronavirus in Wuhan, China" Lancet 395, 197-506 (2020).
Kwon, B. S. et al. "A newly identified member of the tumor necrosis factor receptor superfamily with a wide tissue distribution and involvement in lymphocyte activation" The Journal of Biological Chemistry 272, 14272-14276 (1997).
Marshall, R., et al. "The acute respiratory distress syndrome: fibrosis in the fast lane" Thorax, 53(10):815-817 (1998).
Mehta, P., et al. "Therapeutic blockade of granulocyte macrophage colony-stimulating factor in COVID-19-associated hyperinflammation: challenges and opportunities" The Lancet, 8(8): 822-830 (2020).
O'Donnell et al., "Detection of pseudodiarrhoea by simple clinical assessment of intestinal transit rate" Br. Med. J.; 300:439-40 (1990).
PCT International Search Report and Written Opinion from PCT/US21/25068, mailed on Sep. 23, 2021, 14 pages.
Perlin et al., "Levels of the TNF-Related Cytokine LIGHT Increase in Hospitalized COVID-19 Patients with Cytokine Release Syndrome and ARDS", American Society for Microbiology, mSphere 5: Jul./Aug. 2020, vol. 4, Issue 4.
Perlin et al., "Randomized, double-blind, controlled trial of human anti-LIGHT monoclonal antibody in COVID-19 acute respiratory distress syndrome", J. Clin Invest. 2021, https://doi.org/10.1172/JCI153173.
Quesnel, C. et al. "Alveolar fibroblasts in acute lung injury: biological behaviour and clinical relevance" The European respiratory journal 35(6):1312-1321 (2010).
Rioux et al., "Genome wide search in Canadian families with inflammatory bowel disease reveals two novel susceptibility loci" Am. J. Hum. Genet., 66:1863-70 (2000).
Sampson HA, et al. "Second symposium on the definition and management of anaphylaxis: Summary Report-Second National Institute of Allergy and Infectious Disease/Food Allergy and Anaphylaxis Network Symposium" J Allergy Clin Immunol; 117(2):391-97 (2006).
Sandoval-Montes, C. & Santos-Argumedo, L. "CD38 is expressed selectively during the activation of a subset of mature T cells with reduced proliferation but improved potential to produce cytokines" Journal of leukocyte biology 77, 513-521 (2005).
Shi and Ng, "The state of the art on treatment of Crohn's disease" J. Gastroenterol., 53;989-998 (2018).
Siddiqi, H.K., et al. "COVID-19 illness in native and immunosuppressed states: A clinical-therapeutic staging proposal" J Heart Lung Transplant 39(5), 405-407 (2020).
Sostegni et al., "Review: Crohn's disease: monitoring disease activity" Aliment Pharmacolo Ther., 17 (Suppl. 2) 11-17 (2003).
Arunachalam, P.S. et al. "Systems biological assessment of immunity to mild versus severe COVID-19 infection in humans" Science 369, 1210-1220 (2020).
Avalo Therapeutics Presentation, Aug. 2021, retrieved from internet at https://d1io3yogDoux5.cloudfront.net/_38c04b70cf15803567a1dff95cd79f8d/avalotx/db/282/1109/pdf/AVTX_Initial+Crohns+Data+IR+Presentation_08262021_Final+200pm.pdf on Jan. 4, 2022.
Avalo Therapeutics Presentation, Aug. 2022, retrieved from internet at https://d1io3yog0oux5.cloudfront.net/_9a4f69fa787850b8da94ce1a579b1a9d/avalotx/db/282/1287/pdf/Avalo+Investor+Deck+August+2022_vf.pdf on Oct. 27, 2022.
Avalo Therapeutics presentation, Jan. 2022, retrieved from internet at https://d1io3yog0oux5.cloudfront.net/_fa3474e444eb4a244813b1a27fa439a3/avalotx/db/282/1261/pdf/Avalo+Therapeutics+2022+Investor+Day+Presentation_Final2.pdf on Jan. 18, 2022.
Avalo Therapeutics Presentation, Mar. 2022, retrieved from internet at https://d1io3yog0oux5.cloudfront.net/_9a4f69fa787850b8da94ce1a579b1a9d/avalotx/db/282/1276/pdf/Avalo+Therapeutics+Corporate+Presentation+March+2022_FINAL.pdf on Oct. 27, 2022.
Avalo Therapeutics Presentation, Mar. 2022, retrieved from internet at https://d1io3yog0oux5.cloudfront.net/_9a4f69fa787850b8da94ce1a579b1a9d/avalotx/db/282/1245/pdf/Avalo+Therapeutics+Corporate+Presentation+March+2022_FINAL.pdf on Oct. 27, 2022.
Avalo Therapeutics Presentation, May 2022, retrieved from internet at https://d1io3yog0oux5.cloudfront.net/_9a4f69fa787850b8da94ce1a579b1a9d/avalotx/db/282/1284/pdf/Avalo+Investor+Deck_May+2022_vFinal+%2805.25%29.pdf on Oct. 27, 2022.
Avalo Therapeutics presentation, Nov. 2021, retrieved from internet at https://d1io3yog0oux5.cloudfront.net/_38c04b70cf15803567a1dff95cd79f8d/avalotx/db/282/1245/pdf/FINAL+Avalo_November+IR+Deck_1109021_Post+to+AVTXcom.pdf on Jan. 4, 2022.
Avalo Therapeutics presentation, Oct. 2021, retrieved from internet at https://d1io3yog0oux5.cloudfront.net/_38c04b70cf15803567a1dff95cd79f8d/avalotx/db/282/1242/pdf/Avalo+IR+Deck+-+IBD+Summit+-+v101321-A.pdf on Jan. 4, 2022.
Avalo Therapeutics Presentation, Sep. 2022, retrieved from internet at https://d1io3yog0oux5.cloudfront.net/_9a4f69fa787850b8da94ce1a579b1a9d/avalotx/db/282/1289/pdf/Avalo+Investor+Deck+September+2022.pdf on Oct. 27, 2022.
Avalo Therapeutics Press Release, Aug. 13, 2020, retrieved from internet at https://ir.avalotx.com/press-releases/detail/104/cerecor-announces-peer-reviewed-publication-highlighting on Jan. 4, 2022.
Avalo Therapeutics Press Release, Aug. 2, 2021, retrieved from internet at https://ir.avalotx.com/press-releases/detail/133/cerecor-reports-second-quarter-2021-financial-results-and on Jan. 4, 2022.
Avalo Therapeutics Press Release, Aug. 26, 2020, retrieved from internet at https://ir.avalotx.com/press-releases/detail/105/cerecor-resumes-phase-1b-clinical-trial-of-cerc-002-for-the on Jan. 4, 2022.
Avalo Therapeutics Press Release, Aug. 4, 2022, retrieved from internet at https://ir.avalotx.com/press-releases/detail/157/avalo-reports-second-quarter-2022-financial-results on Oct. 27, 2022.
Avalo Therapeutics Press Release, Aug. 6, 2020, retrieved from internet at https://ir.avalotx.com/press-releases/detail/103/cerecor-reports-second-quarter-2020-financial-results-and on Jan. 4, 2020.
Avalo Therapeutics Press Release, Feb. 17, 2022, retrieved from internet at https://ir.avalotx.com/press-releases/detail/147/avalo-therapeutics-announces-leadership-transition on Oct. 27, 2022.

(56) References Cited

OTHER PUBLICATIONS

Avalo Therapeutics Press Release, Jan. 5, 2021, retrieved from internet at https://ir.avalotx.com/press-releases/detail/114/cerecor-announces-successful-proof-of-concept-data-for on Jan. 4, 2022.
Avalo Therapeutics Press Release, Jan. 6, 2022, retrieved from internet at https://d1io3yog0oux5.cloudfront.net/_fa3474e444eb4a244813b1a27fa439a3/avalotx/news/2022-01-06_Avalo_Reports_Positive_Phase_1b_Results_for_AVTX_144.pdf on Jan. 18, 2022.
Avalo Therapeutics Press Release, Jul. 21, 2020, retrieved from internet at https://ir.avalotx.com/press-releases/detail/99/cerecor-announces-first-patient-enrolled-in-multicenter on Jan. 4, 2022.
Avalo Therapeutics Press Release, Jul. 26, 2021, retrieved from the internet at https://ir.avalotx.com/press-releases/detail/131/cerecor-announces-positive-initial-phase-1b-results-for on Jan. 4, 2022.
Avalo Therapeutics Press Release, Mar. 2, 2021, retrieved from internet at https://ir.avalotx.com/press-releases/detail/121/cerecor-announces-cerc-002-significantly-reduced on Jan. 4, 2022.
Avalo Therapeutics Press Release, Mar. 2, 2022, retrieved from internet at https://ir.avalotx.com/press-releases/detail/148/avalo-therapeutics-reports-2021-financial-results on Oct. 27, 2022.
Avalo Therapeutics Press Release, Mar. 29, 2021, retrieved from internet at https://ir.avalotx.com/press-releases/detail/124/cerecor-announces-new-worldwide-license-agreement-with on Jan. 4, 2022.
Avalo Therapeutics Press Release, Mar. 8, 2021, retrieved from internet at https://ir.avalotx.com/press-releases/detail/123/cerecor-reports-2020-financial-results-and-provides on Jan. 4, 2022.
Avalo Therapeutics Press Release, May 11, 2021, retrieved from internet at https://ir.avalotx.com/press-releases/detail/126/fda-grants-fast-track-designation-to-cerc-002-for-treatment on Jan. 4, 2022.
Avalo Therapeutics Press Release, May 13, 2021, retrieved from internet at https://ir.avalotx.com/press-releases/detail/127/cerecor-reports-first-quarter-2021-financial-results-and on Jan. 4, 2022.
Avalo Therapeutics Press Release, May 18, 2022, retrieved from internet at https://ir.avalotx.com/press-releases/detail/152/avalo-therapeutics-announces-first-patient-dosed-in-the on Oct. 27, 2022.
Avalo Therapeutics Press Release, May 26, 2020, retrieved from internet at https://ir.avalotx.com/press-releases/detail/93/cerecor-and-myriad-genetics-announce-that-levels-of-light on Jan. 4, 2022.
Avalo Therapeutics Press Release, May 28, 2020, retrieved from internet at https://ir.avalotx.com/press-releases/detail/94/cerecor-announces-fda-clearance-of-ind-for-cerc-002-in on Jan. 4, 2022.
Avalo Therapeutics Press Release, May 5, 2022, retrieved from internet at https://ir.avalotx.com/press-releases/detail/150/avalo-therapeutics-first-quarter-2022-financial-results on Oct. 27, 2022.
Avalo Therapeutics Press Release, Nov. 9, 2020, retrieved from internet at https://ir.avalotx.com/press-releases/detail/108/cerecor-reports-third-quarter-2020-financial-results-and on Jan. 4, 2022.
Avalo Therapeutics Press Release, Nov. 9, 2021, retrieved from internet at https://ir.avalotx.com/press-releases/detail/140/avalo-reports-third-quarter-2021-financial-results-and on Jan. 4, 2022.
Avalo Therapeutics Press Release, Sep. 6, 2022, retrieved from internet at https://ir.avalotx.com/press-releases/detail/160/avalo-advances-btla-agonist-fusion-protein-avtx-008-to on Oct. 27, 2022.
Best et al. (1976) "Development of a Crohn's disease activity index, National Cooperative Crohn's Disease Study" Gastroenterol., 1976:70;439-44.
Cardinale et al., "Targeted resequencing identifies defective variants of decoy receptor 3 in pediatric-onset inflammatory bowel disease" Genes Immun. Oct. 2013:14(7):447-52.
Cerecor presentation, Aug. 2020, retrieved from internet at https://d1io3yog0oux5.cloudfront.net/_38c04b70cf15803567a1dff95cd79f8d/avalotx/db/282/1235/pdf/Updated_08102020_IR+Presentation+for+WedBush+Healthcare+Conference+Final.pdf on Jan. 4, 2022.
Cerecor presentation, Biomarker Study Results, May 2020, retrieved from internet at https://d1io3yog0oux5.cloudfront.net/_38c04b70cf15803567a1dff95cd79f8d/avalotx/db/282/1231/pdf/Cerecor+COVID-19+Biomarker+Study+Results+in+ARDS+Final+for+CERC.com+%281%29.pdf on Jan. 4, 2022.
Cerecor Presentation, Dec. 2019, retrieved from internet at https://d1io3yog0oux5.cloudfront.net/_38c04b70cf15803567a1dff95cd79f8d/avalotx/db/282/1237/pdf/Cerecor-Aevi+Merger+Deck_01082020.pdf on Jan. 4, 2022.
Cerecor presentation, Jan. 2021, retrieved from internet at https://d1io3yog0oux5.cloudfront.net/_38c04b70cf15803567a1dff95cd79f8d/avalotx/db/282/1230/pdf/JAN_2021_IR_CERC002+COVID-19+ARDS+Trial_JAN_5_2021_+800am+FINAL%281%29.pdf on Jan. 4, 2022.
Cerecor presentation, Jan. 2021, retrieved from internet at https://d1io3yog0oux5.cloudfront.net/_38c04b70cf15803567a1dff95cd79f8d/avalotx/db/282/1229/pdf/Cerecor_IR+Deck+Jan+2021+Updated+7JAN_2021+FINAL+for+Cerecor+Website.pdf on Jan. 4, 2022.
Cerecor presentation, Jul. 2021, retrieved from internet at https://d1io3yog0oux5.cloudfront.net/_38c04b70cf15803567a1dff95cd79f8d/avalotx/db/282/1227/pdf/CERC-002+Initial+Crohns+Data+Investor+Presentation.pdf on Jan. 4, 2022.
Cerecor presentation, Jul. 2021, retrieved from internet at https://d1io3yog0oux5.cloudfront.net/_38c04b70cf15803567a1dff95cd79f8d/avalotx/db/282/1226/pdf/Cerecor+July+2021+Corporate+Presentation.pptx+%281%29.pdf on Jan. 4, 2022.
Cerecor presentation, Jun. 2020, retrieved from internet at https://d1io3yog0oux5.cloudfront.net/_38c04b70cf15803567a1dff95cd79f8d/avalotx/db/282/1233/pdf/CERC+Jefferies+Virtual+Healthcare+Conference+Presentation+Final.pdf on Jan. 4, 2022.
Cerecor presentation, Jun. 2021, retrieved from internet at https://d1io3yog0oux5.cloudfront.net/_38c04b70cf15803567a1dff95cd79f8d/avalotx/db/282/1142/pdf/Cerecor+Jefferies+Virtual+Healthcare+Conference+2JUNE2021.pdf on Jan. 4, 2022.
Cerecor presentation, Mar. 17, 2021, retrieved from internet at https://d1io3yog0oux5.cloudfront.net/_38c04b70cf15803567a1dff95cd79f8d/avalotx/db/282/1129/pdf/Cerecor+OpCo+Presentation+Deck_03172021_Final.pdf on Jan. 4, 2022.
Cerecor presentation, Mar. 2, 2021, retrieved from internet at https://d1io3yog0oux5.cloudfront.net/_38c04b70cf15803567a1dff95cd79f8d/avalotx/db/282/1228/pdf/CERC_002_COVID_Final+Data+60+Day+Safety+Short+Deck_01032021_FINAL.pdf on Jan. 4, 2022.
Cerecor presentation, May 2020, retrieved from internet at https://d1io3yog0oux5.cloudfront.net/_38c04b70cf15803567a1dff95cd79f8d/avalotx/db/282/1232/pdf/Cerecor+COVID-19+ARDS+Deck+Final+_05272020+Final.pdf on Jan. 4, 2022.
Cerecor presentation, Sep. 14, 2020; retrieved from internet at https://d1io3yog0oux5.cloudfront.net/_38c04b70cf15803567a1dff95cd79f8d/avalotx/db/282/1234/pdf/Updated_09142020_IR+Presentation+for+HCWainwright+Virtual+Healthcare+Conference.pdf on Jan. 4, 2022.
Cerecor presentation, Feb. 2020, retrieved from internet at https://d1io3yog0oux5.cloudfront.net/_38c04b70cf15803567a1dff95cd79f8d/avalotx/db/282/1236/pdf/Cerecor+IR+Deck+FEB+2020.pdf on Jan. 4, 2022.
Cerecor Press Release on Dec. 5, 2019, retrieved from internet at https://ir.cerecor.com/press-releases/detail/86/cerecor-to-acquire-aevi-genomic-medicine, on Jul. 7, 2021.
Convertino, Irma et al., "Exploring pharmacological approaches for managing cytokine storm associated with pneumonia and acute respiratory distress syndrome in COVID-19 patients", Critical Care (2020) 24:331, 6 pages.
Ragel, Emma J. et al., "Acute respiratory distress syndrome: potential of therapeutic interventions effective in treating progression from COVID-19 to treat progression from other illnesses—a systematic review", BMJ Open Respiratory Research, vol. 10, No. 1, Sep. 1, 2023, e001525.

| Standard Antigen | R & D Systems – 664-LI-025 | | | | | | | |
|---|---|---|---|---|---|---|---|---|
| Capture Ab Beads | Enzo ALX-804-841-C100 | | | | | | | |
| Detection Ab | ProSci RF16062 | | | | | | | |
| Linearity Starting at 1:5 Sample Dilution | | | | | | | | |
| Sample ID | Serum 1 | Serum 2 | Serum 3 | Serum 4 | Serum 5 | Serum 6 | Serum 7 | Serum 8 |
| 1:10 | 103% | 124% | 104% | 119% | 130% | 103% | 140% | 106% |
| 1:20 | 112% | 135% | 111% | 122% | 121% | 111% | 152% | 109% |
| 1:40 | 109% | 138% | 113% | 115% | 115% | 101% | 153% | 111% |
| Linearity Starting at 1:10 Sample Dilution | | | | | | | | |
| Sample ID | Serum 1 | Serum 2 | Serum 3 | Serum 4 | Serum 5 | Serum 6 | Serum 7 | Serum 8 |
| 1:20 | 109% | 110% | 106% | 103% | 94% | 108% | 108% | 103% |
| 1:40 | 106% | 111% | 108% | 96% | 89% | 98% | 109% | 105% |

FIG. 1

Enzo/ProSci Linearity

| Dilution | Sample ID | MFI | Results (pg/mL) | Linearity |
|---|---|---|---|---|
| 1:10 | Plasma 1 | 910 | 46 | |
| | Plasma 2 | 397 | 20 | |
| | Plasma 3 | 971 | 49 | |
| | Plasma 4 | 735 | 37 | |
| | Serum 1 | 577 | 29 | |
| | Serum 2 | 934 | 47 | |
| | Serum 3 | 682 | 34 | |
| | Serum 4 | 676 | 34 | |
| 1:20 | Plasma 1 | 445 | 22 | 98% |
| | Plasma 2 | 201 | 9.8 | 98% |
| | Plasma 3 | 545 | 28 | 112% |
| | Plasma 4 | 399 | 20 | 108% |
| | Serum 1 | - | - | - |
| | Serum 2 | - | - | - |
| | Serum 3 | 333 | 17 | 97% |
| | Serum 4 | 377 | 19 | 111% |
| 1:40 | Plasma 1 | 210 | 10 | 89% |
| | Plasma 2 | 104 | 4.5 | 91% |
| | Plasma 3 | 257 | 13 | 104% |
| | Plasma 4 | 203 | 9.9 | 106% |
| | Serum 1 | 173 | 8.3 | 113% |
| | Serum 2 | 267 | 13 | 112% |
| | Serum 3 | 186 | 9.0 | 104% |
| | Serum 4 | 193 | 9.3 | 109% |
| 1:80 | Plasma 1 | 109 | 4.8 | 84% |
| | Plasma 2 | 59 | 2.0 | 81% |
| | Plasma 3 | 142 | 6.6 | 107% |
| | Plasma 4 | 101 | 4.3 | 94% |
| | Serum 1 | 89 | 3.7 | 101% |
| | Serum 2 | 140 | 6.5 | 110% |
| | Serum 3 | 104 | 4.5 | 106% |
| | Serum 4 | 99 | 4.2 | 99% |

FIG. 2A

| Capture Ab | Enzo ALX-804-841-C100 | |
|---|---|---|
| Detection Ab | ProSci RF16062 | |
| High Standard Concentration | Name | Average MFI |
| 50 pg/mL LIGHT | 10,000 ng/mL DcR3 | 361 |
| | 2,500 ng/mL DcR3 | 339 |
| | 625 ng/mL DcR3 | 322 |
| | 156 ng/mL DcR3 | 359 |
| | 39 ng/mL DcR3 | 1721 |
| | 10 ng/mL DcR3 | 6342 |
| | 2.4 ng/mL DcR3 | 8344 |
| | 0.61 ng/mL DcR3 | 8921 |
| | 0.15 ng/mL DcR3 | 10880 |
| | 0.038 ng/mL DcR3 | 9110 |
| | 0.0095 ng/mL DcR3 | 9499 |
| | 0 ng/mL DcR3 | 9938 |

FIG. 3

| Capture Ab | Enzo ALX-804-841-C100 | | |
|---|---|---|---|
| Detection Ab | ProSci RF16062 | | |
| Unspiked Sample MFI | DcR3 (10 μg/mL) Interference | Reference Sample (Control) | Percent Recovery – DcR3 |
| Plasma 1 (1:10) | 625 | 832 | 75% |
| Plasma 2 (1:10) | 156 | 318 | 49% |
| Plasma 3 (1:10) | 412 | 837 | 49% |
| Plasma 4 (1:10) | 342 | 543 | 63% |
| Serum 1 (1:10) | 114 | 513 | 22% |
| Serum 2 (1:10) | 313 | 834 | 38% |
| Serum 3 (1:10) | 182 | 560 | 32% |
| Serum 4 (1:10) | 191 | 604 | 32% |
| Spiked Sample (40 pg/mL LIGHT) MFI | DcR3 (10 μg/mL) Interference | Reference Sample (Control) | Percent Recovery – DcR3 |
| Plasma 1 (1:10) | 536 | 1563 | 34% |
| Plasma 2 (1:10) | 178 | 1065 | 17% |
| Plasma 3 (1:10) | 338 | 1521 | 22% |
| Plasma 4 (1:10) | 297 | 1437 | 21% |
| Serum 1 (1:10) | 108 | 1358 | 8% |
| Serum 2 (1:10) | 289 | 1467 | 20% |
| Serum 3 (1:10) | 165 | 1522 | 11% |
| Serum 4 (1:10) | 200 | 1627 | 12% |

*FIG. 4A*

| Capture Ab | ProSci RF16062 | |
|---|---|---|
| Detection Ab | LSBio LS-C133566-100 | |
| Unspiked Sample MFI | DcR3 (10 µg/mL) Interference | Reference Sample (Control) | Percent Recovery – DcR3 |
| Plasma 1 (1:4) | 364 | 421 | 86% |
| Plasma 2 (1:4) | 92 | 103 | 89% |
| Plasma 3 (1:4) | 226 | 277 | 82% |
| Plasma 4 (1:4) | 189 | 208 | 91% |
| Serum 1 (1:4) | 81 | 88 | 92% |
| Serum 2 (1:4) | 181 | 219 | 83% |
| Serum 3 (1:4) | 128 | 149 | 86% |
| Serum 4 (1:4) | 145 | 154 | 95% |
| Spiked Sample (150 pg/mL LIGHT) MFI | DcR3 (10 µg/mL) Interference | Reference Sample (Control) | Percent Recovery – DcR3 |
| Plasma 1 (1:4) | 299 | 1170 | 26% |
| Plasma 2 (1:4) | 95 | 1508 | 6% |
| Plasma 3 (1:4) | 197 | 1400 | 14% |
| Plasma 4 (1:4) | 173 | 1284 | 13% |
| Serum 1 (1:4) | 73 | 1139 | 6% |
| Serum 2 (1:4) | 137 | 1183 | 12% |
| Serum 3 (1:4) | 124 | 1484 | 8% |
| Serum 4 (1:4) | 130 | 1371 | 10% |

FIG. 4B

METHODS OF TREATING PNEUMONIA OR RESPIRATORY FAILURE ASSOCIATED WITH COVID-19 BY ADMINISTERING AN ANTI-LIGHT ANTIBODY

CROSS-REFERENCE TO RELATED APPLICATIONS

This application is a continuation application of U.S. application Ser. No. 17/218,449, filed Mar. 31, 2021, now granted as U.S. Pat. No. 11,708,406, which claims the benefit of priority to U.S. Provisional Application No. 63/003,826, filed Apr. 1, 2020, U.S. Provisional Application No. 63/027,127, filed May 19, 2020, and U.S. Provisional Application No. 63/133,636, filed Jan. 4, 2021, the contents of each of which are incorporated herein by reference for all purposes.

SEQUENCE LISTING

The instant application contains a Sequence Listing which has been submitted electronically in XML format and is hereby incorporated by reference in its entirety. Said XML copy, created on Jun. 1, 2023, is named "2023-06-01-01118-0047-01US-ST26" and is 106,445 bytes in size.

FIELD OF THE INVENTION

The present disclosure relates to methods of diagnosing and treating subjects with conditions associated with elevated free LIGHT levels, including subjects with Crohn's Disease (CD) or an inflammatory condition associated with Crohn's Disease, subjects with immune dysregulation that may lead to multisystem organ failure, or subjects with acute lung injury (ALI) or acute respiratory distress syndrome (ARDS), including those associated with coronavirus infection, including COVID-19. For example, in some embodiments, the subjects may be treated with anti-LIGHT antibodies. The disclosure also relates to a novel assay for detecting free LIGHT.

BACKGROUND OF THE INVENTION

In December 2019, the spread of 2019 novel coronavirus 2019-nCoV (SARS-CoV-2) has emerged as a global emergency, causing both high morbidity and mortality. SARS-CoV-2 originated in Wuhan China (Wu, F. et al. Nature 579, 265-269 (2020)) but has rapidly spread worldwide and has been designated a global pandemic by the World Health Organization. The virus is highly infectious and it is estimated that up to 60% of the world's population may eventually become infected by SARS-CoV-2. In the US alone this would represent more than 180 million individuals.

COVID-19 is a disease caused by SARS-CoV-2. The initial presentation of COVID-19 infection includes fever with or without respiratory symptoms including cough, shortness of breath, and pneumonia. In most subjects the illness is mild and self-limited, however 15% to 20% experience severe respiratory illness, requiring hospitalization and oxygen therapy. (Huang, C. et al. *Lancet* 395, 497-506 (2020)). Many of these subjects require intensive care and ventilation owing to emergence of acute respiratory distress syndrome (ARDS), (id.; Graham, R. L., Donaldson, E. F. & Baric, R. S. *Nature reviews. Microbiology* 11, 836-848 (2013)), which is a well-described and potentially fatal complication of other viral respiratory syndromes (i.e., SARS, MERS, and H1N1). Other complications of COVID-19 include arrhythmia, shock, acute kidney injury, acute cardiac injury, liver dysfunction, and secondary infection. (Huang C, et al., *Lancet* (2020); Wang, D. et al., *JAMA* (2020)).

Accumulating evidence suggest that the main cause for mortality is unleashed immune response causing cytokine storm, acute lung injury, and Acute Respiratory Disease Syndrome (ARDS) resulting in fatal respiratory failure. Even in subjects who recover there may be long-lasting and debilitating sequelae. There is an urgent need for cytokine-neutralizing therapeutic agents, which will control COVID-19 associated hyper-inflammation and ARDS.

In COVID-19 and other human corona respiratory virus (hCoV) infections, ARDS appears to result from a dysregulated hyperinflammatory response manifested by the release of excessive pro-inflammatory cytokines and chemokines, coined "cytokine storm." (Channappanavar, R. & Perlman, S. *Seminars in immunopathology* 39, 529-539, (2017); Mehta, P. *The Lancet* (2020)). Cytokines and chemokines have long been thought to play an important role in immunity and immunopathology during virus infections. A rapid and well-coordinated innate immune response is the first line of defense against viral infections, but dysregulated and excessive immune responses may cause immunopathology. (Fehr, A. R., Channappanavar, R. & Perlman, S. *Annual review of medicine* 68, 387-399 (2017); Channappanavar, R. et al. Cell host & microbe 19, 181-193 (2016)). Although there is no direct evidence for the involvement of pro-inflammatory cytokines and chemokines in lung pathology during SARS and MERS, correlative evidence from subjects with severe disease suggests a role for hyper-inflammatory responses in hCoV pathogenesis. (Channappanavar, *Seminars in immunopathology* 39, 529-539 (2017); Mehta (2020); Sandoval-Montes, C. & Santos-Argumedo, L. *Journal of leukocyte biology* 77, 513-521 (2005); Xu et al., *Microbiol* 6(10):130 (2019)).

The cytokine storm in COVID-19 infection is thought to result from initial rapid virus replication which may be more likely in immunocompromised subjects. A notable feature of pathogenic human coronaviruses such as SARS-CoV and MERS-CoV is that both viruses replicate to high titers very early after infection both in vitro and in vivo (Gralinski, L. E. & Baric, R. S. *The Journal of pathology* 235, 185-195 (2015)). This high replication could lead to enhanced cytopathic effects and production of higher levels of pro-inflammatory cytokines and chemokines by infected epithelial cells. (Xiao, F. et al. *Gastroenterology* (2020)). These cytokines and chemokines in turn orchestrate massive infiltration of inflammatory cells into the lungs. (Gralinski, L. E. & Baric, R. S. The Journal of pathology 235, 185-195 (2015)). Studies from hCoV infections in humans and experimental animals demonstrated a strong correlation between high SARS-CoV and MERS-CoV titers and disease severity. Infection also appears to increase secretion of cytokines (e.g., IL4 and IL10) which in turn can increase T cell activation. (Sandoval-Montes (2005); Xu, Z. et al. *The Lancet. Respiratory medicine* (2020)). Thus, the cytokine storm that drives tissue injury and vascular permeability in the lungs is likely mediated, in part by T cell activation with increased expression of cytokines.

In addition, reports indicate that pulmonary (lung) fibrosis, which is known to be a result of ARDS, is a known COVID-19 infection complication. (Huang, C. et al. *Lancet* 395, 497-506 (2020)).

Both human and animal studies demonstrate accumulation of inflammatory monocyte-macrophages and neutrophils in the lungs following hCoV infection. These cells are the predominant source of cytokines and chemokines associated with hCoV lethal disease observed both in humans and animal models. (Channappanavar, *Seminars in immunopathology* (2017)).

While a primary focus of treatment of COVID-19 is the development of appropriate antiviral and vaccination approaches, currently no established therapy exists for treatment of ARDS associated with COVID-19. Agents targeting cytokine storm have included cytokine-directed therapies, including IL-1β and IL-6 antagonists; however, there is no established single therapy for the treatment and/or prevention of ALI associated with cytokine storm. The development of a safe and effective therapy for COVID-19-associated acute lung injury (ALI) and ARDS could significantly reduce the mortality and post infectious morbidity of this global pandemic and alleviate the severe strain placed on healthcare systems.

Further, the initial clinical sign of COVID-19 that allowed case detection was pneumonia (Chan, J F, et al., *Lancet* (2020)). Complications of COVID-19 pneumonia include acute respiratory distress syndrome (ARDS), arrhythmia, shock, acute kidney injury, acute cardiac injury, liver dysfunction, and secondary infection (Huang C, et al., *Lancet* (2020); Wang, D. et al., *JAMA* (2020)). The main cause of mortality in COVID-19 appears to be dysregulated hyperimmune response causing cytokine storm, acute lung injury and ARDS. Fifteen to 20% of COVID-19 patients experience severe respiratory illness, requiring hospitalization and oxygen therapy (Huang C, et al., *Lancet* (2020)). There are currently no treatments to prevent progression of COVID-19 pneumonia to ARDS in patients with COVID-19.

Crohn's Disease (CD) is an idiopathic, chronic, inflammatory condition of the gastrointestinal tract with a high risk for complications and need for surgical interventions. Crohn's Disease is a life-long disorder that may become clinically apparent at almost any time from early childhood to late adulthood. (Freeman, Natural history and long-term clinical course of Crohn's disease, *World J Gastroenterol.*, 2014:20(1); 31-36). The typical age of detection or diagnosis of the disease is usually during the late teens and early twenties, and during the last two to three decades, over 80% of patients with Crohn's Disease are diagnosed before age 40. (Freeman 2014).

Crohn's Disease may impact the entire gastrointestinal tract. (Shi and Ng, The state of the art on treatment of Crohn's disease, *J Gastroenterol.*, 2018:53; 989-998). The majority of patients have a chronic intermittent course during 10 years after diagnosis. The disease appears to be progressive, although the rate of progression may be altered or slowed by the use of medication or with surgical intervention. (Freeman 2014). Common symptoms include diarrhea, abdominal pain, rectal bleeding, fever, weight loss, and fatigue. (Veauthier and Hornecker, Crohn's Disease: Diagnosis and Management, *Am. Fam. Physician,* 2018:98(11); 661-669).

Corticosteroids and thiopurines remain the main treatments, while anti-TNF agents are being increasingly prescribed earlier in disease course. (Shi and Ng 2018). Anti-TNF therapies are recommended in patients with high risk for unfavorable prognosis. (Shi and Ng 2018). However, primary non-response or secondary loss of response to anti-TNF therapy occurs in a large proportion of patients. (Shi and Ng 2018). Therefore, new and improved therapies are needed.

An important immunoregulatory cytokine, LIGHT (acronym for "homologous to Lymphotoxin, exhibits Inducible expression and competes with HSV Glycoprotein D for binding to HVEM (herpesvirus entry mediator), a receptor expressed on T lymphocytes"), also known as TNFSF14 (tumor necrosis factor superfamily member 14) is secreted in high levels during viral infection, which supports ARDS-related pulmonary fibrosis and cytokine storm. (Xu, W. et al. *Frontiers in Microbiology* 10, 130 (2019)). Neutrophils and macrophages express high levels of LIGHT and TNF and are a major source of these inflammatory cytokines. (Kwon, B. S. et al. *The Journal of Biological Chemistry* 272, 14272-14276 (1997)).

LIGHT (TNFSF 14) belongs to the tumor necrosis factor superfamily and is expressed by activated T cells, monocytes-macrophages and additional types of antigen presenting cells. LIGHT is considered one of the "Master Regulators" of the immune system and has a key role in the communication system which controls immune response. LIGHT has a dual mechanism of action; exerting its effects by activating both T cells and B cells as well as upregulating other inflammatory cytokines.

LIGHT activates two key receptors, herpesvirus entry mediator (HVEM) and lymphotoxin β receptor (LT 3R), both expressed on lung epithelial cells. Early in infection LIGHT released from neutrophils and macrophages bind cellular receptors, which causes inflammatory cell infiltration, releasing high level of TNF and additional pro-inflammatory cytokines. LIGHT also has a co-stimulatory role in T cell activation driving proinflammatory and tissue damaging effects. (Ware, C. F. *Advances in experimental medicine and biology* 647, 146-155 (2009); Ware, C. F. *Immunological reviews* 223, 186-201 (2008)). Therefore, LIGHT has roles in many immune-mediated pathologies such as Crohn's Disease, IBD, Rheumatoid arthritis, and fibrosis. An additional receptor for LIGHT is a decoy receptor (coined DCR3), which binds LIGHT and interferes with its activity by competing with receptor binding. (Steinberg, M. W., et al., M. *Seminars in immunopathology* 31, 207-221 (2009); Wroblewski, V. J. et al. *Biochemical pharmacology* 65, 657-667 (2003)). In hyper inflammation and cytokine storm conditions, DcR3 is likely to be overwhelmed, generating high DCR3-free (active) LIGHT.

LIGHT has been shown to play a key role in viral pneumonia. LIGHT protein has been reported to be elevated in PBMCs of subjects presenting severe pneumonia caused by viral infection, as a part of the TNF family and IL-1 family of genes and cognate proteins elevated in these subjects compared to healthy controls. (Xu (2019)). LIGHT levels correlate with disease severity—as disease progressed from minor to severe, LIGHT levels were elevated.

High LIGHT levels in the lung may be a driver of pulmonary fibrosis. Alveolar and interstitial fibrosis is a hallmark of ARDS, (Marshall, R., Bellingan, G. & Laurent, G. *Thorax* 53, 815-817 (1998)) and is a cause for further lung injury and the need for supportive mechanical ventilation. Over-activated fibroblasts are a major cause for pulmonary fibrosis. After an infection, fibroblasts proliferate, differentiate into myofibroblasts and migrate to the alveolar airspace. Over activated myofibroblasts secrete extra cellular matrix and form attachments to the basement membrane. Consequently, this process results in obliteration of alveolar spaces with an irregular extracellular matrix. (Quesnel, C. et al. *The European respiratory journal* 35, 1312-1321 (2010)). LIGHT supports pulmonary fibrosis in several mechanisms. Recently, da Silva et al (da Silva Antunes, R., Mehta, A. K., Madge, L., Tocker, J. & Croft, M. *Front Immunol* 9, 576 (2018)), described the role of LIGHT via its receptor LTβR in promoting fibroblasts proliferation in the process of pulmonary fibrosis.

Genetic deficiency in LIGHT, and blocking LIGHT binding to both of its receptors, strongly reduced tissue remodeling and fibrosis in the lungs of allergen-challenged mice in models of severe asthma and in a model of idiopathic pulmonary fibrosis. (Doherty, T. A. et al. *Nature medicine* 17, 596-603, (2011)). Neutralizing LIGHT demonstrate reduced fibrosis phenotype. (Da Silva (2018); Herro, R. & Croft, M. *Pharmacol Res* 104, 151-155(2016)). This strategy of neutralizing LIGHT as a treatment for fibrosis should be relevant for ARDS derived fibrosis. High LIGHT levels induce high cytokines secretion by bronchial and alveolar epithelial cells in-vitro, via LTβR and HVEM (TNFRSF14), which support steroid-resistant lung inflammation. (da Silva Antunes, R., Madge, L., Soroosh, P., Tocker, J. & Croft, M. *Journal of immunology* (Baltimore, Md.: 1950) 195, 2429-2441(2015); Herro, R., Da Silva Antunes, R., Aguilera, A. R., Tamada, K. & Croft, M. *The Journal of allergy and clinical immunology* 136, 757-768 (2015)).

LIGHT has a role as an important mediator in mucosal inflammation and inflammatory bowel disease (IBD) pathogenesis (Cohavy et al., LIGHT expression by mucosal T cells may regulate IFN-gamma expression in the intestine, *J. Immunol.*, 2004; 173(1):251-8; Ware, CF, Network Communications: Lymphotoxins, LIGHT and TNF, *Annual Rev. Immunol.*, 2005: 23:787-819; Cohavy et al., LIGHT is constitutively expressed on T and NK cells in the human gut and can be induced by CD2-mediated signaling, *J. Immunol.*, 2005:174:646-53; Wang et al., The critical role of LIGHT in promoting intestinal inflammation and Crohn's disease, *J. Immunol.*, 2005:174; 8173-82). The human LIGHT gene maps to chromosome 19p13.3, a region that has been implicated in the pathogenesis of CD (Granger et al., Genomic characterization of light reveals linkage to an immune response locus on chromosome 19p13.3 and distinct isoforms generated by alternate splicing or proteolysis, *J. Immunol.*, 2001:167:5122-28; Rioux et al., Genome wide search in Canadian families with inflammatory bowel disease reveals two novel susceptibility loci, *Am. J. Hum. Genet.*, 2000:66:1863-70). The concept that LIGHT provides a critical pro-inflammatory signal during cellular immune responses is reinforced by studies in IBD patients. LIGHT messenger ribonucleic acid (RNA) is upregulated in biopsies from inflamed areas of small bowel (Cohavy et al., LIGHT is constitutively expressed on T and NK cells in the human gut and can be induced by CD2-mediated signaling, *J. Immunol.*, 2005:174:646-53).

Decoy receptor 3 belongs to the TNF superfamily (TNFRSF6B) (Yu et al., A newly identified member of tumor necrosis factor receptor superfamily (TR6) suppresses LIGHT-mediated apoptosis, *J. Biol. Chem.*, 1999: 274(20): 13733-6). It acts as a decoy receptor that competes with death receptors for ligand binding and is postulated to play a regulatory role in suppressing Fas ligand (FasL)- and LIGHT-mediated cell death and T cell activation as well as to induce angiogenesis via neutralization of TNF-like ligand 1A (TL1A) (Yu et al. 1999). Decoy receptor 3 is overexpressed in the epithelial layer of ileum specimens in patients with CD, both at actively inflamed and non-active sites. Decoy receptor 3 serum levels are significantly elevated in patients with active and non-active CD compared with healthy controls. The expression of DcR3 in intestinal epithelial cells is induced by TNFα. Increased DcR3 expression is associated with activation of nuclear factor kappa B (NF-κB) and results in protection of intestinal epithelial cells and lamina propria T cells from CD95L-induced apoptosis (Funke et al., Functional characterisation of decoy receptor 3 in Crohn's disease. *Gut,* 2009: April; 58(4):483-91). Defective variants of DcR3 have recently been observed in patients with pediatric onset IBD which further suggests an important protective role for DcR3 (Cardinale et al., Targeted resequencing identifies defective variants of decoy receptor 3 in pediatric-onset inflammatory bowel disease, *Genes Immun.* 2013: October; 14(7):447-52), potentially by moderating the effects of TNF and LIGHT.

The roles of LIGHT and DcR3 in the pathogenesis of IBD, described above, provide a rationale for the study of an anti-LIGHT monoclonal antibody in CD patients with or without loss-of-function mutations in DcR3.

Most currently available assays only measure total LIGHT, which includes LIGHT bound to its receptors, including DcR3. Total LIGHT may not provide as accurate of a picture of the levels of LIGHT causing disease, which may be free, unbound LIGHT. Thus, there is a need for improved LIGHT assays that measure free LIGHT alone.

SUMMARY OF THE INVENTION

The present disclosure includes, for example, any one or a combination of the following embodiments:

Embodiment 1. A method of detecting the presence of free LIGHT in a biological sample of a subject comprising the steps of:
 (a) contacting the biological sample with at least one anti-LIGHT antibody;
 (b) incubating the biological sample to allow the anti-LIGHT antibody to bind to free LIGHT; and
 (c) detecting the presence of complexes formed between the anti-LIGHT antibody and free LIGHT in the biological sample.

Embodiment 2. A method of diagnosing a condition associated with elevated free LIGHT in a subject comprising the steps of:
 (a) contacting a biological sample with at least one anti-LIGHT antibody;
 (b) incubating the biological sample to allow the anti-LIGHT antibody to bind to free LIGHT;
 (c) detecting the presence of complexes formed between the anti-LIGHT antibody and free LIGHT in the biological sample; and
 (d) diagnosing the subject as having a condition associated with elevated free LIGHT if a higher level of free LIGHT is detected as compared to a control.

Embodiment 3. A method of treating a condition associated with elevated free LIGHT, comprising administering to a subject in need thereof an effective amount of an anti-LIGHT antibody.

Embodiment 4. A method of treating a condition associated with elevated free LIGHT in a subject in need thereof, comprising:
 (a) contacting a biological sample isolated from the subject with a first anti-LIGHT antibody;
 (b) incubating the biological sample to allow the first anti-LIGHT antibody to bind to free LIGHT;
 (c) detecting the presence of complexes formed between the first anti-LIGHT antibody and free LIGHT in the biological sample; and
 (d) administering to the subject an effective amount of a second anti-LIGHT antibody, wherein the first and the second antibody differ, thereby treating the condition associated with elevated free LIGHT.

Embodiment 5. The method of any one of embodiments 2-4, wherein the condition associated with elevated free LIGHT comprises any one or more of:
  (a) inflammation, optionally wherein the inflammation is hyperinflammation;
  (b) immune dysregulation that leads to multisystem organ failure;
  (c) acute lung injury (ALI), optionally wherein the ALI is associated with a bacterial or viral infection, including coronavirus infection;
  (d) acute respiratory distress syndrome (ARDS), optionally wherein the ARDS is associated with a bacterial or viral infection, including coronavirus infection;
  (e) cytokine storm that drives tissue injury and vascular permeability;
  (f) post-infection pulmonary fibrosis; and
  (g) pneumonia, optionally wherein the pneumonia is associated with a bacterial or viral infection, including coronavirus infection.

Embodiment 6. The method of any one of embodiments 2, 4, and 5, wherein the detection of free LIGHT indicates that treatment of the condition associated with elevated free LIGHT with an anti-LIGHT antibody will be effective.

Embodiment 7. The method of any one of embodiments 3-6, wherein the anti-LIGHT antibody administered to the subject suppresses T cell activation.

Embodiment 8. The method of any one of embodiments 3-7, wherein the anti-LIGHT antibody administered to the subject suppresses increased expression of cytokines.

Embodiment 9. The method of any one of embodiments 3-8, wherein the anti-LIGHT antibody administered to the subject reduces the subject's risk of mortality or morbidity.

Embodiment 10. The method of any one of embodiments 3-9, wherein the anti-LIGHT antibody administered to the subject prevents progression to ARDS.

Embodiment 11. The method of any one of embodiments 3-10, wherein the anti-LIGHT antibody administered to the subject prevents the need for ventilation/intubation of the subject.

Embodiment 12. A method of treating severe COVID-19 pneumonia comprising administering an anti-LIGHT antibody to a subject in need thereof.

Embodiment 13. A method of treating acute inflammatory disease associated with COVID-19 pneumonia comprising administering an anti-LIGHT antibody to a subject in need thereof.

Embodiment 14. A method of treating respiratory failure associated with COVID-19 pneumonia comprising administering an anti-LIGHT antibody to a subject in need thereof.

Embodiment 15. A method of treating cytokine storm comprising administering an anti-LIGHT antibody to a subject in need thereof.

Embodiment 16. A method of treating a dysregulated hyperimmune response (sometimes referred to as "cytokine storm") comprising administering an anti-LIGHT antibody to a subject in need thereof.

Embodiment 17. A method of treating Acute Respiratory Disease Syndrome (ARDS) comprising administering an anti-LIGHT antibody to a subject in need thereof.

Embodiment 18. The method of any one of embodiments 1 and 2 wherein the anti-LIGHT antibody comprises a heavy chain and a light chain that together comprise one of the following sets of CDR-H1, CDR-H2, CDR-H3, CDR-L1, CDR-L2, and CDR-L3 amino acid sequences:
  (a) SEQ ID NOs: 10, 11, 12, 13, 14, and 15;
  (b) SEQ ID NOs: 16, 17, 18, 19, 20, and 21;
  (c) SEQ ID NOs: 22, 23, 24, 25, 26, and 27;
  (d) SEQ ID NOs: 28, 29, 30, 31, 32, and 33;
  (e) SEQ ID NOs: 34, 35, 36, 37, 38, and 39;
  (f) SEQ ID NOs: 40, 41, 42, 43, 44, and 45;
  (g) SEQ ID NOs: 46, 47, 48, 49, 50, and 51; and
  (h) SEQ ID NOs: 52, 53, 54, 55, 56, and 57.

Embodiment 19. The method of embodiment 4, wherein the first anti-LIGHT antibody comprises a heavy chain and a light chain that together comprise one of the following sets of CDR-H1, CDR-H2, CDR-H3, CDR-L1, CDR-L2, and CDR-L3 amino acid sequences:
  (a) SEQ ID NOs: 10, 11, 12, 13, 14, and 15;
  (b) SEQ ID NOs: 16, 17, 18, 19, 20, and 21;
  (c) SEQ ID NOs: 22, 23, 24, 25, 26, and 27;
  (d) SEQ ID NOs: 28, 29, 30, 31, 32, and 33;
  (e) SEQ ID NOs: 34, 35, 36, 37, 38, and 39;
  (f) SEQ ID NOs: 40, 41, 42, 43, 44, and 45;
  (g) SEQ ID NOs: 46, 47, 48, 49, 50, and 51; and
  (h) SEQ ID NOs: 52, 53, 54, 55, 56, and 57,
and wherein the second anti-LIGHT antibody comprises a heavy chain and a light chain that together comprise any one of the sets of CDR-H1, CDR-H2, CDR-H3, CDR-L1, CDR-L2, and CDR-L3 of (a)-(h) above or SEQ ID NOs: 2, 3, 4, 5, 6, and 7.

Embodiment 20. The method of any one of embodiments 3 and 5-17, wherein the anti-LIGHT antibody that is administered to the subject comprises a heavy chain and a light chain that together comprise one of the following sets of CDR-H1, CDR-H2, CDR-H3, CDR-L1, CDR-L2, and CDR-L3 amino acid sequences:
  (a) SEQ ID NOs: 2, 3, 4, 5, 6, and 7;
  (b) SEQ ID NOs: 10, 11, 12, 13, 14, and 15;
  (c) SEQ ID NOs: 16, 17, 18, 19, 20, and 21;
  (d) SEQ ID NOs: 22, 23, 24, 25, 26, and 27;
  (e) SEQ ID NOs: 28, 29, 30, 31, 32, and 33;
  (f) SEQ ID NOs: 34, 35, 36, 37, 38, and 39;
  (g) SEQ ID NOs: 40, 41, 42, 43, 44, and 45;
  (h) SEQ ID NOs: 46, 47, 48, 49, 50, and 51; and
  (i) SEQ ID NOs: 52, 53, 54, 55, 56, and 57.

Embodiment 21. The method of any one of the preceding embodiments, wherein the antibody comprises the CDR-H1, CDR-H2, CDR-H3, CDR-L1, CDR-L2, and CDR-L3 amino acid sequences of any one of antibodies 1C02, 13H04, 31A10, 1C06, 98C07, 18E04, 42A02, 29C09, 14B09, 117C06, 114F05, or 62C01 described in WO 2015/107331.

Embodiment 22. The method of any one of embodiments 2-21, wherein the condition associated with elevated free LIGHT is coronavirus infection.

Embodiment 23. The method of embodiment 22, wherein the condition associated with elevated free LIGHT is a COVID-19 infection.

Embodiment 24. The method of embodiment 23, wherein the coronavirus infection is a MERS-CoV or SARS-CoV infection.

Embodiment 25. The method of any one of embodiments 2-24, wherein the condition associated with elevated free LIGHT is Crohn's Disease or an inflammatory condition associated with Crohn's Disease.

Embodiment 26. The method of any one of the preceding embodiments, wherein the anti-LIGHT antibody administered comprises a heavy chain and a light chain comprising a CDR-H1, CDR-H2, CDR-H3, CDR-L1, CDR-L2, and CDR-L3 amino acid sequences of SEQ ID NOs: 2, 3, 4, 5, 6, and 7, respectively.

Embodiment 27. The method of any one of the preceding embodiments, wherein a single dose of about 16 mg/kg of the anti-LIGHT antibody is administered.

Embodiment 28. The method of any one of the preceding embodiments, wherein the subject has received, or is currently receiving, an anti-COVID-19 therapy, optionally wherein the therapy is corticosteroids, hydroxychloroquine, and/or remdesivir.

Embodiment 29. The method of embodiment 28, wherein the dose of corticosteroid is considered high dose.

Embodiment 30. The method of any one of the preceding embodiments, wherein the subject is human.

Embodiment 31. The method of any one of the preceding embodiments, wherein the subject has a respiratory disease, optionally caused by a coronavirus infection.

Embodiment 32. The method of any one of the preceding embodiments, wherein the subject has pneumonia.

Embodiment 33. The method of any one of the preceding embodiments, wherein the subject has acute lung injury (ALI).

Embodiment 34. The method of any one of the preceding embodiments, wherein the subject has acute respiratory distress syndrome (ARDS).

Embodiment 35. The method of any one of the preceding embodiments, wherein the subject has a mild coronavirus infection.

Embodiment 36. The method of any one of the preceding embodiments, wherein the subject has a moderate coronavirus infection.

Embodiment 37. The method of any one of the preceding embodiments, wherein the subject has a severe coronavirus infection.

Embodiment 38. The method of any one of the preceding embodiments, wherein the subject is at the Early Infection (Stage I) of a coronavirus infection.

Embodiment 39. The method of any one of the preceding embodiments, wherein the subject is at the Pulmonary Phase (Stage II) of a coronavirus infection.

Embodiment 40. The method of any one of the preceding embodiments, wherein the subject is at the Hyperinflammation Phase (Stage III) of a coronavirus infection.

Embodiment 41. The method of any one of the preceding embodiments, wherein the subject is a pediatric subject.

Embodiment 42. The method of any one of the preceding embodiments, wherein the subject is an adult.

Embodiment 43. A kit for use in a method of any one of embodiments 1-3, 5-18, and 20-42 comprising an anti-LIGHT antibody and reagents for carrying out the method.

Embodiment 44. A kit for use in a method of any one of embodiments 4 and 19 comprising a first anti-LIGHT antibody and a second-LIGHT antibody, wherein the first and the second antibody differ, and reagents for carrying out the method.

Embodiment 45. The kit of embodiment 43, further comprising a solid phase to which the anti-LIGHT antibody is attached.

Embodiment 46. The kit of embodiment 44, further comprising a solid phase to which the first anti-LIGHT antibody is attached.

Embodiment 47. The kit of embodiment 43 or 44, further comprising a solid phase to which free LIGHT derived from the biological sample is attached.

Embodiment 48. A method of determining the amount of free/non-bound Tumor Necrosis Factor Superfamily member 14 (TNFSF14 or LIGHT) in a sample suspected to contain free LIGHT from a subject comprising:
(a) contacting a sample with a capturing molecule for free LIGHT that specifically binds to free LIGHT, but not to bound LIGHT;
(b) incubating the sample to allow the capturing molecule to bind to free LIGHT;
(c) detecting the binding of free LIGHT to the capturing molecule and determining the amount of free LIGHT in the sample.

Embodiment 49. The method of embodiment 48, wherein the capturing molecule is an antibody, optionally wherein the antibody comprises an anti-LIGHT antibody comprising a heavy chain and a light chain that together comprise one of the following sets of CDR-H1, CDR-H2, CDR-H3, CDR-L1, CDR-L2, and CDR-L3 amino acid sequences:
(a) SEQ ID NOs: 10, 11, 12, 13, 14, and 15;
(b) SEQ ID NOs: 16, 17, 18, 19, 20, and 21;
(c) SEQ ID NOs: 22, 23, 24, 25, 26, and 27;
(d) SEQ ID NOs: 28, 29, 30, 31, 32, and 33;
(e) SEQ ID NOs: 34, 35, 36, 37, 38, and 39;
(f) SEQ ID NOs: 40, 41, 42, 43, 44, and 45;
(g) SEQ ID NOs: 46, 47, 48, 49, 50, and 51; and
(h) SEQ ID NOs: 52, 53, 54, 55, 56, and 57.

Embodiment 50. The method of any one of embodiments 48-49, wherein the capturing molecule specifically binds to free LIGHT, but not to a LIGHT/DcR3 complex, or LIGHT/HVEM complex, or LIGHT/LTβR complex.

Embodiment 51. The method of any one of embodiments 48-50, wherein the capturing molecule specifically binds to free LIGHT at the site at which LIGHT binds to DcR3 or in the vicinity of the site at which LIGHT binds to DcR3.

Embodiment 52. The method of embodiment 51, wherein the capturing molecule specifically binds to free LIGHT at a site at which LIGHT binds to DcR3.

Embodiment 53. The method of any one of embodiments 48-52, wherein a detection molecule is provided, wherein the detection molecule binds to LIGHT at site that is different from the site at which the capturing molecule binds.

Embodiment 54. The method of any one of embodiments 48-53, further comprising comparing the amount of free and total LIGHT in the sample.

Embodiment 55. The method of any one of embodiments 48-54, wherein the capturing molecule is an antibody.

Embodiment 56. The method of any one of embodiments 48-55, wherein the capturing molecule is an antibody chosen from monoclonal, polyclonal, chimeric, single chain, bispecific or bi-effective, simianized, human and humanized antibodies.

Embodiment 57. The method of any one of embodiments 48-56, wherein the capturing antibody is monoclonal antibody.

Embodiment 58. The method of any one of embodiments 48-57, wherein the capturing antibody is bound to a support (e.g., nanoparticle in Simoa platform).

Embodiment 59. The method of any one of embodiments 48-58, wherein the capturing antibody is Enzo ALX-804-841-C100.

Embodiment 60. The method of any one of embodiments 48-59, wherein the detection molecule is an antibody.

Embodiment 61. The method of any one of embodiments 48-60, wherein the detection molecule is monoclonal antibody.

Embodiment 62. The method of any one of embodiments 48-61, wherein the capturing antibody is Enzo ALX-804-841-C100 and the detection antibody is ProSci RF16062.

Embodiment 63. The method of any one of embodiments 48-62, wherein said sample is serum, plasma, saliva, or stool.

Embodiment 64. The method according to any one of embodiments 48-63, wherein said sample is a serum sample.

Embodiment 65. A method of treating Crohn's Disease or an inflammatory condition associated with Crohn's Disease, comprising administering an anti-LIGHT antibody to a subject in need thereof, wherein the anti-LIGHT antibody comprises a heavy chain and a light chain that together comprise one of the following sets of CDR-H1, CDR-H2, CDR-H3, CDR-L1, CDR-L2, and CDR-L3 amino acid sequences:
(a) SEQ ID NOs: 2, 3, 4, 5, 6, and 7;
(b) SEQ ID NOs: 10, 11, 12, 13, 14, and 15;
(c) SEQ ID NOs: 16, 17, 18, 19, 20, and 21;
(d) SEQ ID NOs: 22, 23, 24, 25, 26, and 27;
(e) SEQ ID NOs: 28, 29, 30, 31, 32, and 33;
(f) SEQ ID NOs: 34, 35, 36, 37, 38, and 39;
(g) SEQ ID NOs: 40, 41, 42, 43, 44, and 45;
(h) SEQ ID NOs: 46, 47, 48, 49, 50, and 51; and
(i) SEQ ID NOs: 52, 53, 54, 55, 56, and 57.

Embodiment 66. The method of embodiment 25 or 65, wherein a dose of 1.0 mg/kg of the anti-LIGHT antibody is administered every 14 days.

Embodiment 67. The method of embodiment 25 or 65, wherein a dose of 3.0 mg/kg of the anti-LIGHT antibody is administered every 14 days.

Embodiment 68. The method of any one of embodiments 65-67, wherein the subject is a human.

Embodiment 69. The method of any one of embodiments 65-68, wherein the subject is an adult.

Embodiment 70. The method of any one of embodiments 65-69, wherein the subject has failed treatment with an approved therapeutic dose of an anti-TNFα monoclonal antibody treatment with either no initial response or an initial response to induction with subsequent lost response.

Embodiment 71. The method of any one of embodiments 65-70, wherein administration of the anti-LIGHT antibody reduces the subject's CDAI score.

Embodiment 72. The method of any one of embodiments 65-71, wherein administration of the anti-LIGHT antibody decreases the subject's SES-CD score.

Embodiment 73. The method of any one of embodiments 65-72, wherein administration of the anti-LIGHT antibody increases the subject's IBD-Q score.

Embodiment 74. The method of any one of embodiments 3-24 and 26-42, wherein administration of the anti-LIGHT antibody reduces serum free-LIGHT levels in the subject by 85% or more.

Embodiment 75. The method of embodiment 74, wherein the reduction in serum free-LIGHT levels occurred in less than 5 days after administration of the anti-LIGHT antibody.

Embodiment 76. The method of embodiment 74, wherein the reduction in serum free-LIGHT levels occurred in about 1 day after administration of the anti-LIGHT antibody.

Embodiment 77. The method of any one of embodiments 3-24, 26-42, and 74-76 wherein administration of the anti-LIGHT antibody reduces the subject's risk of mortality by equal to or greater than 50% at 60 days after administration.

Embodiment 78. The method of any one of embodiments 3-24, 26-42, and 74-76, wherein administration of the anti-LIGHT antibody reduces the subject's risk of mortality by equal to or greater than 50% at 28 days after administration.

Embodiment 79. The method of any one of embodiments 3-24, 26-42, and 74-78, where the subject is 60 years of age or older.

Embodiment 80. The method of embodiment 79, wherein administration of the anti-LIGHT antibody shortens the length of the subject's hospital stay compared to subjects receiving standard of care treatment.

Embodiment 81. The method of any one of embodiments 3-24, 26-42, and 74-80, wherein administration of the anti-LIGHT antibody reduces the subject's risk of respiratory failure.

Embodiment 82. The method of any one of embodiments 3-42, 65-73, and 77-81, wherein administration of the anti-LIGHT antibody reduces serum free-LIGHT levels in the subject.

Embodiment 83. Use of an anti-LIGHT antibody in the manufacture of a medicament for treating a condition associated with elevated free LIGHT.

Embodiment 84. A composition comprising an anti-LIGHT antibody for use as a medicament in the treatment of a condition associated with elevated free LIGHT.

Embodiment 85. A composition comprising an anti-LIGHT antibody for use in treating a condition associated with elevated free LIGHT.

Embodiment 86. The use or composition for use according to any one of embodiments 81-83, wherein the condition associated with elevated free LIGHT is one or more of:
a. inflammation, optionally wherein the inflammation is hyperinflammation;
b. immune dysregulation that leads to multisystem organ failure;
c. acute lung injury (ALI), optionally wherein the ALI is associated with a bacterial or viral infection, including coronavirus infection;
d. acute respiratory distress syndrome (ARDS), optionally wherein the ARDS is associated with a bacterial or viral infection, including coronavirus infection;
e. cytokine storm that drives tissue injury and vascular permeability;
f. post-infection pulmonary fibrosis;
g. pneumonia, optionally wherein the pneumonia is associated with a bacterial or viral infection, including coronavirus infection;
h. Crohn's Disease or an inflammatory condition associated with Crohn's Disease; or
i. COVID-19 infection.

Embodiment 87. The use or composition for use according to any one of embodiments 83-86, wherein the anti-LIGHT antibody comprises a heavy chain and a light chain that together comprise one of the following sets of CDR-H1, CDR-H2, CDR-H3, CDR-L1, CDR-L2, and CDR-L3 amino acid sequences:
(a) SEQ ID NOs: 2, 3, 4, 5, 6, and 7;
(b) SEQ ID NOs: 10, 11, 12, 13, 14, and 15;
(c) SEQ ID NOs: 16, 17, 18, 19, 20, and 21;
(d) SEQ ID NOs: 22, 23, 24, 25, 26, and 27;
(e) SEQ ID NOs: 28, 29, 30, 31, 32, and 33;
(f) SEQ ID NOs: 34, 35, 36, 37, 38, and 39;
(g) SEQ ID NOs: 40, 41, 42, 43, 44, and 45;
(h) SEQ ID NOs: 46, 47, 48, 49, 50, and 51; and
(i) SEQ ID NOs: 52, 53, 54, 55, 56, and 57.

BRIEF DESCRIPTION OF THE DRAWINGS

FIG. 1 shows capture of free LIGHT (i.e. DCR-free LIGHT, active LIGHT) with candidate antibody pair (capture antibody: Enzo ALX-804-841-C100, detection antibody: ProSci RF16062; specific epitopes are not detailed for these antibodies), with linearity conducted at 1:10, 1:20, and 1:40 dilution. Simoa™ ultra-high sensitive assay (Myriad RBM) was used to detect and measure free LIGHT with high sensitivity, using Quanterix's fully automated immunoassay platform: Simoa HD-1 Analyzer and single molecule array (Simoa) technology. All incubations take place at room temperature inside the Simoa HD-1 analyzer. Capture antibody conjugated paramagnetic beads were incubated with standards, samples or controls and biotinylated detection antibodies. The beads were then washed and incubated with streptavidin-ß-galactosidase (SßG). After the final wash, the beads were loaded into the Simoa Disc with enzyme substrate, resorufin ß-galactopyranoside (RGP). The fluorescence signals are compared to the standard curve and the quantity of LIGHT Free is determined for each sample. After screening anti-LIGHT antibodies in pairs for sandwich immunoassay-based detection of free LIGHT, assays with one candidate pair were performed to test for linearity and specificity.

FIG. 2A-B shows capture of free LIGHT with candidate pair, with linearity conducted at 1:10, 1:20, 1:40, 1:80 dilution, shown as a table in FIG. 2A and as a graph in FIG. 2B. The same assay described in FIG. 1 was performed at different dilutions.

FIG. 3 shows DcR3 interference of the capture of free LIGHT was tested on the free LIGHT detecting candidate pair (Enzo ALX-804-841-C100—ProSci RF16062 (capture—detection)). A diluent containing free LIGHT was used, rather than native free LIGHT in a serum or plasma sample. DcR3 spiked concentration was 10,000 ng/ml and 11 additional lower concentrations. Signal inhibition value was calculated as a signal reduction (MFI) for the Enzo/ProSci pair.

FIG. 4A-C show comparison of DcR3 interference of free LIGHT detecting antibody pairs in spiked and unspiked samples. FIG. 4A: A spike and recovery experiment was performed to assess DcR3 (10 µg/mL) interference on the candidate pair (Enzo ALX-804-841-C100—ProSci RF16062 (capture—detection)). Serum and plasma samples were incubated with (spiked) and without (unspiked) 150 µg/mL of free LIGHT (in the form of LIGHT standard recombinant antigen). Said spiked and unspiked samples were incubated with DcR3. The % recovery signal was calculated compared to the control with no interference based on the MFI. The % recovery signal with the interference is divided by the signal of the control. The signal inhibition value was calculated for unspiked serum 1 (which had the most significant reduction). The signal inhibition value was calculated for unspiked serum 1 (which had the most significant reduction). 78% represents the reduction in signal, which is related (100%-% recovery). That is, Serum 1's DcR3 recovery is 22%, representing a 78% reduction in signal, and the anti-LIGHT antibody recovery is 15%, which is 85% reduction in signal. In addition, in the group of LIGHT (150 µg/ml) spiked samples (lower panel), sample serum 1 demonstrates 92% inhibition (8% recovery). FIG. 4B: Another spike and recovery experiment with the same parameters was performed to assess DcR3 interference on a different free LIGHT detecting candidate pair (ProSci RF16062—LSBio LS-C133566-100 (capture—Detection)). FIG. 4C: Graph characterizing DcR3 interference with recovery for each candidate pair in native free LIGHT and spiked free LIGHT samples. The relatively low % recovery signal in the native free LIGHT sample for the Enzo ALX-804-841-C100—ProSci RF16062 candidate pair indicated that the pair binds native free LIGHT. In contrast, the relatively little DcR3 interference with % recovery signal for the ProSci RF16062—LSBio LS-C133566-100 candidate pair indicates the pair does not as effectively bind native free LIGHT, even though both candidate pairs bound to non-native LIGHT standard recombinant antigen to about the same degree.

DETAILED DESCRIPTION OF THE INVENTION

Figure 2B:
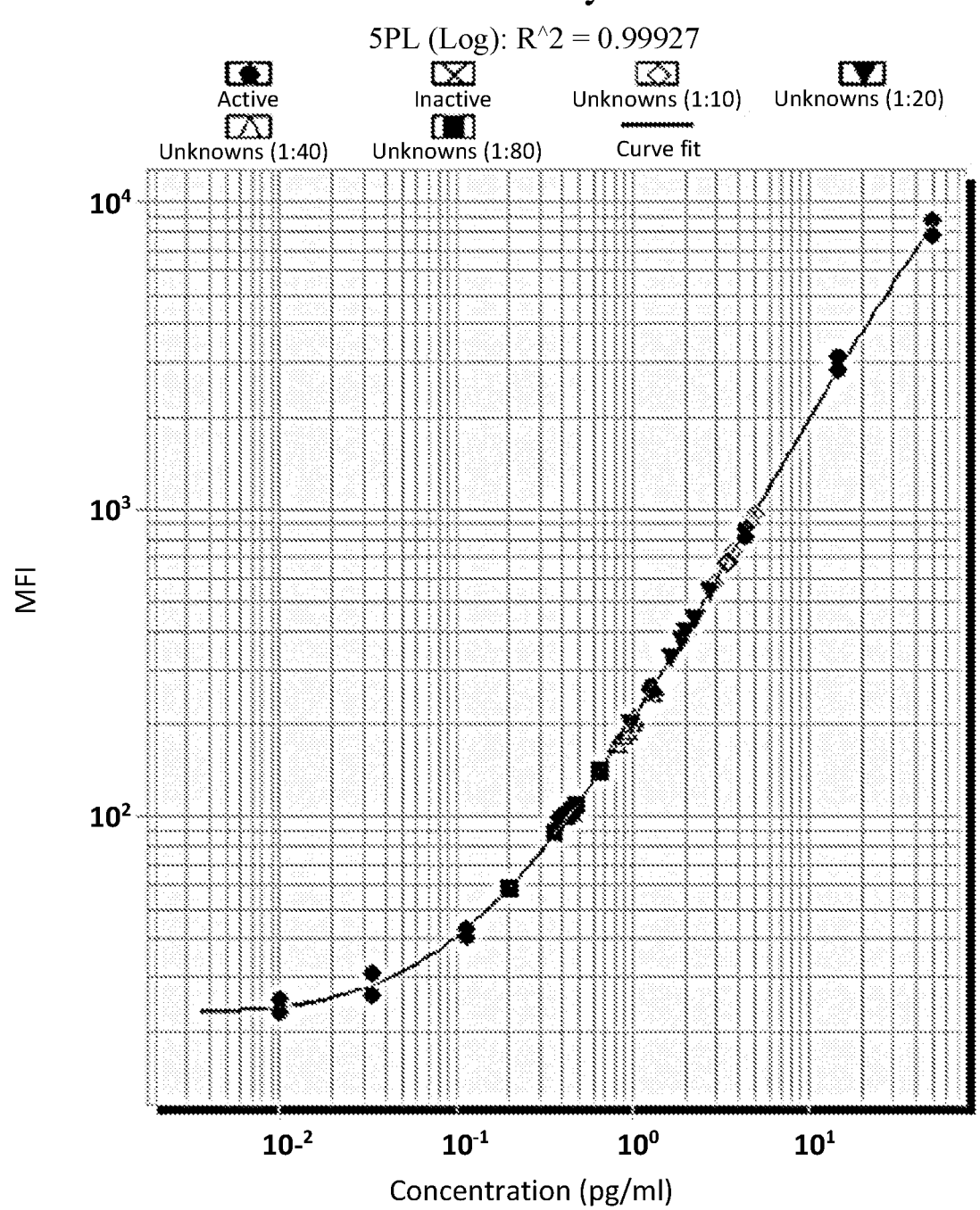

The following definitions are provided to facilitate an understanding of the invention. They are not intended to limit the invention in any way.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an "isolated," or "biologically pure" molecule is a compound that has been removed from its natural milieu. As such, the terms "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

A "coronavirus," "corona respiratory virus," or "CoV" are used interchangeably herein to refer to a virus belonging to the family Coronaviridae. Coronaviruses are enveloped, positive-sense RNA viruses of approximately 31 Kb, making these viruses the largest known RNA viruses. Coronaviruses infect a variety of host species, including humans and several other vertebrates. These viruses predominantly cause respiratory and intestinal tract infections and induce a wide range of clinical manifestations. In general, coronaviruses can be classified into low pathogenic CoVs (including human CoVs (hCoVs)) and highly pathogenic CoVs, such as severe acute respiratory syndrome CoV (SARS-CoV) and Middle East respiratory syndrome CoV (MERS-CoV). Low pathogenic hCoV infect upper airways and cause seasonal mild to moderate cold-like respiratory illnesses in healthy individuals. In contrast, the highly pathogenic hCoVs (pathogenic hCoV) infect the lower respiratory tract and cause severe pneumonia, which sometimes leads to fatal acute lung injury (ALI) and acute respiratory distress syndrome (ARDS), resulting in high morbidity and mortality. SARS-CoV2 is a type of coronavirus. A coronavirus infection as used herein includes any of the above, if associated with coronavirus. "COVID-19 infection" used herein may also refer to a condition or disease caused by SARS-CoV2.

An "acute lung injury" or "ALI" herein refers to an acute lung disease with bilateral pulmonary infiltrate in a chest radiograph consistent with the presence of edema and no clinical evidence of left atrial hypertension; or (if measured) a pulmonary wedge pressure of 18 mmHg or less. Additionally, the ratio of arterial oxygen to the fraction of inspired oxygen (PaO2/FiO2) must be 300 mmHg or less, regardless of the level of positive end-expiratory pressure (PEEP).

"Acute respiratory distress syndrome" or "ARDS" herein refers to the most severe form of ALI, defined by a ratio of arterial oxygen to fraction of inspired oxygen of 200 mmHg or less. The term ARDS is often informally used interchangeably with ALI, but by strict criteria, ARDS should be reserved for the most severe form of the disease.

"LIGHT" or "TNFSF 14" herein refers to a specific member protein of the tumor necrosis factor superfamily that is expressed by activated T cells, monocytes-macrophages and additional types of antigen presenting cells. "LIGHT" is an acronym for "homologous to Lymphotoxin, exhibits Inducible expression and competes with HSV Glycoprotein D for binding to HVEM (herpesvirus entry mediator), a receptor expressed on T lymphocytes."

"Free LIGHT" or "free (active) LIGHT" herein refers to non-bound form LIGHT (e.g., LIGHT bound to DcR3), which is the active form of LIGHT. In humans, free LIGHT is neutralized (inactivated) by DcR3, a unique soluble member of the TNFR superfamily, which binds LIGHT in high affinity and inhibits its interactions with two TNF receptors, HVEM and LTβR. "Bound LIGHT," or the like, refers to LIGHT that is bound to a natural ligand, optionally wherein the natural ligand is HVEM, LTβR, or DcR3. "Total LIGHT," or the like, refers to the total amount of free LIGHT and bound LIGHT.

"Elevated free LIGHT" as used herein refers to a level of free LIGHT detected in a subject that is higher than a normal control. The normal control can be determined by those of skill in the art as applicable to the particular situation. In some instances, the normal control is an industry standard agreed upon by those of skill as being a level or range of levels that is typical of an individual without a LIGHT-associated condition. In some instances, the normal control is a reference level of LIGHT from the same individual taken at a time point, and whether the subject has elevated LIGHT is determined based on a sample from that same individual taken at a different, typically later, time point.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. As used herein, the term refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, human antibodies, and antibodies of various species such as mouse, cynomolgus monkey, etc.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "heavy chain variable region" refers to a region comprising a heavy chain complementary determining region (CDR) 1, framework region (FR) 2, CDR2, FR3, and CDR3 of the heavy chain. In some embodiments, a heavy chain variable region also comprises at least a portion of an FR1 and/or at least a portion of an FR4. In some embodiments, a heavy chain CDR1 corresponds to Kabat residues 31 to 35; a heavy chain CDR2 corresponds to Kabat residues 50 to 65; and a heavy chain CDR3 corresponds to Kabat residues 95 to 102. See, e.g., Kabat Sequences of Proteins of Immunological Interest (1987 and 1991, NIH, Bethesda, Md.).

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence. The term "light chain variable region" refers to a region comprising a light chain CDR1, FR2, HVR2, FR3, and HVR3. In some embodiments, a light chain variable region also comprises an FR1 and/or an FR4. In some embodiments, a light chain CDR1 corresponds to Kabat residues 24 to 34; a light chain CDR2 corresponds to Kabat residues 50 to 56; and a light chain CDR3 corresponds to Kabat residues 89 to 97. See, e.g., Kabat Sequences of Proteins of Immunological Interest (1987 and 1991, NIH, Bethesda, Md.).

A "chimeric antibody" refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, an scFv, a (Fab)$_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The terms "inhibition" or "inhibit" refer to a decrease or cessation of any event (such as protein ligand binding) or to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. It is not necessary that the inhibition or reduction be complete. For example, in certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

"Sample" or "subject sample" or "biological sample" generally refers to a sample which may be tested for a particular molecule. Samples may include but are not limited to cells, body fluids, including blood, serum, plasma, urine, saliva, stool, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP containing nucleic acids described herein or their encoded proteins. Agents are evaluated for potential biological activity by inclusion in screening assays described hereinbelow.

A "subject" can be mammalian. In any of the embodiments involving a subject, the subject can be human. In any of the embodiments involving a subject, the subject can be a cow, pig, monkey, sheep, dog, cat, fish, or poultry.

A "pediatric" subject herein is a human of less than 18 years of age, whereas an "adult" subject is 18 years or older.

"Treatment" or "treat" refers to both therapeutic treatment and prophylactic or preventative measures. Those in need of treatment include those already with the disorder as well as those prone to have the disorder or those in which the disorder is to be prevented. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "effective amount" or "therapeutically effective amount" refers to an amount of a drug effective for treatment of a disease or disorder in a subject, such as to partially or fully relieve one or more symptoms. In some embodiments, an effective amount refers to an amount effective, at dosages and for periods of time necessary, to achieve the desired therapeutic or prophylactic result.

Identification of Biomarker LIGHT

LIGHT (TNFSF14) is an important regulatory cytokine, which serves as critical factor in orchestrating a cytokine storm and pulmonary failure associated with pathogen-mediated infection, including viral and bacterial infections including coronavirus (e.g., COVID-19).

In some embodiments, methods for detecting free (active) LIGHT in a human subject are provided. In some embodiments, the subject's biological sample (e.g., serum) is analyzed for free LIGHT. In some embodiments, the results provide a basis for understanding whether an anti-LIGHT therapy may be provided and will be effective. For instance, if an elevated level of free LIGHT (e.g., a level of free LIGHT above what is expected, for example, using a normal control) then the subject may be diagnosed with a condition associated with elevated free LIGHT and/or be deemed to be a suitable candidate for treatment with an anti-LIGHT antibody. In some embodiments, the anti-LIGHT antibody is an antibody neutralizing LIGHT. In some embodiments, methods for detecting free (active) LIGHT in a subject's biological sample (e.g., serum) are provided, wherein the results provide a basis for understanding whether an anti-LIGHT therapy may be provided and will be effective. In some embodiments, detection of free LIGHT above a normal control indicates that an anti-LIGHT therapy may be provided and effective.

In some embodiments, the condition associated with elevated free LIGHT with which the subject may be diagnosed is Crohn's Disease or an inflammatory condition associated with Crohn's Disease. In some embodiments, the condition associated with elevated free LIGHT with which the subject may be diagnosed is a coronavirus infection. In some embodiments, the coronavirus infection is a moderate or a severe coronavirus infection. In some embodiments, conditions associated with elevated free LIGHT include any one or more of inflammation, optionally wherein the inflammation is hyperinflammation, immune dysregulation that leads to multisystem organ failure, acute lung injury (ALI), optionally wherein the ALI is associated with a bacterial or viral infection, including coronavirus infection, acute respiratory distress syndrome (ARDS), optionally wherein the ARDS is associated with a bacterial or viral infection, including coronavirus infection, cytokine storm that drives tissue injury and vascular permeability, post-infection pulmonary fibrosis, and pneumonia, optionally wherein the pneumonia is associated with a bacterial or viral infection, including coronavirus infection. In some embodiments, the condition associated with elevated free LIGHT is mild, moderate, or severe coronavirus infection, optionally wherein the coronavirus infection is a COVID-19 infection. In some embodiments, the COVID-19 infection is associated with ALI or ARDS in the subject. In some embodiments, the COVID-19 infection is associated with cytokine storm that drives tissue injury and vascular permeability in the lungs and post-infection pulmonary fibrosis. In some embodiments, the coronavirus infection is MERS-CoV, SARS-CoV, or SARS-CoV2/COVID-19.

In some embodiments, methods for diagnosing a condition associated with elevated free LIGHT in a subject are provided, wherein the level of free (active) LIGHT in a biological sample is detected. If the levels are above a normal control, then the subject is diagnosed as having a condition associated with elevated free LIGHT. In some embodiments, the condition associated with elevated free LIGHT to be detected is Crohn's Disease or an inflammatory condition associated with Crohn's Disease. In some embodiments, the condition associated with elevated free LIGHT to be detected is a virus infection. In some embodiments, the condition associated with elevated free LIGHT is a coronavirus infection. In some embodiments, the condition associated with elevated free LIGHT to be detected is a moderate or a severe coronavirus infection. In some embodiments, the condition associated with elevated free LIGHT to be detected is a mild, moderate, or severe COVID-19 infection. In some embodiments, the COVID-19 infection is associated with ALI or ARDS in the subject. In some embodiments, the coronavirus infection is MERS-CoV or SARS-CoV.

In some embodiments, methods for detecting free LIGHT in a biological sample from a subject may be conducted with a biological sample comprising blood, urine, serum, plasma, feces, or gastric lavage bodily fluid samples, or cell samples such as white blood cells or mononuclear cells.

In some embodiments, the method of detecting free (active) LIGHT in subject is performed by:
(a) contacting the biological sample with at least one anti-LIGHT antibody;
(b) incubating the biological sample to allow the anti-LIGHT antibody to bind to free LIGHT; and
(c) determining the presence of complexes formed between the anti-LIGHT antibody and free LIGHT in the biological sample.

This method can further comprise the step of diagnosing the subject as having a condition associated with elevated free LIGHT and/or administering an anti-LIGHT antibody.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (MA), competition assay, and sandwich method.

An indicator moiety, or label group, can be attached to the subject antibodies and is selected to meet the needs of various uses of the method which are often dictated by the availability of assay equipment and compatible immunoassay procedures. Appropriate labels include, without limitation, radionuclides (for example 125I, 131I, 35S, 3H, or 32P), enzymes (for example, alkaline phosphatase, horseradish peroxidase, luciferase, or β-galactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif).

General techniques to be used in performing the various immunoassays noted above are known to those of ordinary skill in the art.

ELISA assays are generally known to the skilled artisan and can be designed to determine serum LIGHT levels. In one exemplary embodiment, blood is collected, and the serum is isolated. If no kit is available, an ELISA can be developed using plates that are pre-coated with capture antibody specific for the LIGHT one is measuring. The plate is next incubated at room temperature for a period of time before washing. Enzyme-anti-LIGHT antibody conjugate is added and incubated. Unbound antibody conjugate is removed, and the plate washed before the addition of the chromogenic substrate solution that reacts with the enzyme. The plate is read on an appropriate plate reader at an absorbance specific for the enzyme and substrate used.

The competition method compares the competitive binding of an antigen in a sample and a known amount of a labeled antigen to the monoclonal antibody of the present invention. To carry out an immunological assay based on the competition method, a sample containing an unknown amount of the target antigen is added to a solid substrate to which the monoclonal antibody of the present invention is coated physically or chemically by known means, and the reaction is allowed to proceed. Simultaneously, a predetermined amount of the pre-labeled target antigen is added and the reaction is allowed to proceed. After incubation, the solid substrate is washed and the activity of the labeling agent bound to the solid substrate is measured.

In the sandwich method, the target antigen in a sample is sandwiched between the immobilized monoclonal antibody and the labeled monoclonal antibody, then a labeling substrate such as an enzyme is added, substrate color changes are detected, and thereby detecting the presence of the antigen. To carry out an immunological assay based on the sandwich method, for instance, a sample containing an unknown amount of the target antigen is added to a solid substrate to which the monoclonal antibody of the present invention is coated physically or chemically by known means, and the reaction is allowed to proceed. Thereafter, the labeled monoclonal antibody of the invention is added and the reaction is allowed to proceed. After incubation, the solid substrate is washed and the activity of the labeling agent bound to the solid substrate is measured.

In some embodiments, a first antibody is used for a diagnostic and a second antibody is used as a therapeutic. In some embodiments, the first and second antibodies are different. In some embodiments, the first and second antibodies can both bind to the antigen at the same time, by binding to separate epitopes.

Methods of Treating with Anti-LIGHT Antibody

The present invention provides a method of treating subjects having elevated free LIGHT, including subjects having a condition associated with elevated free LIGHT with an anti-LIGHT antibody. In some embodiments, the anti-LIGHT antibody is an antibody neutralizing LIGHT. In some embodiments, the condition associated with elevated free LIGHT is a coronavirus infection, including COVID-19. In some embodiments, the condition associated with elevated free LIGHT is Crohn's Disease or an inflammatory condition associated with Crohn's Disease. The treatment can be done with or without a diagnostic test for detecting elevated free LIGHT in a subject's sample.

In some embodiments, a biological sample from the subject is first tested for the presence and level of free LIGHT in a threshold step before the subject is treated. In such embodiments, the method of treating comprises contacting a biological sample from a subject with at least one first anti-LIGHT antibody, incubating the biological sample to allow the anti-LIGHT antibody to bind to free LIGHT, determining the presence of complexes formed between the anti-LIGHT antibody and free LIGHT in the biological sample, and finally, based on the positive results of the detecting step and a finding of elevated free LIGHT, administering to the subject an effective amount of a second anti-LIGHT antibody, wherein the first and the second antibody differ.

In some embodiments, the subject is treated without a threshold testing step. In such cases, it may have been predetermined that the subject could benefit from an anti-LIGHT therapy or the anti-LIGHT antibody is being administered for prevention. In such embodiments, the method of treating comprises administering to a subject having a condition associated with elevated free LIGHT an effective amount of an anti-LIGHT antibody.

In some embodiments of the method of treating, the condition associated with elevated free LIGHT is Crohn's Disease or an inflammatory condition associated with Crohn's Disease.

In some embodiments of the method of treating, the condition associated with elevated free LIGHT is a coronavirus infection. In some embodiments, the coronavirus infection is a COVID-19 infection. In some embodiments, the subject has a respiratory disease, optionally caused by a virus, bacteria or fungus. In some embodiments, the subject has a respiratory disease caused by coronavirus infection. In some embodiments, the subject has a respiratory disease caused by COVID-19. In some embodiments, the subject has pneumonia. In some embodiments, the subject has acute lung injury (ALI). In some embodiments, the subject has acute respiratory distress syndrome (ARDS). In some embodiments, pneumonia is associated with coronavirus infection. In some embodiments, ALI or ARDS is associated with coronavirus infection. In some embodiments, pneumonia is associated with COVID-19. In some embodiments, the subject has acute lung injury (ALI) associated with COVID-19. In some embodiments, the subject has acute respiratory distress syndrome (ARDS) associated with COVID-19. In some embodiments, the subject has a mild coronavirus infection. In some embodiments, the subject has a moderate coronavirus infection. In some embodiments, the subject has a severe coronavirus infection. In some embodiments, a method of treating severe COVID-19 pneumonia comprising administering an anti-LIGHT antibody to a subject in need thereof is provided. In some embodiments, a method of treating acute inflammatory disease associated with COVID-19 pneumonia comprising administering an anti-LIGHT antibody to a subject in need thereof is provided. In some embodiments, a method of treating respiratory failure associated with COVID-19 pneumonia comprising administering an anti-LIGHT antibody to a subject in need thereof is provided. In some embodiments, a method of treating cytokine storm comprising administering an anti-LIGHT antibody to a subject in need thereof is provided. In some embodiments, a method of treating a dysregulated hyperimmune response (sometimes referred to as "cytokine storm") comprising administering an anti-LIGHT antibody to a subject in need thereof is provided. In some embodiments, a method of treating Acute Respiratory Disease Syndrome (ARDS) comprising administering an anti-LIGHT antibody to a subject in need thereof is provided.

In some embodiments, the administration of the anti-LIGHT antibody suppresses T cell activation. In some embodiments, the administration of the anti-LIGHT antibody suppresses increased expression of cytokines (e.g., a cytokine storm). In some embodiments, the administration of the anti-LIGHT antibody suppresses increased expression of cytokines (e.g., a cytokine storm) that is caused by a viral and/or bacterial infection, e.g., from a coronavirus infection. In some embodiments the administration of the anti-LIGHT antibody prevents or treats cytokine storm caused by a virus and/or bacterial infection, such as by a coronavirus infection. In some embodiments, the cytokine storm can drive tissue injury and vascular permeability in the lungs. Cytokine storm can lead to ARDS and ALI associated with coronavirus (e.g., COVID-19) infection. In some embodiments, the administration of the anti-LIGHT antibody prevents or treats post-infection pulmonary fibrosis, optionally associated with coronavirus infection. In some embodiments, the administration of the anti-LIGHT antibody reduces the subject's risk of mortality or morbidity. In some embodiments, the administration of the anti-LIGHT antibody prevents progression to ARDS in a subject with pneumonia associated with a coronavirus infection (e.g., COVID-19 infection). In some embodiments, the administration of the anti-LIGHT antibody prevents progression of ALI associated with a coronavirus infection, including (e.g., COVID-19 infection) to ARDS. In some embodiments, the administration of the anti-LIGHT antibody prevents or treats ARDS. In some embodiments, the administration of the anti-LIGHT antibody prevents the need for ventilation/intubation of the subject.

The methods of treating in the present invention may be carried out through conventional administration routes, including without limitation, the oral, buccal, sublingual, ocular, topical, parenteral, rectal, intracisternal, intravaginal, intraperitoneal, intravesical, local (e.g., powder, ointment, or drop), or nasal routes. The term "parenteral" includes subcutaneous, intravenous, intramuscular, or infusion. In certain embodiments, it may be appropriate to administer the agent in a continuous infusion or as a subcutaneous injection every day, every two or several days, or once a week, or every several weeks, or once a month, or once every several months, or at a time interval within a range defined by any two of the aforementioned intervals.

In some embodiments, the anti-LIGHT antibody is administered to a subject already receiving another therapy. In the case of a subject with COVID-19, the other therapy may be any therapy approved or being tested to treat or ameliorate a symptom of COVID-19. Such therapies include, but are not limited to, remdesivir, corticosteroids, and hydroxychloroquine. In some embodiments, the other therapy continues (on its normal course) during treatment with the anti-LIGHT antibody. In some embodiments, the other therapy is discontinued during treatment with the anti-LIGHT antibody. In some embodiments, the subject has COVID-19 and is receiving a high dose of corticosteroid and an anti-LIGHT antibody. In some embodiments, subject receiving the combination high dose corticosteroid and anti-LIGHT antibody have better outcomes than those not receiving the combination.

In some embodiments, the dose of anti-LIGHT antibody is about 16 mg/kg with a maximum dose of 1,200 mg. In some embodiments, the dose is a single administration. In some embodiments, the dose is more than a single administration.

In some embodiments, administration of the anti-LIGHT antibody reduces serum free-LIGHT levels in the subject by 85% or more, for example, compared to free-LIGHT levels in the subject prior to administration of the anti-LIGHT antibody or compared to subjects who are not administered the anti-LIGHT antibody. In some embodiments, the reduction in serum free-LIGHT levels in the subject by 85% or more occurs in less than 5 days or less than 1 day after administration of the anti-LIGHT antibody. In some embodiments, the anti-LIGHT antibody administered to the subject reduces the subject's risk of mortality by equal to or greater than 50% at 60 days after administration. In some embodiments, the anti-LIGHT antibody administered to the subject reduces the subject's risk of mortality by equal to or greater than 50% at 28 days after administration. In some embodiments, the subject is 60 years of age or older. In some embodiments, the anti-LIGHT antibody administered to the subject shortens the length of the subject's hospital stay compared to subjects receiving standard of care treatment. In some embodiments, the anti-LIGHT antibody administered to the subject reduces the subject's risk of respiratory failure.

In some embodiments, the anti-LIGHT antibody is administered as a dose of from about 1.0 mg/kg to about 3.0 mg/kg. In some embodiments, the anti-LIGHT antibody is administered as a dose of about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 mg/kg. In some embodiments, the anti-LIGHT antibody is administered every day, every 2 days, every 3 days, every 4 days, every 5 days, every 6 days, every week, every two weeks, every three weeks, or every four weeks. In some embodiments, the anti-LIGHT antibody is administered as a dose of from about 1.0 mg/kg to about 3.0 mg/kg every 14 days. In some embodiments, the anti-LIGHT antibody is administered as a dose of 1.0 mg/kg every 14 days. In some embodiment, the anti-LIGHT antibody is administered as a dose of 3.0 mg/kg every 14 days.

In some embodiments, the anti-LIGHT antibody is administered to a subject who has failed treatment with an approved therapeutic dose of an anti-TNFα monoclonal antibody treatment with either no initial response or an initial response to induction with subsequent lost response.

Treatment of Crohn's Disease

The primary clinical target for CD treatment is the resolution of symptoms. (Shi and Ng, The state of the art on treatment of Crohn's disease, J. Gastroenterol., 2018:53; 989-998). The standard index for assessing symptoms is the Crohn's Disease Activity Index (CDAI), which includes eight variables: the number of liquid stools, the extent of abdominal pain, general well-being, the occurrence of extraintestinal symptoms, the need for antidiarrhea drugs, the presence of abdominal masses, hematocrit, and body weight. (Shi and Ng 2018). Control of symptoms does not appear to significantly alter the natural course of the disease. (Shi and Ng 2018).

Mucosal healing is becoming another target in clinical practice. The Simple Endoscopic Score for Crohn's Disease (SES-CD) is one of the most common endoscopic scoring systems for CD. The SES-CD is scored based on four endoscopic variables (presence and size of ulcers, extent of ulcerated surface, extent of affected surface, and presence and type of narrowing) in the same five segments. An SES-CD score below 2 is regarded as endoscopic remission. A decrease from baseline of at least 50% in an SES-CD score has been used as the definition for endoscopic response. There is currently no set, universal definition for mucosal healing, but the absence of ulceration at ileocolonoscopy has been adopted as the endoscopic endpoint for CD. (Shi and Ng 2018).

A Patient reported outcome is a measurement derived directly from a patient about any aspect of their health status and has the potential to become a treatment endpoint for CD. Several scales have been used to assess patients' perspectives towards the disease, including the Inflammatory Bowel Disease Questionnaire (IBD-Q). (Shi and Ng 2018).

In some embodiments, administration of the anti-LIGHT antibody reduces the subject's CDAI score, for example, compared to the subject's CDAI score prior to administration of the anti-LIGHT antibody or compared to subjects who are not administered the anti-LIGHT antibody. In some embodiments, administration of the anti-LIGHT antibody decreases the subject's SES-CD score, for example, compared to the subject's SES-CD score prior to administration of the anti-LIGHT antibody or compared to subjects who are not administered the anti-LIGHT antibody. In some embodiments, administration of the anti-LIGHT antibody results in the subject's SES-CD score of below 2. In some embodiments, administration of the anti-LIGHT antibody increases the subject's IBD-Q score, for example, compared to the subject's IBD-Q score prior to administration of the anti-LIGHT antibody or compared to subjects who are not administered the anti-LIGHT antibody. In some embodiments, administration of the anti-LIGHT antibody results in the subject's IBD-Q score of 170 or higher. In some embodiments, administration of the anti-LIGHT antibody results in an increase in the subject's IBD-Q score of at least 16 points. In some embodiments, administration of the anti-LIGHT antibody results in an increase in the subject's IBD-Q score of at least 32 points.

Stages of COVID-19 Disease Progression

The stages of COVID-19 Disease Progression are shown in FIG. 1 of Siddiqi, H. K., et al. COVID-19 illness in native and immunosuppressed states: A clinical-therapeutic staging proposal. J Heart Lung Transplant 39(5), 405-407 (2020). The disease can broadly be divided into three stages: Early Infection, Pulmonary Phase, and Hyperinflammation Phase.

Stage I is the viral response phase, Stage III is the host inflammatory response phase, and Stage II is a combination of the two. As patients progress from Early Infection (Stage I) to the Pulmonary Phase (Stage II) at which pulmonary symptoms appear, the host inflammatory response emerges. It is at this point where, in some patients, dysregulation of the inflammatory response occurs. This dysregulation of the inflammatory response may be accompanied by elevated free LIGHT levels in biological fluids, such as serum. This stage, the Pulmonary Phase, is the optimal stage at which to administer an anti-LIGHT antibody to correct this dysregulation and avert cytokine storm and progression to ARDS, which occurs in the Hyperinflammation Phase (Stage III).

Patients in Stage I of COVID-19 are considered to have mild disease. Patients in Stage II of COVID-19 are considered to have mild to moderate disease. Patients in Stage III of COVID-19 are considered to have severe disease.

In some embodiments, the anti-LIGHT antibody is administered to a subject with mild coronavirus (e.g., COVID-19). In some embodiments, the anti-LIGHT antibody is administered during the early infection stage of a coronavirus. In some embodiments, the anti-LIGHT antibody is administered during Stage I of a coronavirus. In some embodiments, the anti-LIGHT antibody is administered while the subject in need thereof has mild constitutional symptoms, a fever >99.6° F., dry cough, diarrhea, or headache. In some embodiments, the subject in need thereof has lymphopenia, increased prothrombin time, increased D-dimer and LDH (mild). In some embodiments, the administration of the anti-LIGHT antibody treats Stage I of a coronavirus. In some embodiments, the administration of the anti-LIGHT antibody prevents progression of the coronavirus to Stage II. Staging refers to FIG. 1 of Siddiqi, H. K., et al. (2020), incorporated herein in its entirety.

In some embodiments, the anti-LIGHT antibody of the method is administered to a subject with moderate coronavirus (e.g., COVID-19). In some embodiments, the anti-LIGHT antibody is administered during the Pulmonary Phase of a coronavirus. In some embodiments, the anti-LIGHT antibody is administered during Stage II of a coronavirus. In some embodiments of the invention, the anti-LIGHT antibody is administered during Stage IIA or Stage IIB of a coronavirus. In some embodiments, the anti-LIGHT antibody is administered while the subject in need thereof is exhibiting shortness of breath or hypoxia. In some embodiments, the anti-LIGHT antibody is administered while the subject in need thereof meets the clinical criteria for ALI. In some embodiments, the subject in need thereof has abnormal chest imaging, transaminitis, or low-normal procalcitonin. In some embodiments, the patient is not ventilated/intubated. In some embodiments, the administration of the anti-LIGHT antibody treats Stage II of a coronavirus. In some embodiments, the administration of the anti-LIGHT antibody prevents progression of the coronavirus to Stage III.

In some embodiments, the anti-LIGHT antibody is administered to a subject with severe coronavirus (e.g., COVID-19). In some embodiments, the anti-LIGHT antibody is administered during the Hyperinflammation Phase of a coronavirus. In some embodiments, the anti-LIGHT antibody is administered during Stage III of a coronavirus. In some embodiments, the anti-LIGHT antibody is administered while the subject in need thereof has ARDS, systemic inflammatory response syndrome (SIRS)/Shock, or Cardiac Failure. SIRS is a complex immune response to insult characterized by widespread inflammation within the body. Both infectious and non-infectious causes of SIRS have been identified. In some embodiments, the patient is ventilated/intubated. In some embodiments, the administration of the anti-LIGHT antibody treats Stage III of a coronavirus.

Anti-LIGHT Antibodies

In some embodiments, an anti-LIGHT antibody is utilized for both detection/diagnostic and therapeutic purposes, as well as in the assays described herein. The anti-LIGHT antibody used for detection or diagnostic purposes is different from the antibody used for therapeutic purposes (even in the same subject).

The anti-LIGHT antibody useful for therapeutic purposes may comprise the CDR sequences of the E1, E13, E63, F19, or F23 antibodies, which are provided in WO 2008/027338 and U.S. Pat. No. 8,058,402 B2, U.S. Pat. No. 8,461,307 B2, and U.S. Pat. No. 8,974,787 B2, each of which is incorporated herein by reference. The anti-LIGHT antibody useful for detection/diagnostic purposes is not that same as that which is used for therapeutic purposes.

In some embodiments, the anti-LIGHT antibody comprises a heavy chain comprising three CDR sequences comprising each of SEQ ID NOs: 2, 3, and 4, respectively. In some embodiments, the anti-LIGHT antibody comprises a light chain comprising three CDR sequences comprising each of SEQ ID NOs: 5, 6, and 7, respectively. In some embodiments, the antibody comprises a heavy chain and a light chain, the heavy chain comprising three CDR sequences comprising each of SEQ ID NOs: 2, 3, and 4, respectively, and the light chain comprising three CDR sequences comprising each of SEQ ID NOs: 5, 6, and 7, respectively.

In some embodiments, the anti-LIGHT antibody comprises a heavy chain variable region sequence comprising SEQ ID NO: 8 or that is at least 85%, at least 90%, at least 95%, at least 98%, or at least 99% identical to SEQ ID NO:8. In some embodiments, the anti-LIGHT antibody comprises a light chain variable region sequence comprising SEQ ID NO:9 or that is at least 85%, at least 90%, at least 95%, at least 98%, or at least 99% identical to SEQ ID NO:9. In some embodiments, the anti-LIGHT antibody comprises a heavy chain comprising SEQ ID NO: 8 or that is at least 85%, at least 90%, at least 95%, at least 98%, or at least 99% identical to SEQ ID NO:8. In some embodiments, the anti-LIGHT antibody comprises a light chain comprising SEQ ID NO:9 or that is at least 85%, at least 90%, at least 95%, at least 98%, or at least 99% identical to SEQ ID NO:9. In some embodiments, the anti-LIGHT antibody comprises both a heavy chain comprising SEQ ID NO: 8 or that is at least 85%, at least 90%, at least 95%, at least 98%, or at least 99% identical to SEQ ID NO:8 and a light chain comprising SEQ ID NO:9 or that is at least 85%, at least 90%, at least 95%, at least 98%, or at least 99% identical to SEQ ID NO:9.

In some embodiments, the anti-LIGHT antibody comprises a heavy chain comprising three CDR sequences comprising each of SEQ ID NOs: 10, 11, and 12, respectively. In some embodiments, the anti-LIGHT antibody comprises a light chain comprising three CDR sequences comprising each of SEQ ID NOs: 13, 14, and 15, respectively. In some embodiments, the antibody comprises a heavy chain and a light chain, the heavy chain comprising three CDR sequences comprising each of SEQ ID NOs: 10, 11, and 12, respectively, and the light chain comprising three CDR sequences comprising each of SEQ ID NOs: 13, 14, and 15, respectively.

In some embodiments, the anti-LIGHT antibody comprises a heavy chain comprising three CDR sequences comprising each of SEQ ID NOs: 16, 17, and 18, respectively. In some embodiments, the anti-LIGHT antibody comprises a light chain comprising three CDR sequences comprising each of SEQ ID NOs: 19, 20, and 21, respectively. In some embodiments, the antibody comprises a heavy chain and a light chain, the heavy chain comprising three CDR sequences comprising each of SEQ ID NOs: 16, 17, and 18, respectively, and the light chain comprising three CDR sequences comprising each of SEQ ID NOs: 19, 20, and 21, respectively.

In some embodiments, the anti-LIGHT antibody comprises a heavy chain comprising three CDR sequences comprising each of SEQ ID NOs: 22, 23, and 24, respectively. In some embodiments, the anti-LIGHT antibody comprises a light chain comprising three CDR sequences comprising each of SEQ ID NOs: 25, 26, and 27, respectively. In some embodiments, the antibody comprises a heavy chain and a light chain, the heavy chain comprising three CDR sequences comprising each of SEQ ID NOs: 22, 23, and 24, respectively, and the light chain comprising three CDR sequences comprising each of SEQ ID NOs: 25, 26, and 27, respectively.

In some embodiments, the anti-LIGHT antibody comprises a heavy chain comprising three CDR sequences comprising each of SEQ ID NOs: 28, 29, and 30, respectively. In some embodiments, the anti-LIGHT antibody comprises a light chain comprising three CDR sequences comprising each of SEQ ID NOs: 31, 32, and 33, respectively. In some embodiments, the antibody comprises a heavy chain and a light chain, the heavy chain comprising three CDR sequences comprising each of SEQ ID NOs: 28, 29, and 30, respectively, and the light chain comprising three CDR sequences comprising each of SEQ ID NOs: 31, 32, and 33, respectively.

In some embodiments, the anti-LIGHT antibody comprises a heavy chain comprising three CDR sequences comprising each of SEQ ID NOs: 34, 35, and 36, respectively. In some embodiments, the anti-LIGHT antibody comprises a light chain comprising three CDR sequences comprising each of SEQ ID NOs: 37, 38, and 39, respectively. In some embodiments, the antibody comprises a heavy chain and a light chain, the heavy chain comprising three CDR sequences comprising each of SEQ ID NOs: 34, 35, and 36, respectively, and the light chain comprising three CDR sequences comprising each of SEQ ID NOs: 37, 38, and 39, respectively.

In some embodiments, the anti-LIGHT antibody comprises a heavy chain comprising three CDR sequences comprising each of SEQ ID NOs: 40, 41, and 42, respectively. In some embodiments, the anti-LIGHT antibody comprises a light chain comprising three CDR sequences comprising each of SEQ ID NOs: 43, 44, and 45, respectively. In some embodiments, the antibody comprises a heavy chain and a light chain, the heavy chain comprising three CDR sequences comprising each of SEQ ID NOs: 40, 41, and 42, respectively, and the light chain comprising three CDR sequences comprising each of SEQ ID NOs: 43, 44, and 45, respectively.

In some embodiments, the anti-LIGHT antibody comprises a heavy chain comprising three CDR sequences comprising each of SEQ ID NOs: 46, 47, and 48, respectively. In some embodiments, the anti-LIGHT antibody comprises a light chain comprising three CDR sequences comprising each of SEQ ID NOs: 49, 50, and 51, respectively. In some embodiments, the antibody comprises a heavy chain and a light chain, the heavy chain comprising three CDR sequences comprising each of SEQ ID NOs: 46, 47, and 48, respectively, and the light chain comprising three CDR sequences comprising each of SEQ ID NOs: 49, 50, and 51, respectively.

In some embodiments, the anti-LIGHT antibody may comprise the CDR sequences of the antibodies, which are described in US2013/0323240 and U.S. Pat. No. 8,524,869 B2, which are incorporated herein by reference. For example, in some embodiments, the anti-LIGHT antibody comprises a heavy chain comprising three CDR sequences comprising each of SEQ ID NOs: 52, 53, and 54, respectively. In some embodiments, the anti-LIGHT antibody comprises a light chain comprising three CDR sequences comprising each of SEQ ID NOs: 55, 56, and 57, respectively. In some embodiments, the antibody comprises a heavy chain and a light chain, the heavy chain comprising three CDR sequences comprising each of SEQ ID NOs: 52, 53, and 54, respectively, and the light chain comprising three CDR sequences comprising each of SEQ ID NOs: 55, 56, and 57, respectively.

In some embodiments, the anti-LIGHT antibody comprises a heavy chain variable region sequence comprising SEQ ID NO:58 or that is at least 85%, at least 90%, at least 95%, at least 98%, or at least 99% identical to SEQ ID NO:58. In some embodiments, the anti-LIGHT antibody comprises a light chain variable region sequence comprising SEQ ID NO:59 or that is at least 85%, at least 90%, at least 95%, at least 98%, or at least 99% identical to SEQ ID NO:59. In some embodiments, the anti-LIGHT antibody comprises a heavy chain comprising SEQ ID NO:58 or that is at least 85%, at least 90%, at least 95%, at least 98%, or at least 99% identical to SEQ ID NO:58. In some embodiments, the anti-LIGHT antibody comprises a light chain comprising SEQ ID NO:59 or that is at least 85%, at least 90%, at least 95%, at least 98%, or at least 99% identical to SEQ ID NO:59. In some embodiments, the anti-LIGHT antibody comprises both a heavy chain comprising SEQ ID NO:58 or that is at least 85%, at least 90%, at least 95%, at least 98%, or at least 99% identical to SEQ ID NO:58 and a light chain comprising SEQ ID NO:59 or that is at least 85%, at least 90%, at least 95%, at least 98%, or at least 99% identical to SEQ ID NO:59.

In some embodiments, the anti-LIGHT antibody may comprise a heavy chain and a light chain together comprising one of the following sets of CDR-H1, CDR-H2, CDR-H3, CDR-L1, CDR-L2, and CDR-L3 sequences described in the sequence listing from US2013/0323240: SEQ ID NOs: 18, 19, 20 and SEQ ID NOs: 38, 41, 42 of US2013/0323240; SEQ ID NOs: 18, 19, 21 and SEQ ID NOs: 39, 41, 42 of US2013/0323240; SEQ ID NOs: 18, 19, 22 and SEQ ID NOs: 40, 41, 42 of US2013/0323240; SEQ ID NOs: 23, 24, 25 and SEQ ID NOs: 43, 44, 45 of US2013/0323240; SEQ ID NOs: 26, 27, 28 and SEQ ID NOs: 46, 47, 48 of US2013/0323240; SEQ ID NOs: 29, 30, 31 and SEQ ID NOs: 49, 50, 51 of US2013/0323240; SEQ ID NOs: 32, 33, 34 and SEQ ID NOs: 52, 53, 54 of US2013/0323240; and SEQ ID NOs: 35, 36, 37 and SEQ ID NOs: 55, 50, 51 of US2013/0323240.

In some embodiments, the anti-LIGHT antibody comprises the CDR sequences of the 19E04, 98C07, 1C02, 1C06, 13H04, 31A10, 98C07, 42A02, 29C02, 14B09, 117C06, 114F05, and 62C01 antibodies described in WO 2015/107331, which is also incorporated by reference herein.

For example, in some embodiments, the anti-LIGHT antibody comprises a heavy chain comprising three CDR sequences comprising each of SEQ ID NOs: 60, 61, and 62, respectively. In some embodiments, the anti-LIGHT antibody comprises a light chain comprising three CDR sequences comprising each of SEQ ID NOs: 63, 64, and 65, respectively. In some embodiments, the antibody comprises a heavy chain and a light chain, the heavy chain comprising three CDR sequences comprising each of SEQ ID NOs: 60, 61, and 62, respectively, and the light chain comprising three CDR sequences comprising each of SEQ ID NOs: 63, 64, and 65, respectively.

In some embodiments, the anti-LIGHT antibody comprises a heavy chain comprising three CDR sequences comprising each of SEQ ID NOs: 66, 67, and 68, respectively. In some embodiments, the anti-LIGHT antibody comprises a light chain comprising three CDR sequences comprising each of SEQ ID NOs: 69, 70, and 71, respectively. In some embodiments, the antibody comprises a heavy chain and a light chain, the heavy chain comprising three CDR sequences comprising each of SEQ ID NOs: 66, 67, and 68, respectively, and the light chain comprising three CDR sequences comprising each of SEQ ID NOs: 69, 70, and 71, respectively.

In some embodiments, the anti-LIGHT antibody comprises a heavy chain comprising three CDR sequences comprising each of SEQ ID NOs: 72, 73, and 74, respectively. In some embodiments, the anti-LIGHT antibody comprises a light chain comprising three CDR sequences comprising each of SEQ ID NOs: 75, 76, and 77, respectively. In some embodiments, the antibody comprises a heavy chain and a light chain, the heavy chain comprising three CDR sequences comprising each of SEQ ID NOs: 72, 73, and 74, respectively, and the light chain comprising three CDR sequences comprising each of SEQ ID NOs: 75, 76, and 77, respectively.

In some embodiments, the anti-LIGHT antibody comprises a heavy chain comprising three CDR sequences comprising each of SEQ ID NOs: 78, 79, and 80, respectively. In some embodiments, the anti-LIGHT antibody comprises a light chain comprising three CDR sequences comprising each of SEQ ID NOs: 81, 82, and 83, respectively. In some embodiments, the antibody comprises a heavy chain and a light chain, the heavy chain comprising three CDR sequences comprising each of SEQ ID NOs: 78, 79, and 80, respectively, and the light chain comprising three CDR sequences comprising each of SEQ ID NOs: 81, 82, and 83, respectively.

Kits and Articles of Manufacture

Any of the aforementioned methods can be implemented via kits for the detection of free LIGHT and/or the diagnosis and/or treatment of a condition associated with elevated free LIGHT, including a viral and/or bacterial infection, such as a coronavirus, including COVID-19. The kit may contain an antibody, one or more non-naturally occurring detectable labels, marker, or reporter, a pharmaceutically acceptable carrier, a physiologically acceptable carrier, instructions for use, a container, a vessel for administration, an assay substrate, or any combination thereof.

In some embodiments, the kit is for use in a method of detecting free LIGHT in a biological sample (as opposed to total or bound LIGHT).

In some embodiments, the kit is for use in a method of detecting free LIGHT in a biological sample from a subject having or suspected of having coronavirus infection, ALI, ARDS, or pulmonary fibrosis.

In some embodiments, the kit is for use in a method of detecting free LIGHT in a biological sample from a subject having or suspected of having Crohn's Disease or an inflammatory condition associated with Crohn's Disease.

In some embodiments, the kit is for use in method of detecting elevated free LIGHT in a biological sample from a subject, optionally wherein the subject is suspected of having a coronavirus infection and also for treating the subject after diagnosis by administering an anti-LIGHT antibody in an effective amount.

In some embodiments, the kit for use in one of the above methods is suitable for use in a subject with mild, moderate, or severe Crohn's Disease or a mild, moderate, or severe inflammatory condition associated with Crohn's Disease.

In some embodiments, the kit for use in one of the above methods is suitable for a subject with a mild, moderate, or severe coronavirus infection. In some embodiments, the mild, moderate, or severe coronavirus infection is a COVID-19 infection. In some embodiments, the coronavirus (including COVID-19) infection is associated with respiratory disease. In some embodiments, the coronavirus (including COVID-19) infection is associated with ALI or ARDS.

In some embodiments, the kit for use in a method of detecting and/or treating comprises a solid phase to which the anti-LIGHT antibody reagent is attached. In some embodiments, the kit for use in a method of detecting and/or treating comprises a solid phase to which free LIGHT derived from the biological sample will be attached.

The solid phase to be used in the kits of the present invention includes, but is not limited, to microplates, magnetic particles, filter papers for immunochromatography, polymers such as polystyrene, glass beads, glass filters and other insoluble carriers. In one embodiment, a solid substrate containing many compartments or regions has at least one compartment coated with antibodies of the invention.

The kits of the invention may also include a further component to the diagnostic agent, the anti-LIGHT antibody. The further component may include, but is not limited, to enzymes for labeling, substrates therefor, radioisotopes, light-reflecting substances, fluorescent substances, colored substances, buffer solutions, and plates, and those mentioned hereinabove.

Free LIGHT Detection Assays

Disclosed are assays, which are methods for detecting and measuring free LIGHT in a sample suspected to contain free LIGHT from a subject. Such methods may use antibody pairs for sandwich immunoassay in which free LIGHT from a sample is captured by capture antibodies coating, e.g., paramagnetic beads and a detection antibody further binds to the captured free LIGHT. A labeling enzyme conjugate such as streptavidin-ß-galactosidase (SßG), is then added and binds to the detection antibodies. Finally, an enzyme substrate is added to yield fluorescence intensities that can correlate with the presence and amount of free LIGHT in the sample.

In some embodiments, a sample suspected of containing free LIGHT is contacted with a capturing molecule for free LIGHT that specifically binds to free LIGHT, but not to bound LIGHT, and is incubated to allow the capturing molecule to bind to free LIGHT. Such embodiments further entail detecting the binding of free LIGHT to the capturing molecule and determining the amount of free LIGHT in the sample. The capturing molecule may be, but need not be, an antibody. In some embodiments, bound LIGHT refers to LIGHT bound to a complex. In some embodiments, bound LIGHT is LIGHT bound to a complex with DcR3. In some embodiments, bound LIGHT is LIGHT that is neutralized or inactivated by DcR3. In some embodiments, bound LIGHT is LIGHT bound to either of its TNF receptors, HVEM and LTβR. In some embodiments, LIGHT bound to a complex comprises LIGHT bound to DcR3 or an anti-LIGHT antibody.

In some embodiments, the capturing molecule specifically binds to free LIGHT, but not to a LIGHT/DcR3 complex. In some embodiments, the capturing molecule specifically binds to free LIGHT at the site at which free LIGHT binds to DcR3 or in the vicinity of the site at which free LIGHT binds to DcR3 such that, for example, LIGHT cannot simultaneously bind to the capturing molecule and to DcR3. In some embodiments, the capturing molecule specifically binds to free LIGHT at a site at which LIGHT binds to DcR3. In some embodiments, the capturing molecule specifically binds to free LIGHT at the site or in the vicinity of the site at which free LIGHT binds to either of its TNF receptors, HVEM and LTβR. In some embodiments, the capturing molecule specifically binds to free LIGHT at the site at which free LIGHT binds to either of its TNF receptors, HVEM and LTβR.

In some embodiments of the methods for detecting and measuring free LIGHT in a sample suspected to contain free LIGHT from a subject, the sample is not only contacted with a capturing molecule, but also with a detection molecule. Such embodiments further entail incubating the sample to allow the capturing molecule and the detection molecule to bind to free LIGHT. Such embodiments further entail detecting the binding of free LIGHT to the capturing molecule and determining the amount of free LIGHT in the sample. In some embodiments, the binding of free LIGHT to the detection molecule is also detected. In some embodiments, the detection molecule binds to a different site of free LIGHT than the capture molecule.

In some embodiments of the methods for detecting and measuring free LIGHT in a sample suspected to contain free LIGHT from a subject, the methods further entail comparing the amount of free and amount of total LIGHT in the sample.

In some embodiments, the capturing molecule is an antibody. In some embodiments, the capturing molecule is an antibody chosen from monoclonal, polyclonal, chimeric, single chain, bispecific or bi-effective, simianized, human, and humanized antibodies. In some embodiments, the capturing antibody is a monoclonal antibody. In some embodiments, the capturing antibody is bound to a support (e.g., nanoparticle in Simoa platform). In some embodiments, the capturing antibody is ProSci RF16062.

In some embodiments, the detection molecule is an antibody. In some embodiments, the detection molecule is a monoclonal antibody. In some embodiments, the capturing antibody is ProSci RF16062. In some embodiments, the capturing antibody is Enzo ALX-804-841-C100. In some embodiments, the detection antibody is DCABH-13797. In some embodiments, the detection antibody is ProSci RF16062. In some embodiments, the capturing antibody is ProSci RF16062 and the detection antibody is DCABH-13797. In some embodiments, the capturing antibody is Enzo ALX-804-841-C100 and the detection antibody is ProSci RF16062.

In some embodiments, the sample is serum, plasma, saliva, or stool. In some embodiments, the sample is a serum sample.

Example 1

A study was conducted in which serum from subjects with acute COVID-19 infections was tested to determine the levels of free LIGHT and other cytokines/inflammatory markers during the acute phase of the illness. Whether there are differences in LIGHT levels and other inflammatory markers in healthy controls versus subjects with mild to severe disease with ALI/ARDS was determined. It was expected that subjects with severe COVID-19 infection will have higher levels of serum free LIGHT and other inflammatory markers compared to healthy controls or subjects with a mild or moderate coronavirus infection without ARDS, and that, furthermore, these markers could be useful in identifying subjects who might benefit from treatment with anti-LIGHT therapy. Given LIGHT's role in mediating immune response, particularly its roles in inflammatory cell infiltration and T cell activation, these subjects were expected to benefit from anti-LIGHT antibody therapy. Thus, the assay results were expected to provide the clinician with guidance as to which therapeutic agents are appropriate.

The study included 30 healthy controls, 28 subjects who were intubated and had severe COVID-19 infection, and 20 subjects who were non-ventilated and had mild to moderate COVID-19 infection. Blood was drawn from the subjects at a single timepoint. Using the free LIGHT assay described herein in Example 4, the presence and level of free (active) LIGHT in the blood serum was determined; the determination took place upon intubation for intubated patients.

Figure 6:
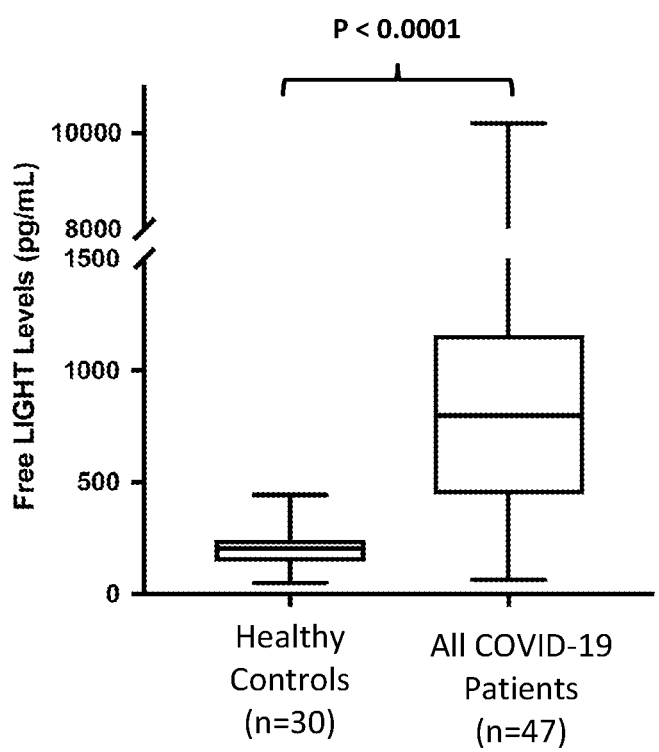
FIG. 6 shows serum free LIGHT levels in hospitalized COVID-19 patients versus healthy controls. Free LIGHT levels in serum were analyzed using the Kruskal-Wallis test (non-parametric one-way ANOVA). P-value was <0.0001 indicating higher free LIGHT levels for COVID-19 patients versus controls.

Free LIGHT was significantly ($p<0.0001$) elevated in COVID-19 subjects (N=47) as compared to healthy controls (N=30). See FIG. 6.

Figure 7:
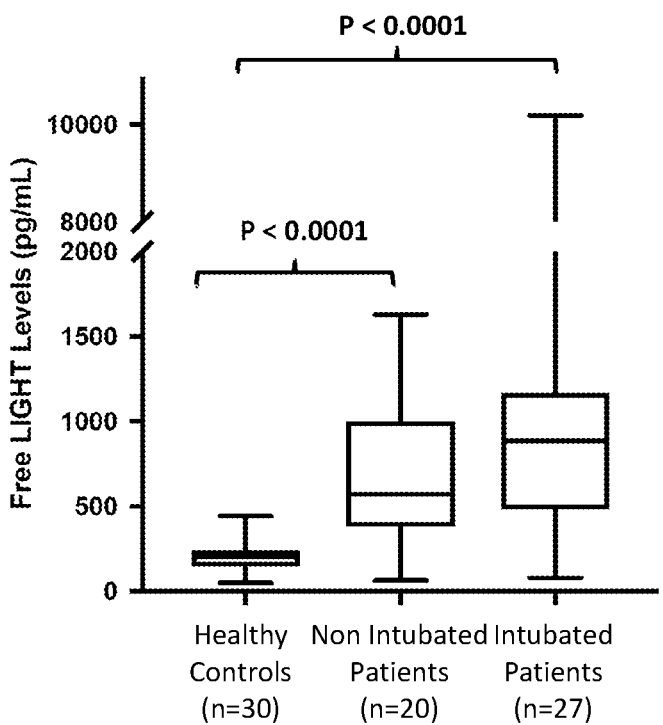
FIG. 7 shows serum free LIGHT levels in non-ventilated and intubated COVID-19 patients versus healthy controls. Free LIGHT levels in serum were analyzed using the non-parametric Kruskal-Wallis test. Separate tests were performed for comparison of Non-Ventilated and Intubated patients versus Controls. P-values for both tests were <0.0001.

Free LIGHT was also significantly ($p<0.0001$) elevated in serum of non-ventilated COVID-19 patients (N=20) and intubated COVID-19 patients (N=27) as compared to healthy controls (N=30). See FIG. 7.

Figure 8:
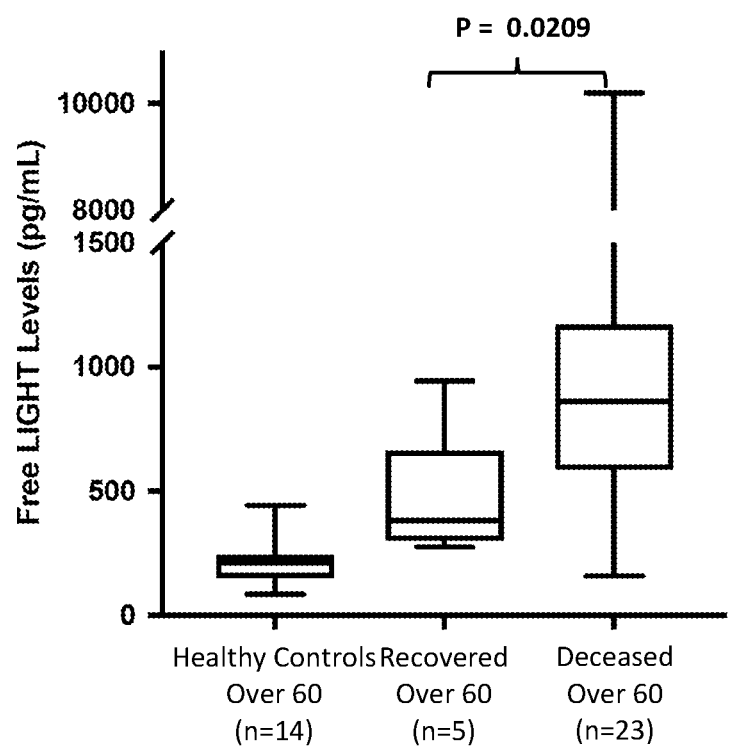
FIG. 8 shows serum free LIGHT levels were compared between healthy controls over 60 years of age (N=14), subjects over 60 years of age that eventually recovered (N=5), and subjects over 60 years of age that eventually died (N=23) using the Kruskal-Wallis test.

Additional evidence suggests that the highest free LIGHT levels were found in patients who required ventilator support, particularly in patients over the age of 60, and that elevated free LIGHT levels are associated with fatal outcomes in these patients, with a statistically significant association between higher serum LIGHT levels and mortality in patients over the age of 60 ($p=0.0209$). See FIG. 8. The observed mortality rate was higher for patients over 60 years of age (82%) compared to patients <60 years (32%).

Example 2

A randomized, double-blind, placebo-controlled, multi-center, phase 2 clinical trial to evaluate the efficacy and safety of an anti-LIGHT antibody in adults with COVID-19 pneumonia and acute lung injury was conducted according to the methods described in Example 2. The anti-LIGHT antibody has a VH of SEQ ID NO. 8, and a VL of SEQ ID NO: 9.

Example 2.1—Study Objectives and Endpoints

The primary objective of the study is to evaluate the effect of the anti-LIGHT monoclonal antibody compared with placebo in addition to standard of care on prevention of ARDS in adults with COVID-19 pneumonia and acute lung injury. The human anti-LIGHT monoclonal antibody administered comprises a heavy chain and a light chain that together comprise CDR-H1, CDR-H2, CDR-H3, CDR-L1, CDR-L2, CDR-L3 amino acid sequences: SEQ ID NOs: 2, 3, 4, 5, 6, and 7.

The secondary objectives of the study are: to evaluate the safety and tolerability of the anti-LIGHT monoclonal antibody compared with placebo in addition to standard of care, in adults with COVID-19 pneumonia and acute lung injury; and to evaluate the effect of the anti-LIGHT monoclonal antibody compared with placebo in addition to standard of care, on mortality in adults with COVID-19 pneumonia and acute lung injury.

The exploratory objectives are: to evaluate the effect of the anti-LIGHT monoclonal antibody compared with placebo in addition to standard of care, on viral load in adults with COVID-19 pneumonia and acute lung injury; and to evaluate the PK, pharmacodynamics (PD), and immunogenicity of the anti-LIGHT monoclonal antibody in adults with COVID-19 pneumonia and acute lung injury.

The primary endpoint of the study is: the proportion of subjects alive and free of respiratory failure over 28 days. Respiratory failure is defined based on resource utilization including one of the following: endotracheal intubation and mechanical ventilation; oxygen delivered by high-flow nasal cannula (heated, humidified, oxygen delivered via reinforced nasal cannula at flow rates >20 L/min with fraction of delivered oxygen ≥0.5); noninvasive positive pressure ventilation; or extracorporeal membrane oxygenation (ECMO).

The secondary endpoints of the study are: 1-month mortality defined as the proportion of subjects who were alive at the Day 28/early termination (ET); partial pressure of arterial oxygen/percentage of inspired oxygen (PaO2/FiO2) ratio; time to invasive ventilation; duration of ventilation support; intensive care unit (ICU) length of study; hospital length of stay; time to return to room air with resting pulse oximeter >93%; peak PaO2/FiO2 ratio; partial pressure of oxygen (P02); change in Sequential Organ Failure Assessment (SOFA) score; change in body temperature; and adverse event (AE) monitoring and safety laboratory determination.

The exploratory endpoints of the study are viral load in nasopharyngeal aspirates, LIGHT levels and inflammatory biomarker patterns (InflammationMAP), plasma concentrations of the anti-LIGHT monoclonal antibody over time, and measurement of anti-drug antibody (ADA).

Example 2.2—Study Design

This study is designed to determine the efficacy and safety of the anti-LIGHT monoclonal antibody compared with placebo in addition to standard of care, administered SC in subjects with COVID-19 pneumonia and acute lung injury. The primary objective of the study is to evaluate the effect of the anti-LIGHT monoclonal antibody on prevention of ARDS in adults with COVID-19 pneumonia and acute lung injury. The efficacy of the anti-LIGHT monoclonal antibody is determined by measuring PaO2/FiO2; alive, respiratory failure days; alive ventilator-free days; ICU and hospital length of stay; return to room air or baseline oxygen requirement; SOFA score; body temperature; viral load in nasopharyngeal aspirates; time to invasive ventilation; and duration of ventilation support. These are routinely used and accepted methods to assess respiratory functions. The study also assesses 1-month mortality rate, apart from other parameters.

The study takes place at approximately 10 study sites in the US.

83 patients are enrolled in the study. A screening log of study candidates is maintained at each study site.

Inclusion Criteria

Subjects fulfill the following requirements to be randomized into the study:

1. Subject/legally authorized representative (LAR) is able to understand and provide written informed consent and assent (as applicable) to participate in this study.

2. Subject is ≥18 years of age at the time of informed consent and assent (as applicable).

3. Subject is male or non-pregnant, non-lactating female, who if of childbearing potential agrees to comply with any applicable contraceptive requirements if discharged from the hospital prior to completing the study.

4. Subject has a diagnosis of COVID-19 infection through an approved testing method.

5. Subject is hospitalized due to clinical diagnosis of pneumonia with acute lung injury defined as diffuse bilateral radiographic infiltrates with PaO2/FiO2 >100 and <300.

6. If available, subject's oxygen saturation at rest in ambient air <93%.

Exclusion Criteria

The presence of any of the following criteria excludes a subject from the study:

1. Subject is intubated.

2. Subject is taking immunomodulators or anti-rejection drugs. The use of corticosteroids as part of standard of care measures in severe COVID-19 patients is permitted when clinically indicated and discussed with the Medical Monitor.

3. Subject has been administered an immunomodulating biologic drug within 60 days of baseline.

4. Subject is in septic shock defined as persistent hypotension requiring vasopressors to maintain mean arterial pressure (MAP) of 65 mm Hg or higher and a serum lactate level greater than 2 mmol/L (18 mg/dL) despite adequate volume resuscitation.

5. Subject has ALT/AST >5×ULN or creatinine >2.5 mg/dl

6. Subject has neutrophils <500/ml3

7. Subject has platelets <50,000/ml3

8. Subject has known hypersensitivity to any of the components of the anti-LIGHT monoclonal antibody 9. Subject has received any live attenuated vaccine, such as varicella-zoster, oral polio, or rubella, within 3 months prior to the baseline visit.

Screen Failures

Subjects who fail inclusion and/or exclusion criteria are not rescreened for the study.

Premature Subject Withdrawal

All subjects are advised that they are free to withdraw from participation in this study at any time, for any reason, and without prejudice. Investigators are instructed to make every reasonable attempt to keep subjects in the study; however, subjects have to be withdrawn from the study if they withdraw consent to participate.

The sponsor reserves the right to request the withdrawal of a subject due to protocol deviations or other reasons.

The investigator also has the right to withdraw subjects from the study at any time for any reason. If a subject is withdrawn before completing the study, the subject is supposed to be followed-up as instructed in the Schedule of Assessments (Table 1). The reason for withdrawal has to be determined by the investigator and recorded in the subject's medical record and on the case report form (CRF). If a subject is withdrawn for more than 1 reason, each reason is supposed to be documented in the source document and the most clinically relevant reason is to be entered on the CRF.

Possible reasons for discontinuation include but are not limited to:

Adverse event

Major protocol deviation

Withdrawal by subject from study assessments

Withdrawal by subject from study drug

Lost to follow-up

Other. If Other selected, the investigator required to specify the reason on the CRF.

Subject Replacement Criteria

Subjects who withdraw or are discontinued from the study are allowed to be replaced.

TABLE 1

Schedule of Assessments

| Procedure | Baseline (Day 1) | Day 2 | Day 5 | Day 8 | Day 9 | Day 14 | Day 28/ E T[1] | Safety Follow-up Phone Call Day 60[2] |
|---|---|---|---|---|---|---|---|---|
| Informed consent and assent (as applicable) | X | | | | | | | |
| Randomization | X | | | | | | | |
| Concomitant medications[3] | X | X | X | X | X | X | X | X |
| Adverse events[4] | X | X | X | X | X | X | X | X |
| Viral load in nasopharyngeal aspirates[9] | X | | X | | | | | |
| ECG[7] | X | X | X | X | X | X | X | |
| Pregnancy test[10] | X | | | | | | | |
| PK | | X[6] | | X | | X | X | |
| LIGHT and InflammationMAP | X[5] | X[6] | X | X | X | X | X | |
| ADA[8] | | | | X | | X | X | |
| Investigational product administration | X | | | | | | | |

Abbreviations: ADA = antidrug antibodies; EC = electrocardiogram; ET = early termination; InflammationMAP = inflammatory biomarker patterns; LIGHT = Lymphotoxin-like, exhibits Inducible expression, and competes with Herpes Virus Glycoprotein D for Herpesvirus Entry Mediator, a receptor expressed by T lymphocytes; PK = pharmacokinetics.

[1]Day 28 is conducted as a follow-up call for subjects who are discontinued from the study and for subjects who are discharged prior to the Day 28 visit. Additionally, if a subject is discontinued from the study or discharged from the hospital prior to Day 28, the Day 28/ET visit procedures are to be performed. No further visits are required to be performed with the exception of the Day 28 and Day 60 follow-up calls.
[2]A safety follow-up call is conducted approximately 59 days (±7 days) after administration of investigational product.
[3]Concomitant medications are collected throughout the study period.
[4]Adverse events are collected throughout the study period.
[5]Samples ae collected prior to investigational product administration.
[6]Samples are collected 24 hours (±2 hours) post Day 1 dosing.
[7]An ECG is collected daily when a subject is not being assessed by cardiac monitoring.
[8]An ADA sample is collected at Days 8, 14, 28/ET. Additionally, a sample is collected when an immunologically related adverse event is reported (e.g., a skin reaction, lupus-like syndrome, unexplained thrombocytopenia).
[9]If the site is unable to do a quantitative test in order to obtain viral load, the viral load samples to be collected at Days 1 and 5 are not required to be collected.
[10]For females of childbearing potential. A subject is not considered to be of childbearing potential if they are post-menopausal (12 consecutive months of spontaneous amenorrhea and ≥ age 51 years, and/or surgically sterile (having undergone one of the following surgical acts: hysterectomy, bilateral tubal ligation, bilateral oophorectomy or bilateral salpingectomy) and at least 6weeks post-sterilization.

TABLE 2

Standard of Care Procedures

Procedure
ABG
Chest CT/CXR
Glasgow Coma Scale
Laboratory procedures including CBC, chemistry and urinalysis
CRP
Physical examination
Pulse Oximetry TABLE 2-continued Standard of Care Procedures SOFA
Temperature
Vital signs Abbreviations: ABG = arterial blood gas; CBC = complete blood count; CRP = C-reactive protein; CT = computed tomography; CXR = chest x-ray; SOFA = Sequential Organ Failure Assessment. These procedures are performed per the site's practice unless defined otherwise Example 2.3—Treatments Identification of Investigational Product(s), Dose and Mode of Administration The anti-LIGHT monoclonal antibody is the investigational product that is used in this study. It is supplied in vials. Placebo is sourced locally and provided as volume-matched normal saline for injection. The anti-LIGHT monoclonal antibody or placebo is administered by SC injection in the abdomen in a zone of 4 to 10 cm from the umbilicus with the injection site rotated based on the number of syringes used. The anti-LIGHT monoclonal antibody or placebo is administered at baseline (Day 1). The anti-LIGHT monoclonal antibody is administered at 16 mg/kg dose (maximum dose of 1200 mg).

Labeling and Packaging

All packaging and labeling operations are performed by the sponsor or designee per Good Manufacturing Practice and Good Clinical Practice (GCP) rules. The investigational product is sent to the study site by the sponsor or designee. Labeling is in local language and dependent upon local regulations.

Treatments Administered

Eligible subjects receive the anti-LIGHT monoclonal antibody or placebo on Day 1 in addition to standard of care. The standard of care is to be maintained throughout the study and is allowed to include off-label use of other drugs, devices, or interventions used to treat COVID-19.

Dispensing and Storage

The anti-LIGHT monoclonal antibody supplied by sponsor is used exclusively in this clinical study per the instructions of the protocol. Placebo is sourced locally and provided as volume matched injection of normal saline. The investigator is responsible for dispensing the investigational product per the dosage scheme and for ensuring proper storage of the investigational product.

The unblinded pharmacist is to confirm the receipt of the investigational product with his/her signature. A copy of this receipt is to be kept by the unblinded pharmacist, and another copy is stored at sponsor and/or designee. Until the investigational product is dispensed to the subjects, it is stored at 2° C. to 8° C. (35.6° F. to 46.4° F.) and protected from light. Investigators or other authorized persons (e.g., pharmacists) are responsible for storing the investigational product provided by the sponsor in a secure and safe place in accordance with local regulations, labeling specifications, institutional policies and procedures.

Control of storage conditions for the investigational product provided by the sponsor, especially control of temperature (e.g., refrigerated storage) and daily temperature monitoring, and information on in-use stability and instructions for handling the investigational product are to be managed according to the rules provided by the sponsor.

Blinding and Unblinding Treatment Assignment

This is a double-blind study. All subjects, investigators, and study personnel involved in the conduct of the study, including data management, are blinded to treatment assignment except for the following individuals: specified unblinded statistician from the Contract Research Organization (CRO) who has access to the randomization code; and specified unblinded pharmacist(s) from the hospital who have access to the randomization code in order to prepare the investigational product.

The unblinded pharmacist(s) and unblinded statistician do not otherwise participate in the study or data analysis prior to unblinding of the study.

Treatment unblinding is discouraged if knowledge of the treatment assignment does not materially change the planned management of a medical emergency. Unblinding is permitted in a medical emergency that requires immediate knowledge of the subject's treatment assignment. Whenever possible unblinding is to be discussed with the Sponsor Medical Monitor. For emergency unblinding the Investigator is to contact the unblinded pharmacist(s). If the Investigator is not able to discuss treatment unblinding in advance, then they are to notify the Sponsor Medical Monitor as soon as possible about the unblinding incident without revealing the subject's treatment assignment. The Investigator or designee is to record the date and reason for study discontinuation on the appropriate eCRF for that subject. In all cases that are not emergencies, the Investigator is to discuss the event with the Sponsor Medical Monitor prior to unblinding the subject's treatment assignment.

If the treatment assignment is unblinded for an individual subject, the Investigator is to be notified of that subject's treatment assignment without unblinding the treatment assignments for the remaining subjects in the study. The Investigator is to make this decision after consultation with the Sponsor Medical Monitor.

Selection of Doses in the Study

The dose of 16 mg/kg (maximum dose of 1200 mg) is selected in an effort to maximize the ability to achieve the blockade of LIGHT while ensuring patient safety. In a robust toxicology program the anti-LIGHT monoclonal antibody was dosed as high as 100 mg/kg in monkeys and was well tolerated while the NOAEL was determined to be 60 mg/kg. In dosing in humans, the anti-LIGHT monoclonal antibody was safe and well tolerated in single ascending doses up to 1200 mg in healthy volunteers. There were no clinically meaningful treatment-emergent adverse events or changes in ECG parameters or laboratory values. A safety review committee analyzed data from individual subjects and across all subjects treated in a daily fashion to assess any safety signals with dosing.

Dose Adjustment Criteria

No dose adjustments are allowed.

Drug Accountability

Records showing the receipt, dispensing, or other disposition of the investigational product including the date, lot identifier, dosage, volume administered to each subject, and identification of subjects (subject number and initials) who receive the investigational product are maintained by an unblinded pharmacist. The investigator does not supply the investigational product to any person except those named as subinvestigators on the US Food and Drug Administration (FDA) Form FDA 1572 and designated study personnel, and subjects in this study. The investigator does not dispense the investigational product from any study locations other than those listed on Form FDA 1572. If any of the investigational product is not dispensed, is lost, stolen, spilled, unusable, or received in a damaged container, that information is to be documented and reported to sponsor and appropriate regulatory agencies, as required.

Upon completion of the study, unused investigational product may be left in the original packaging for final disposition by the sponsor or per the site's standard practice. Any partially used investigational product and all empty packaging (e.g., vials) may be saved for final disposition by the sponsor, returned to the sponsor's designee for destruction, or per the site's standard practice.

Permitted and Prohibited Therapies

All non-study therapies including but not limited to over-the-counter and non-pharmacological treatments received within 7 days prior to baseline and through the end of study are recorded on the appropriate electronic case report form (eCRF) page.

Prior Therapies

Prior treatment includes all treatment received within 7 days of the date of first dose of investigational product. Prior treatment information is recorded on the appropriate eCRF page.

Concomitant Therapies

Concomitant therapies refer to all therapies taken between the dates of the first dose of investigational product and the end of the follow-up period, inclusive. Concomitant treatment information is recorded on the appropriate CRF page.

Permitted Therapies

Medications considered necessary for the subject's welfare are administered at the discretion of the investigator. The Sponsor Medical Monitor may be contacted in the event the site is in a situation where further clarity is needed.

Acceptable methods of birth control are implants, injectables, combined oral contraceptives, intrauterine device, sexual abstinence or vasectomized partner.

Prohibited Therapies

Subjects may not have been administered an immunomodulating biologic drug within 60 days prior to the baseline visit, or have received any live attenuated vaccine, such as varicella-zoster, oral polio, or rubella, within 3 months prior to the baseline visit. During the study, new initiation of investigational compounds may be prohibited, with the exception of corticosteroids, which are permitted to be administered as part of standard of care measures in severe COVID-19 patients when clinically indicated and discussed with the Medical Monitor. The use of immunomodulatory or anti-rejection drugs may be prohibited.

Treatment after End of Study

Subjects are treated per standard clinical practice throughout the study.

Example 2.4—Study Procedures

Subjects/LAR provide written informed consent and assent (as applicable) before study-related procedures are initiated.

For the timing of assessments and procedures throughout the study, refer to the schedule of events (Table 1 and Table 2). The procedures listed in Table 2 are considered standard of care and are performed per the site's practice unless defined otherwise. Throughout the study, every reasonable effort is made by study personnel to follow the timing of assessments and procedures in the schedule of events for each subject.

Study Duration

The anti-LIGHT monoclonal antibody and placebo treatment are administered on Day 1 and the duration of the study period was 60 days.

Efficacy Assessments

Efficacy response is assessed by the following procedures at the time points mentioned in the Schedule of Assessments (Table 1 and Table 2): Arterial blood gas (ABG) test to measure PaO2/FiO2; pulse oximetry; the SOFA score measurement (The SOFA score is a simple and objective tool to calculate both the number and the severity of organ dysfunction in the following 6 organ systems: respiratory, coagulatory, liver, cardiovascular, renal, and neurologic [Table 3], and the score can measure individual or aggregate organ dysfunction (Vincent J L, Moreno R, Takala J, et al. The SOFA (Sepsis-related Organ Failure Assessment) score to describe organ dysfunction/failure. On behalf of the Working Group on Sepsis-Related Problems of the European Society of Intensive Care Medicine. Intensive Care Med. 1996; 22(7):707-710]); body temperature; viral load in nasopharyngeal aspirates. Apart from these tests, time to invasive ventilation and duration of ventilation support, are also recorded.

Safety Assessments

Safety and tolerability assessments include the frequency and severity of AEs as well as the evaluation of changes in clinical laboratory values, vital signs, ECG recordings, and physical examination findings.

Clinical Laboratory Tests to be Performed

A sample for C-reactive protein is collected at the time points specified in the Schedule of Assessments (Table 1). With the exception of PK, LIGHT and InflammationMAP samples, all other laboratory samples are considered standard of care and may be performed per the site's practice.

Laboratory specimens are analyzed at the hospital laboratory per their collection and processing requirements.

Sampled Blood Volume

The sampled blood volume for this study is shown in Table 4.

TABLE 3

The Sequential Organ Failure Assessment (SOFA) score

| SOFA Score | 1 | 2 | 3 | 4 |
|---|---|---|---|---|
| Respiration | | | | |
| $PaO_2/FiO_2$ (mmHg) | <400 | <300 | <200 (with respiratory support) | <100 (with respiratory support) |
| Coagulation | | | | |
| Platelets × $10^3/mm^3$ | <150 | <100 | <50 | <20 |
| Liver | | | | |
| Bilirubin (mg/dL) | 1.2-1.9 | 2.0-5.9 | 6.0-11.9 | >12.0 |
| Cardiovascular[a] | | | | |
| Hypotension | MAP <70 mmHg | Dopamine ≤5 or dobutamine (anydose) | Dopamine >5 or epinephrine <0.1 or norepinephrine ≤0.1 | Dopamine >15 or epinephrine >0.1 or norepinephrine >0.1 |
| Central Nervous System | | | | |
| Glasgow Coma Score | 13-14 | 10-12 | 6-9 | <6 |
| Renal | | | | |
| Creatinine (mg/dL) or urine output (mL/day) | 1.2-1.9 | 2.0-3.4 | 3.5-4.9 or <500 | >5.0 or <200 |

MAP: mean arterial pressure; PaO2/FiO2: partial pressure of arterial oxygen/percentage of inspired oxygen.[a] Adrenergic agents administered for at least 1 h (doses given are in µg/kg-min).

Reference: Vincent J L, Moreno R, Takala J, et al. The SOFA (Sepsis-related Organ Failure Assessment) score to describe organ dysfunction/failure. On behalf of the Working Group on Sepsis-Related Problems of the European Society of Intensive Care Medicine. Intensive Care Med. 1996; 22(7): 707-710.

TABLE 4

Sampled Blood Volume per Subject

| Assessment | Sample Volume (mL) | Number of Samples | Total Volume (mL) |
|---|---|---|---|
| Anti-LIGHT monoclonal antibody concentration and PK analysis | 2.0 | 4 | 8.0 |
| Anti-drug Antibodies | 2.0 | 3 | 6.0 |
| LIGHT/InflammationMAP | 2.5 | 7 | 17.5 |
| Total mL | — | — | 27.5 |

InflammationMAP = inflammatory biomarker patterns; LIGHT = Lymphotoxin-like, exhibits Inducible expression, and competes with Herpes Virus Glycoprotein D for Herpesvirus Entry Mediator, a receptor expressed by T lymphocytes Anti-LIGHT Monoclonal Antibody Concentration, Pharmacokinetic and Anti-drug Antibody Assessments Pharmacokinetics and ADA assessments are calculated from the plasma concentrations of the anti-LIGHT monoclonal antibody.

Specimen Handling Requirements

The transmission of infectious agents may occur through contact with contaminated needles and blood or blood products. Consequently, appropriate blood and body fluid precautions may be employed by all study personnel involved in the collection of blood and handling of specimens in both the clinic and laboratory settings. Refer to current recommendations of the appropriate authorities.

In addition to appropriate handling of subject samples, specific regulations exist regarding the shipment of biologic/etiologic samples. Procedures and regulations for the packaging and shipping of infectious samples are outlined in the site and/or study laboratory manual. The investigator is responsible for ensuring that all study samples that are transported to another location are appropriately packed and shipped per the applicable regulations.

Evaluation of Laboratory Values

The normal ranges of values for the laboratory assessments in this study are provided by the local laboratory of each hospital. They are regarded as the reference ranges on which decisions are be made for the specific site.

If a laboratory value is out of the reference range, it is not necessarily clinically relevant. The investigator may evaluate the out-of-range values and record his/her assessment of the clinical relevance in the subject's source documentation.

All laboratory values which, in the investigator's opinion, show clinically relevant or pathological changes during or after termination of the treatment are to be discussed with the medical monitor, as necessary, and reported as AEs and followed.

All measurements described in this section are recognized standard methods.

Clinical Examination: Blood Pressure, Pulse Rate, Respiratory Rate, Temperature, Height, and Body Weight Blood pressure, pulse rate, respiratory rate, temperature, height, and body weight are considered standard of care and are performed per the site's practice. Additional blood pressure and pulse rate measurements are allowed to be performed, as determined by the investigator, to ensure appropriate monitoring of subject safety and accurate recording of vital sign measurements. Any changes from baseline which are deemed clinically significant by the investigator are recorded as an AE.

Clinical Examination: Electrocardiogram

A standard 12-lead ECG is considered standard of care and is performed daily for those who are not being assessed by cardiac monitor. They are performed per the site's practice unless defined otherwise in Table 2. All ECG recordings are identified with the subject number, subject initials, date, and time of the recording and a copy is included with the subject's source documentation. All ECGs may be performed using the equipment supplied by the investigational site.

Electronic ECG tracings are analyzed per the site's practice. In addition, the investigator's assessment of the ECG tracing as normal or abnormal are documented, and if abnormal, his/her determination of whether the abnormality is clinically significant or not may be documented on the tracing.

All ECG values which, in the investigator's opinion, show clinically relevant or pathological changes during or after termination of the treatment may be discussed with the Sponsor Medical Monitor and reported as AEs and followed.

Clinical Examination: Physical Examination

A complete physical examination is considered standard of care and is performed per the site's practice unless defined otherwise in Table 2. Any clinically significant physical examination findings are reported as AEs and followed.

Clinical Examination: Adverse Events

The investigator is responsible for the detection and documentation of events meeting the criteria and definition of an AE or SAE described previously. Any clinically relevant observations made during the period of hospitalization are considered AEs.

Pharmacokinetics and Immunogenicity Analyses

Blood samples for PK analysis are collected on Day 2 at 24 hours (±2 hours) post dose and at any time on Days 8, 14 and 28. Blood samples for ADA analysis are collected at any time on Days 8, 14 and 28. Additionally, a sample is collected when an immunologically related adverse event is reported. Samples are processed to plasma. Time of PK samples is recorded in the eCRF. A total of 1.0 mL plasma per PK and ADA sample are collected from each subject to measure plasma concentrations of the anti-LIGHT monoclonal antibody and ADAs. Pharmacokinetic and ADA samples are to be processed according to the methods and directions set forward in the Laboratory Manual(s) and guidance(s). Pharmacokinetic and ADA plasma sample analysis are performed by laboratory defined in the Laboratory Manual(s) and guidance(s), according to their standard operating procedures (SOPs) using a validated enzyme-linked immunosorbent assay (ELISA). Assay and analysis details are described in the method validation and bioanalytical information.

Pharmacodynamics

Blood samples are collected for exploratory analyses. Exploratory analyses include are not limited to LIGHT levels and InflammationMAP as specified in Table 1. Exploratory biomarker analyses are performed at the laboratories specified in the Laboratory Manual(s) and guidance(s).

Example 2.5—Adverse Events

Adverse Event Collection

An AE is defined as any untoward medical occurrence in a patient or clinical investigation subject administered a pharmaceutical product that does not necessarily have a causal relationship with the product. An AE could therefore be any unfavorable and unintended sign (including a new, clinically important abnormal laboratory finding), symptom, or disease, temporally associated with the product, whether related to the product. An AE is considered treatment-emergent if it occurred after the first dose of investigational product and within 30 days of a subject's last dose of investigational product.

All AEs are collected from the time the informed consent was signed until the end of study (Day 60). This includes events occurring regardless of whether investigational product is administered. Where possible, a diagnosis rather than a list of symptoms is recorded. If a diagnosis is not yet made, then each symptom is listed individually. All AEs are captured on the appropriate AE pages in the eCRF and in source documents. In addition, to untoward AEs, unexpected benefits outside the investigational product indication are captured in the source documents and AE eCRF.

All AEs are followed to closure (the subject's health has returned to his/her baseline status or all variable have returned to normal), regardless of whether the subject was still participating in the study. Closure indicates that an outcome has been reached, stabilization achieved (the investigator does not expect any further improvement or worsening of the event), or the event was otherwise explained. When appropriate, medical tests and examinations are performed so that resolution of an event(s) could be documented. Severity of Adverse Events The severity of AEs are recorded during the course of the event including the start and stop dates for each change in severity. An event that changes in severity is captured as a new event. Worsening of a pre-treatment events, after initiation of investigational product is recorded as new AEs. For example, if the subject experiences mild, intermittent headaches prior to dosing with investigational product; however, the headache intensity increases to moderate after the first dose of investigational product, a new AE of moderate intermittent headaches is recorded in the source documents and eCRF.

The medical assessment of clinical severity of an AE is determined using the definitions outlined in Common Terminology Criteria for Adverse Events (CTCAE), Version 5.0 (Published Nov. 27, 2017 by the US Department of Health and Human Services, National Institutes of Health, National Cancer Institute). Grade 1 is defined as mild; asymptomatic or mild symptoms; or clinical or diagnostic observations only; or intervention not indicated. Grade 2 is defined as moderate; or minimal, local or non-invasive intervention indicated; or limiting age-appropriate instrumental activities of daily living (ADL). Grade 3 is defined as severe or medically significant but not immediately life-threatening; or hospitalization or prolongation of hospitalization indicated; or disabling; or limiting self-care ADL. Grade 4 is defined as life-threatening consequences; or urgent intervention indicated. Grade 5 is defined as deaths related to AE.

The above-referenced CTCAE document may be referred to for full description of CTCAE terms and instrumental and self-care ADLs. Severity is a classification of intensity whereas an SAE is an AE that meets serious criteria.

Relationship Categorization

A physician investigator makes the assessment of relationship to investigational product for each AE. The investigator decides whether, in his or her medical judgment, there is a reasonable possibility that the event may have been caused by the investigational product. If there is no valid reason for suggesting a relationship, then the AE may be classified as "not related".

Otherwise, the AE is categorized per the guidelines below. The causality assessment may be documented in the source document and the eCRF (Table 5).

TABLE 5

Assessment of Relationship to Investigational Product

| Relationship | Description |
| --- | --- |
| Not Related | Exposure to investigational product has not occurred.<br>OR<br>The administration of investigational product and the occurrence of the AE are notreasonably related in time<br>OR<br>The AE is considered likely to be related to an etiology other than the use of theinvestigational product, that is, there are no facts/evidence or arguments to suggest a causal relationship to the investigational product. |
| Possibly Related | The administration of the investigational product and the occurrence of the AE arereasonably related in time.<br>AND<br>The AE could not be explained equally well by factors or causes other than exposure toinvestigational product |
| Probably Related | The administration of investigational product and the occurrence of the AE are reasonablyrelated in time.<br>AND<br>The AE is more likely explained by exposure to investigational product than by other factors or causes. |

Outcome at the Time of Last Observation

The outcome at the time of last observation is classified as: recovered/resolved; recovered/resolved with sequelae; recovering/resolving; not recovered/not resolved; fatal; or unknown.

Reporting of Serious Adverse Events

Initial and follow-up SAE reports are completed by the investigator or designee and sent to the CRO within 24 hours of the first awareness of an SAE. The investigator or designee completes, signs and dates the appropriate SAE form and verifies the accuracy of the information against corresponding source documents. This information is sent to the CRO Pharmacovigilance Department.

Serious Adverse Event Definition

An SAE is defined as any untoward medical occurrence, whether considered to be related to investigational product or not, that at any dose: results in death; is life-threatening;

requires inpatient hospitalization or prolongation of existing hospitalization; results in persistent or significant disability/incapacity; is a congenital anomaly; or is an important medical event.

Note that the term "life-threatening" in the definition of "serious" refers to an event in which the subject is at risk of death at the time of the event; it does not refer to an event which hypothetically might have caused death if it were more severe.

Note that the term "inpatient hospitalization" is defined as 24 hours in a hospital or an overnight stay. An elective hospital admission to treat a condition present before exposure to the test drug, or a hospital admission for a diagnostic evaluation of an AE, does not qualify the condition or event as an SAE. Further, an overnight stay in the hospital that is only due to transportation, organization, or accommodation problems and without medical background does not need to be considered an SAE.

Note that the term "congenital anomaly" refers to an infant born to a mother who was exposed to the investigational product during pregnancy is an SAE. However, a newly diagnosed pregnancy in a subject that receives an investigational product is not to be considered an SAE unless it is suspected that the investigational product(s) interacted with a contraceptive method and led to the pregnancy.

Note that medical and scientific judgment may be exercised in deciding whether it is appropriate to consider other situations serious, such as important medical events that are not immediately life-threatening or do not result in death or hospitalization but may jeopardize the subject or may have required intervention to prevent one of the other outcomes listed in the definition above. Examples of such events are intensive treatment in an emergency room or at home for allergic bronchospasm, blood dyscrasias or convulsions that do not result in hospitalization, or development of drug dependency or drug abuse.

Serious Adverse Event Collection Time Frame

All SAEs, regardless of the relationship to study, are collected from the time the subject/LAR signed the informed consent and assent [if applicable] until the subject's last contact. The investigator or designee was to report all SAEs promptly to CRO within 24 hours of first becoming aware of the event.

Any SAE(s), regardless of relationship to study, discovered by the investigator at any interval after study was completed are reported to CRO within 24 hours of the first awareness of the event.

Serious Adverse Event Onset and Resolution Dates

The onset date of the SAE is defined as the date the event meets serious criteria. The resolution date is the date the event no longer meets serious criteria, the date symptoms resolve, or the event is considered chronic. In the case of hospitalization, the hospital admission and discharge dates are considered respectively, the onset and resolution date of the SAE.

Any signs or symptoms experienced by the subject after signing the informed consent form and assent form (if applicable), or leading up to the onset date of the SAE or following the resolution date of the SAE are recorded as an AE.

Fatal Outcome

Fatal is only selected as an outcome when the AE results in death. If more than 1 AE is possibly related to the subject's death, the outcome of death is to be indicated for each such AE.

Any AE that results in the subject's death have fatal checked as an outcome with the date of death recorded as the resolution date. AEs resulting in death were required to be reported within 24 hours as a SAE, if not already reported as such. In the event of a subject's death, data was to be collected on whether the death occurred after the withdrawal of care and, if so, the reason for the withdrawal of care.

For other AEs, ongoing at the time of death that did not contribute to the subject's death, the outcome was to be considered not resolved, without a resolution date recorded.

Adverse Events of Special Interest

There are no events from research to date which qualify as AEs of special interest.

Adverse drug reactions observed in an anti-LIGHT monoclonal antibody pre-clinical observation include injection site reactions.

Observations for reactions with other biological agents include: potential for increased infection (including opportunistic infections such as tuberculosis); hypersensitivity reactions (including anaphylaxis); immunogenicity; malignancy; and impaired immunization.

Any new infection that occurred on study, regardless of the infecting agent (i.e. viral or non-viral), was to be captured. Additionally, the site of infection and source of culture (bronchoalveolar lavage, tracheal aspirate, sputum, blood, urine etc.) was to be captured.

Pregnancy

All females of childbearing potential who participate in the study are counseled on the need to practice adequate birth control and on the importance of avoiding pregnancy during study participation. Females are instructed to contact the investigator or study staff immediately if pregnancy occurred or is suspected.

Pregnancy testing is conducted on females of childbearing potential at baseline. Any female who is found to be pregnant at baseline is excluded from the study and considered to be a screening failure. Any female who is found to be pregnant after the dosing is required to be discontinued from the study and the end of study visit assessments performed as soon as possible after learning of the pregnancy.

The investigator reports the pregnancy of any female (study participant or female partner of male study participant) who became pregnant during investigational product treatment or within 60 days of being randomized and receiving the investigational product. The pregnancy is reported within 24 hours of learning of the pregnancy to the CRO using the Pregnancy Data Collection Form via the same fax and email address as for SAE reporting. The investigator contacts the designated individual(s) who receive SAE notification and record information related to the pregnancy on an Exposure in Utero form/other designated form provided by the sponsor or its designee.

The investigator is also responsible for following the pregnancy until delivery or termination. These findings are reported on the Pregnancy Data Collection Form and forwarded to the designated individual(s). The event meets the SAE criterion only if it results in a spontaneous abortion or a congenital anomaly.

Anaphylaxis

Any AE that represents an anaphylactic reaction is classified using the definitions provided in Sampson H A, Munoz-Furlong A, Campbell R L, et al. Second symposium on the definition and management of anaphylaxis: Summary Report-Second National Institute of Allergy and Infectious Disease/Food Allergy and Anaphylaxis Network Symposium. J Allergy Clin Immunol 2006; 117(2):391-97, and shown in Table 6.

TABLE 6

Clinical Criteria for Diagnosing Anaphylaxis
Anaphylaxis is highly likely when any one of the following 3 criteria are fulfilled:

1. Acute onset of an illness (minutes to several hours) with involvement of the skin, mucosal tissue, or both (eg, generalized hives, pruritus or flushing, swollen lips-tongue-uvula)
   AND AT LEAST ONE OF THE FOLLOWING
   a. Respiratory compromise (eg, dyspnea, wheeze-bronchospasm, stridor, reduced PEF, hypoxemia)
   b. Reduced BP or associated symptoms of end-organ dysfunction (eg, hypotonia [collapse], syncope, incontinence)
2. Two or more of the following that occur rapidly after exposure to a likely allergen for that patient (minutes toseveral hours):
   a. Involvement of the skin-mucosal tissue (eg, generalized hives, itch-flush, swollen lips-tongue-uvula)
   b. Respiratory compromise (eg, dyspnea, wheeze-bronchospasm, stridor, reduced PEF, hypoxemia)
   c. Reduced BP or associated symptoms (eg, hypotonia [collapse], syncope, incontinence)
3. Reduced BP after exposure to known allergen for that patient (minutes to several hours):
   a. Infants and children: low systolic BP (age specific) or greater than 30% decrease in systolic BP*
   b. Adults: systolic BP of less than 90 mm Hg or greater than 30% decrease from that person's baseline

*Low systolic blood pressure for children is defined as less than 70 mm Hg from 1 month to 1 year, less than(70 mm Hg + [2 × age]) from 1 to 10 years, and less than 90 mm Hg from 11 to 17 years.
Abbreviations: Peak expiratory flow; BP = blood pressure
Reference: Sampson H A, Munoz-Furlong A, Campbell R L, et al. Second symposium on the definition and management of anaphylaxis: Summary Report-Second National Institute of Allergy and Infectious Disease/Food Allergy and Anaphylaxis Network Symposium. J Allergy Clin Immunol 2006; 117(2): 391-97).

Example 2.6—Statistics

Sample Size Determination

A total of 83 subjects are randomized to one of two treatment groups (the anti-LIGHT monoclonal antibody or placebo in addition to standard of care) in a 1:1 ratio. One subject withdrew, leaving 82 subjects. This sample size of 82 subjects provides greater than 80% power to detect a difference of 0.25 (25%) in the proportion of subjects alive and free of respiratory failure using a Chi-square exact test at a one-sided significance level of 0.05. This calculation assumes that the proportion alive and free of respiratory failure is 0.60 in the placebo group and 0.85 in the anti-LIGHT monoclonal antibody group.

Analysis Populations

This study has several populations of interest. The Randomized Analysis Set includes all subjects who are randomized in the study. Subjects are categorized according to their randomized treatment group. The Randomized Analysis Set is used for all disposition, protocol deviations, and demographic and other baseline characteristics analyses. The Safety Analysis Set includes all subjects who are randomized in the study and receive at least one dose of investigational product. Subjects are categorized according to their actual treatment group. The Safety Analysis Set is used for all exposure and safety analyses. The Full Analysis Set includes all subjects who receive at least one dose of investigational product and have a baseline and at least one post-baseline efficacy assessment. Subjects are categorized according to their randomized treatment group. The Full Analysis Set is used for all efficacy and pharmacodynamic analyses. The PK Analysis Set includes all subjects who receive at least one dose of investigational product and have at least one post dose measurable plasma sample. Subjects are categorized according to their actual treatment group. The PK Analysis Set is used for all PK analyses.

Statistical Analyses

All efficacy and safety variables are summarized using descriptive statistics. Descriptive statistics for continuous data include number of subjects (n), mean, standard deviation (SD), median, minimum, and maximum. Summaries of change from baseline variables include only subjects who had both a baseline value and corresponding value at the timepoint of interest. Descriptive statistics for categorical data include frequency and percentage.

Listings are provided for all collected study data.

The disposition of all subjects randomized in this study are summarized by treatment group and completion/discontinuation status. Subjects who discontinue the study prematurely are summarized by treatment group and reason for discontinuation. The number of subjects in each analysis set was summarized by treatment group.

All subject data is reviewed for the occurrence of protocol deviations. Prior to database lock, all protocol deviations are reviewed and classified with respect to the potential to influence experimental outcomes. Protocol deviations are summarized by treatment group.

Demographic and other baseline characteristics are summarized by treatment group using descriptive statistics.

All prior and concomitant medications are coded using the WHO Drug Dictionary. Prior and concomitant medications are summarized by treatment group using descriptive statistics.

Exposure to investigational product is summarized by treatment group using descriptive statistics.

Safety analyses are conducted using data from the Safety Analysis Set. Safety variables included TEAEs, clinical laboratory values, vital signs, and ECG results. No formal inferential analyses are conducted for any safety variables, unless otherwise noted.

Adverse event verbatim terms are coded using the Medical Dictionary for Regulatory Activities (MedDRA). The overall incidence of subjects having at least one AE are summarized by treatment group. The incidence of TEAEs is summarized by treatment group, system organ class (SOC) and preferred term (PT). Each subject is counted only once per SOC and preferred term. An AE was considered treatment-emergent if it occurred after the first dose of investigational product and within 30 days after a subject's last dose of investigational product.

For all continuous laboratory test variables, descriptive statistics for all reported values and change from baseline values are summarized by treatment group and time point.

For all continuous vital sign and ECG variables, descriptive statistics for all reported values and change from baseline values are summarized by treatment group and time point. In addition, the frequency and percentage of subjects with abnormal ECG findings are summarized.

The proportion of subjects alive and free of respiratory failure with 90% confidence interval is now presented. In addition, the proportion of subjects alive and free of respiratory failure in the anti-LIGHT monoclonal antibody group has been compared to that in the placebo group using a Chi-square test or similar methods. Other dichotomous efficacy variables are analyzed similarly. All efficacy variables have been summarized using descriptive statistics.

For all PK variables, descriptive statistics are presented by collection timepoint (where applicable) using the PK Analysis Set. Descriptive statistics for plasma concentrations include n, number of subjects with concentrations below the level of quantification (BLQ), mean, SD, coefficient of variation, median, minimum, and maximum. For descriptive summaries, plasma concentrations reported as BLQ are be set to zero.

For all PD variables, descriptive statistics are presented by treatment group and time point.

For all immunogenicity variables, descriptive statistics are presented by treatment group and time point.

Example 3

Presented herein in Example 3 are certain results of the study conducted according to the methods as described in Example 2.

The screening involved identifying patients with COVID-19 associated pneumonia and mild to moderate ARDs. Then, patients meeting these criteria (n=83) were randomized 1:1 to receive standard of care treatment plus the anti-LIGHT monoclonal antibody or standard of care treatment plus placebo. One out of 83 patients withdrew informed consent. A total of 82 patients were administered either standard of care treatment plus the anti-LIGHT monoclonal antibody or standard of care treatment plus placebo. A full analysis for secondary endpoints and safety was completed for these patients. An ITT analysis for primary endpoint was completed in a group of 62 of the patients who were free of high flow O2 or positive pressure O2 with 28-day follow-up.

Greater than 90% of patients in the study received corticosteroids and greater than 60% received remdesivir. Patient demographics were as follows in Table 7:

TABLE 7

| Patient Demographics | | |
| --- | --- | --- |
| Characteristic | Anti-LIGHT monoclonal antibody (n = 41) | Placebo (n = 42) |
| Age, years | | |
| Mean (SD) | 59.2 (14.5) | 58.1 (14.2) |
| Age Group | | |
| <60 years (n, %) | 20 (48.8%) | 21 (50.0%) |
| >60 years (n, %) | 21 (51.2%) | 21 (50.0%) |
| Gender | | |
| Male | 25 (61%) | 32 (76.2%) |
| Female | 16 (39%) | 10 (23.8%) |

TABLE 7-continued

| Patient Demographics | | |
| --- | --- | --- |
| Characteristic | Anti-LIGHT monoclonal antibody (n = 41) | Placebo (n = 42) |
| Race | | |
| White | 31 (75.1%) | 37 (88.1%) |
| Black or African American | 7 (17.1%) | 3 (7.1%) |
| Asian | 2 (4.9%) | 0 (0%) |
| Other | 1 (2.4%) | 2 (4.8%) |
| Free LIGHT Level at Baseline | | |
| Mean (range) pg/ml | 348 (63-1050) | 273 (37-843) |
| Concomitant Medication Use at Baseline* | | |
| Systemic corticosteroids | 38 (95.0%) | 37 (88.1%) |
| Remdesivir | 26 (65.0%) | 28 (66.7%) |

*Calculated from patients dosed (n = 40 for the anti-LIGHT monoclonal antibody, n = 42 for placebo).

Figure 10:
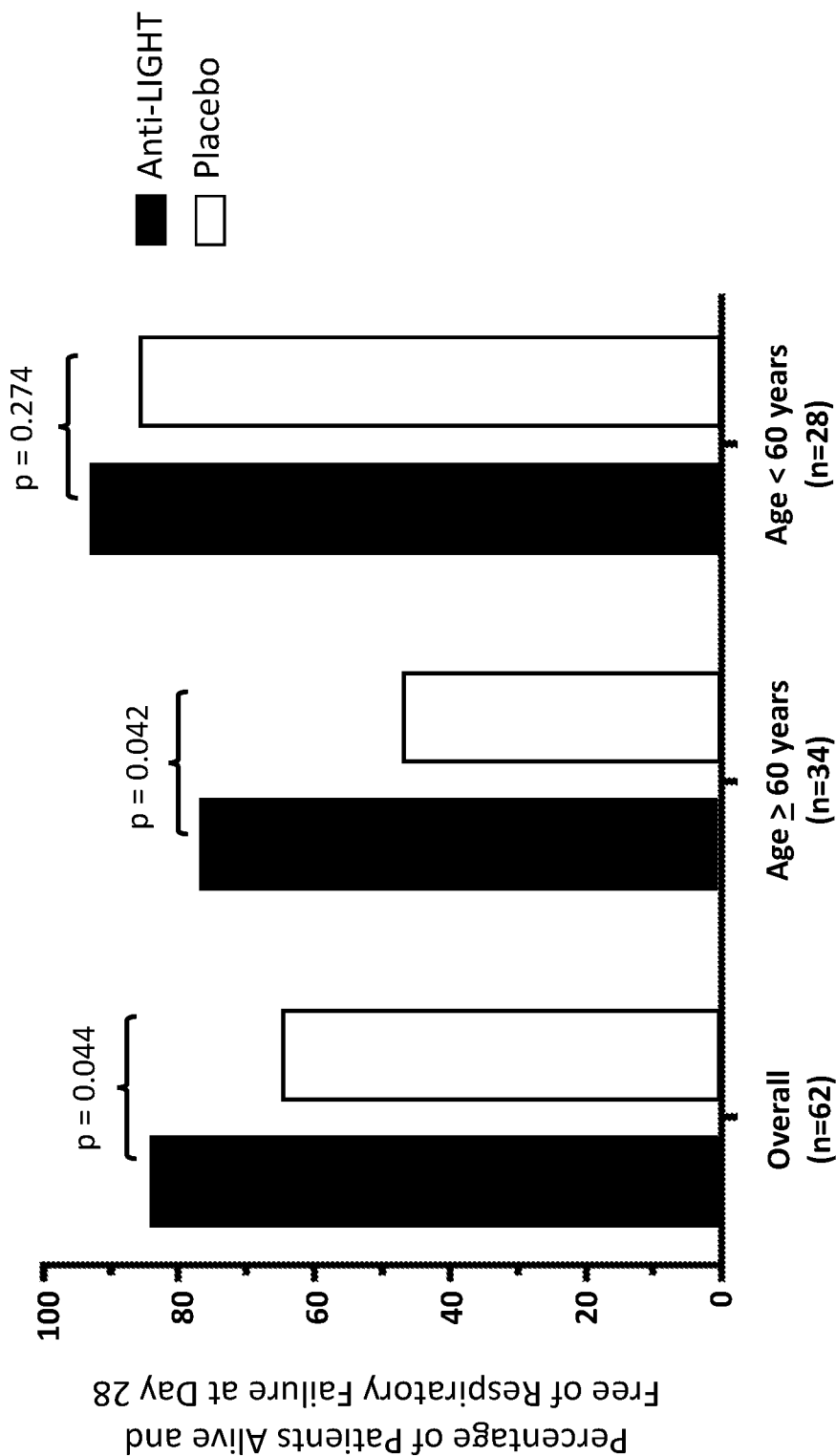
FIG. 10 shows primary endpoint of the study described in Examples 2 and 3: percentage of patients alive and free of respiratory failure at day 28 in the anti-LIGHT monoclonal antibody-treated group compared to the placebo-treated group.

The study demonstrated robust improvement in the primary endpoint (proportion of patients alive and free of respiratory failure over the 28-day study period) compared to placebo in COVID-19 patients with ARDS treated with a single dose of the anti-LIGHT monoclonal antibody at 16 mg/kg (max 1,200 mg) (n=62), as shown in FIG. 10. A prespecified subpopulation of patients greater than or equal to 60 years of age showed similar improvement in the primary endpoint (n=34); efficacy was highest in this subpopulation, the population most vulnerable to severe complications and death with COVID-19 infection. Patients treated with the anti-LIGHT monoclonal antibody in this subpopulation also had a shorter hospital stay compared with placebo treated patients.

Further, due to the protocol allowing patients to receive high flow oxygen prior to randomization, 62 patients were included in the intention-to-treat (ITT) analysis of the primary endpoint. There was a numerical mortality benefit favoring the anti-LIGHT monoclonal antibody with 4 patients dying on active drug and 9 on placebo as of the date of data retrieval.

A single dose of anti-LIGHT monoclonal antibody reduced mortality be ~50% in the study, observed at both the 28-day and 60-day timepoints. 28-day mortality was substantially reduced in patients treated with the anti-LIGHT monoclonal antibody (3 patients) placebo (6 patients). 28-day mortality was 7.7% in patients treated with the anti-LIGHT monoclonal antibody and 14.3% in patients treated with placebo. 60-day mortality was 10.8% in patients treated with the anti-LIGHT monoclonal antibody and 22.5% in patients treated with placebo.

>90% of patients in the study received corticosteroids and >65% received remdesivir. Thus the anti-LIGHT monoclonal antibody showed statistically significant efficacy on top of corticosteroids and standard of care in COVID-19 ARDS.

Figure 9:
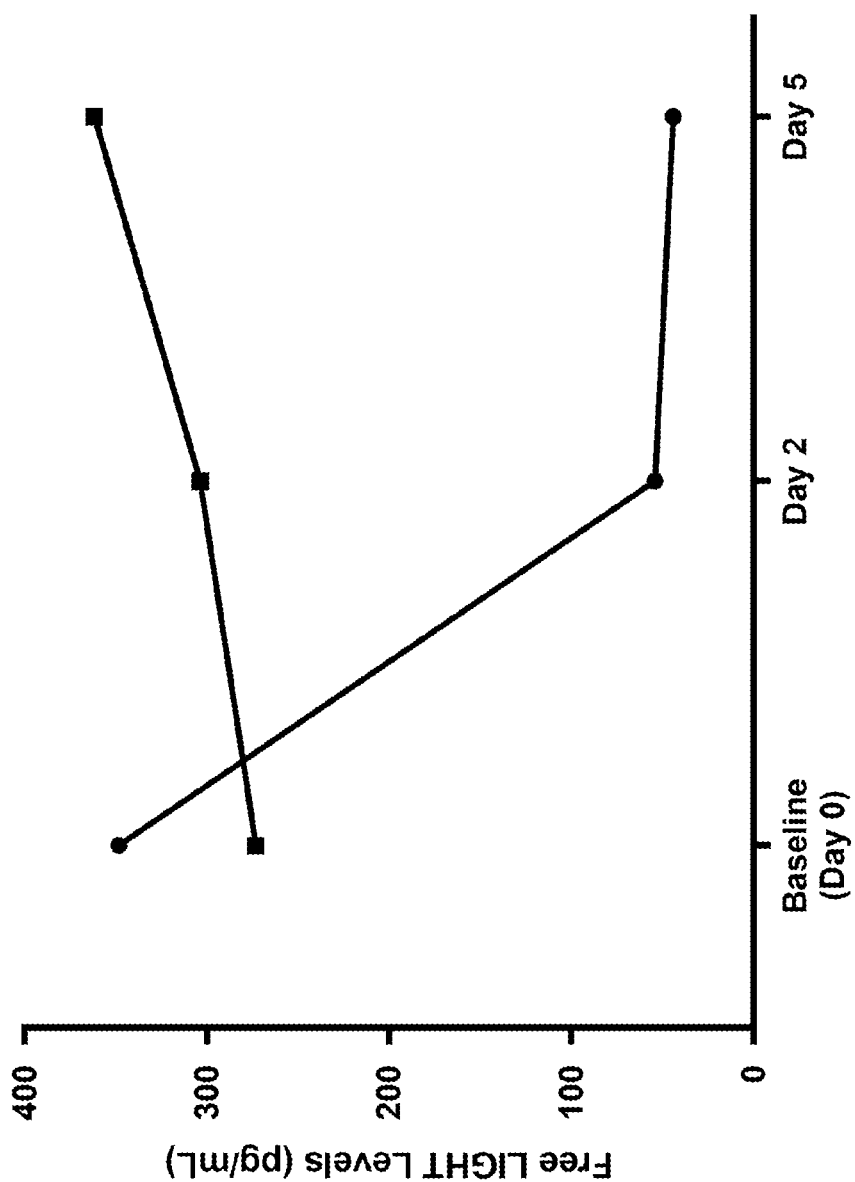
FIG. 9 shows serum free LIGHT levels were compared in subjects in the study described in Examples 2 and 3. Square boxes are subjects treated with placebo (n=34), circles are subjects treated with the anti-LIGHT monoclonal antibody (n=36). Mean free LIGHT levels were comparable at baseline across cohorts. Mean free LIGHT levels reduced dramatically by day 1 after treatment with the anti-LIGHT antibody, but increased in the placebo treated group. Mean free LIGHT levels were about 100 µg/mL higher in the patients ≥60 years-old. The pharmacodynamic effect was on top of standard of care where approximately 90% of patients received systemic corticosteroids.

The anti-LIGHT monoclonal antibody dramatically and rapidly reduced serum free-LIGHT levels in these patients (about 85% reduction in free LIGHT in one day). See FIG. 9, where square boxes are subjects treated with placebo, circles are subjects treated with the anti-LIGHT monoclonal antibody. Table 8 shows LIGHT levels over time for patients in the study who received placebo (n, mean, SD, min and max), and Table 9 shows LIGHT levels over time for patients in the study who received the anti-LIGHT monoclonal antibody (n, mean, SD, min and max).

TABLE 8

LIGHT Levels for Patients Treated With Placebo

| Day | n | Mean | SD | Min | Max |
|---|---|---|---|---|---|
| 1 | 39 | 276.025641 | 204.181741 | 37 | 843 |
| 2 | 38 | 303.421053 | 195.424366 | 73 | 760 |
| 5 | 22 | 349.045455 | 187.021129 | 130 | 897 |
| 8 | 12 | 427.25 | 285.03688 | 98 | 932 |
| 9 | 13 | 459.307692 | 346.335672 | 86 | 1240 |
| 14 | 8 | 685.625 | 1131.91884 | 95 | 3420 |
| 28 | 19 | 408.157895 | 309.366425 | 71 | 1160 |

TABLE 9

LIGHT Levels for Patients Treated With Anti-LIGHT Mab

| Day | n | Mean | SD | Min | Max |
|---|---|---|---|---|---|
| 1 | 40 | 329.425 | 241.33271931 | 22 | 1050 |
| 2 | 39 | 51.728205128 | 59.143349267 | 5.7 | 360 |
| 5 | 31 | 42.64516129 | 51.900898121 | 5 | 251 |
| 8 | 15 | 57.2 | 60.74678122 | 13 | 239 |
| 9 | 10 | 51.9 | 34.326698388 | 12 | 123 |
| 14 | 4 | 59.75 | 23.514180119 | 27 | 80 |
| 28 | 25 | 24.988 | 13.674255617 | 5.3 | 63 |

Table 10 shows IL-6 levels over time for patients in the study who received placebo (n, mean, SD, min and max), and Table 11 shows IL-6 levels over time for patients in the study who received the anti-LIGHT monoclonal antibody (n, mean, SD, min and max).

TABLE 10

IL-6 Levels for Patients Treated With Placebo

| Day | n | Mean | SD | Min | Max |
|---|---|---|---|---|---|
| 1 | 39 | 18.015384615 | 40.223090308 | 2.85 | 190 |
| 2 | 38 | 10.071052632 | 15.096422664 | 2.85 | 64 |
| 5 | 22 | 17.904545455 | 26.750664919 | 2.85 | 110 |
| 8 | 12 | 28.508333333 | 36.723827002 | 2.85 | 100 |
| 9 | 13 | 59.473076923 | 152.07703313 | 2.85 | 557 |
| 14 | 8 | 35.8 | 42.056042542 | 2.85 | 106 |
| 28 | 19 | 26.507894737 | 54.277297953 | 2.85 | 187 |

TABLE 11

IL-6 Levels for Patients Treated With Anti-LIGHT Mab

| Day | n | Mean | SD | Min | Max |
|---|---|---|---|---|---|
| 1 | 40 | 11.855 | 19.83956097 | 2.85 | 117 |
| 2 | 39 | 9.341025641 | 17.152109245 | 2.85 | 84 |
| 5 | 31 | 12.191935484 | 21.311671672 | 2.85 | 93 |
| 8 | 15 | 11.123333333 | 10.204968444 | 2.85 | 36 |
| 9 | 10 | 12.84 | 9.7115852923 | 2.85 | 29 |
| 14 | 4 | 358.225 | 707.85297026 | 2.85 | 1420 |
| 28 | 25 | 4.992 | 4.6357011336 | 2.85 | 24 |

The anti-LIGHT monoclonal antibody was safe and well tolerated with no appreciable differences in immunosuppression or other SAE between the anti-LIGHT monoclonal antibody and placebo. Specifically, the anti-LIGHT monoclonal antibody was well-tolerated at a single dose of 16 mg/kg; no serious adverse events were attributable to the anti-LIGHT monoclonal antibody; the majority of AEs were judged to be mild or moderate; and there was no evidence of increased infections or adverse events related to immunosuppression (see Table 12 below).

TABLE 12

Adverse Events

| | Anti-LIGHT monoclonal antibody (n = 40) | Placebo (n = 42) |
|---|---|---|
| Subjects with ≥1 AE (%) | 16 (40%) | 21 (50%) |
| Subjects with ≥1 Drug-related AE | 8 (20%) | 6 (14.3%) |
| AEs > 5% | | |
| Leukocytosis | 6 (15%) | 4 (9.5%) |
| Anemia | 4 (10%) | 3 (7.1%) |
| Hepatic enzyme increase | 4 (10%) | 2 (4.8%) |
| Acute kidney injury | 3 (7.5%) | 2 (4.8%) |
| Respiratory failure | 3 (7.5%) | 3 (7.1%) |

Example 4

Free Light Detection Assay Capture of Free Light with Candidate Pair

Simoa™ ultra-high sensitive assay (Myriad RBM) was used to detect and measure free LIGHT with high sensitivity, using Quanterix's fully automated immunoassay platform: Simoa HD-1 Analyzer and single molecule array (Simoa) technology. All incubations take place at room temperature inside the Simoa HD-1 analyzer. Capture antibody conjugated paramagnetic beads were incubated with standards, samples or controls and biotinylated detection antibodies. The beads were then washed and incubated with streptavidin-ß-galactosidase (SßG). After the final wash, the beads were loaded into the Simoa Disc with enzyme substrate, resorufin ß-galactopyranoside (RGP). The fluorescence signals are compared to the standard curve and the quantity of LIGHT Free is determined for each sample. After screening anti-LIGHT antibodies in pairs for sandwich immunoassay, assays with one candidate pair (capture antibody: Enzo ALX-804-841-C100, detection antibody: ProSci RF16062; specific epitopes are not detailed for these antibodies) were performed to test for linearity and specificity.

Linearity is a measure of the analytes acceptable sample dilution, and is measured by the ability to obtain results proportional to the analyte concentration in sample when serially diluted. It showed that samples as diluted as 2-fold, 4-fold, 5-old, 10-fold, 20-fold, 40-fold, 80-fold maintained linearity. Linearity conducted at 1:10, 1:20, and 1:40 is shown in FIG. 1. Linearity conducted at 1:10, 1:20, 1:40, 1:80 is shown in FIG. 2.

Free LIGHT Detecting Antibody Pair, DCR3 Interference

DcR3 interference was tested on the candidate pair Enzo ALX-804-841-C100—ProSci RF16062 (capture—detection). A diluent using containing free LIGHT was used, rather than native free LIGHT in a serum or plasma sample. DcR3 spiked concentration was 10,000 ng/ml and 11 additional lower concentrations. Signal inhibition value was calculated as a signal reduction (mean fluorescence intensity (MFI)) for the Enzo/ProSci pair as shown in FIG. 3. DcR3 exhibits 96.3% of signal inhibition (=(9938-361)/9938) for the candidate pair. This demonstrated that the epitope of free LIGHT for the examined pair overlaps with the epitope of free LIGHT for DcR3. It thus shows that the candidate pair binds free LIGHT.

Free LIGHT Detecting Antibody Pair, DcR3 Interference Comparison

Spike and recovery experiment was performed to assess DcR3 (10 µg/mL) interference on the candidate pair Enzo ALX-804-841-C100—ProSci RF16062 (capture—detection). Serum and plasma samples containing native free LIGHT were incubated with (spiked) and without (unspiked) 150 µg/mL of free LIGHT (LIGHT standard recombinant antigen). Said spiked and unspiked samples were then incubated with DcR3.

The % recovery signal was calculated compared to the control with no interferent based on the MFI data as shown in FIG. 4A. The % recovery signal with the interference is divided by the signal of the control. The signal inhibition value was calculated for unspiked serum 1 (which had the most significant reduction). In the set shown in FIG. 4A, 78% represents the reduction in signal, which is related (100%-% recovery). That is, serum 1's DcR3 recovery is 22%, representing a 78% reduction in signal. In addition, in the group of LIGHT (150 µg/ml) spiked samples (lower panel), sample serum 1 demonstrates 92% inhibition (8% recovery).

Another set of data for the same experiment, but using ProSci RF16062—LSBio LS-C133566-100 (capture—detection) is shown in in FIG. 4B.

Figure 4C:
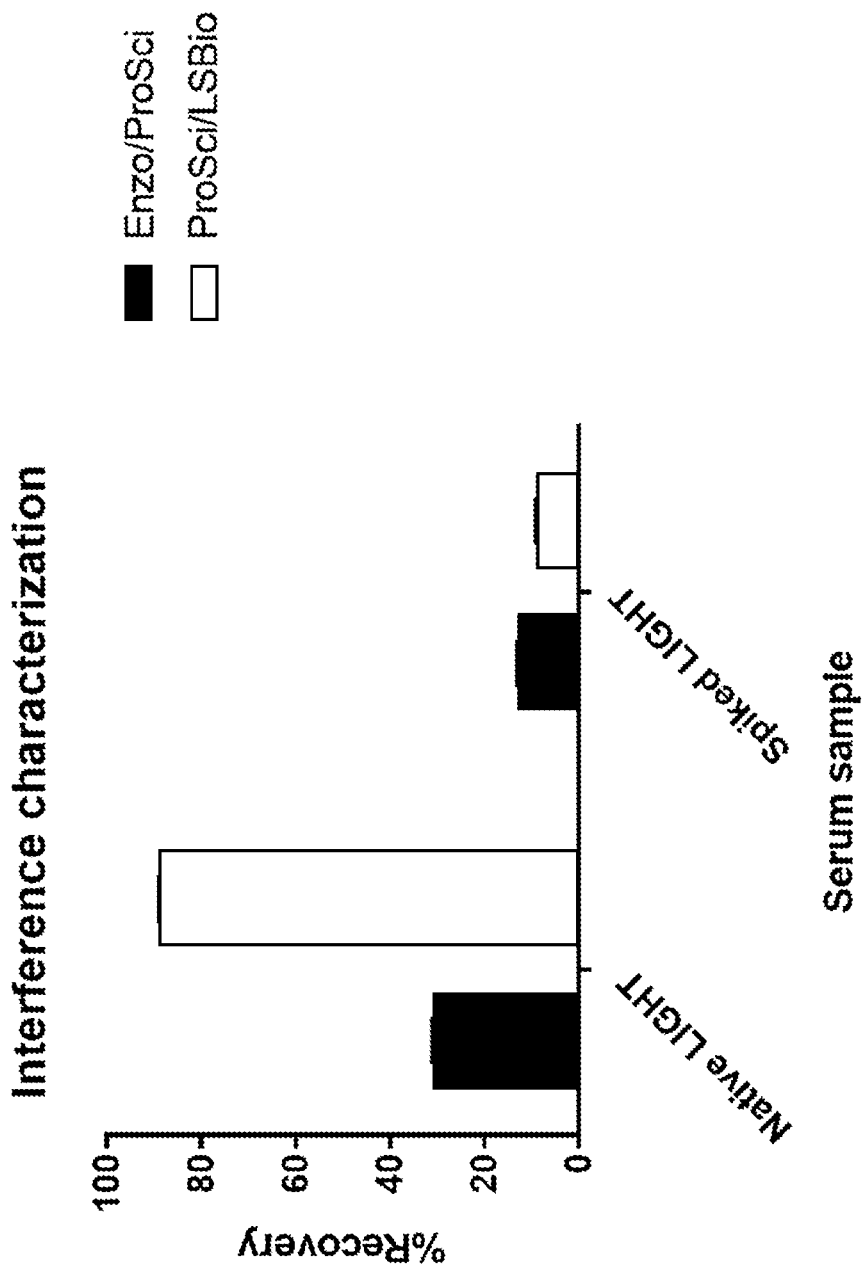

A graph characterizing DcR3 interference with recovery for each candidate pair in native free LIGHT and spiked free LIGHT samples is shown in FIG. 4C. The candidate pair Enzo ALX-804-841-C100—ProSci RF16062 (capture—detection) was identified as a native free LIGHT binder, since it competes with DcR3 and an anti-LIGHT antibody to an extent of above 60% competition. For this pair, serum was a preferable sample to detect free LIGHT compared to plasma. Sensitivity, although not fully characterized yet, implied that samples dilution can be 10-fold, which reduces background. In contrast, the relatively little DcR3 interference with % recovery signal for candidate pair ProSci RF16062—LSBio LS-C133566-100 (capture—detection) indicates the pair does not as effectively bind native free LIGHT, even though both candidate pairs bound to non-native LIGHT standard recombinant antigen to about the same degree.

Assay Validation

The Free LIGHT assay with the free LIGHT binder pair was tested for the assay validation parameters of least detectable dose, lower limit of quantitation, upper limit of quantitation, dynamic range, precision, spike recovery, linearity, matrix interferences, freeze-thaw stability and short-term analyte stability, and met the acceptance criteria for the above listed parameters and reproducibly quantitates free LIGHT levels in serum/plasma samples.

Antibody competition was performed to assess if any unspecific binding occurred. Serum and Plasma samples were incubated with and without 50 µg/mL of capture antibody for 35 minutes at room temperature prior to analysis on the Quanterix HD-1 instrument. Percent recovery was calculated as capture antibody treated (competitive) sample vs. non-treated (control) sample concentration. The % Recovery was all 0%, well within the acceptance criterion of ≤20%.

Example 5

Free Light Levels in Crohn's Disease Samples

Figure 5:
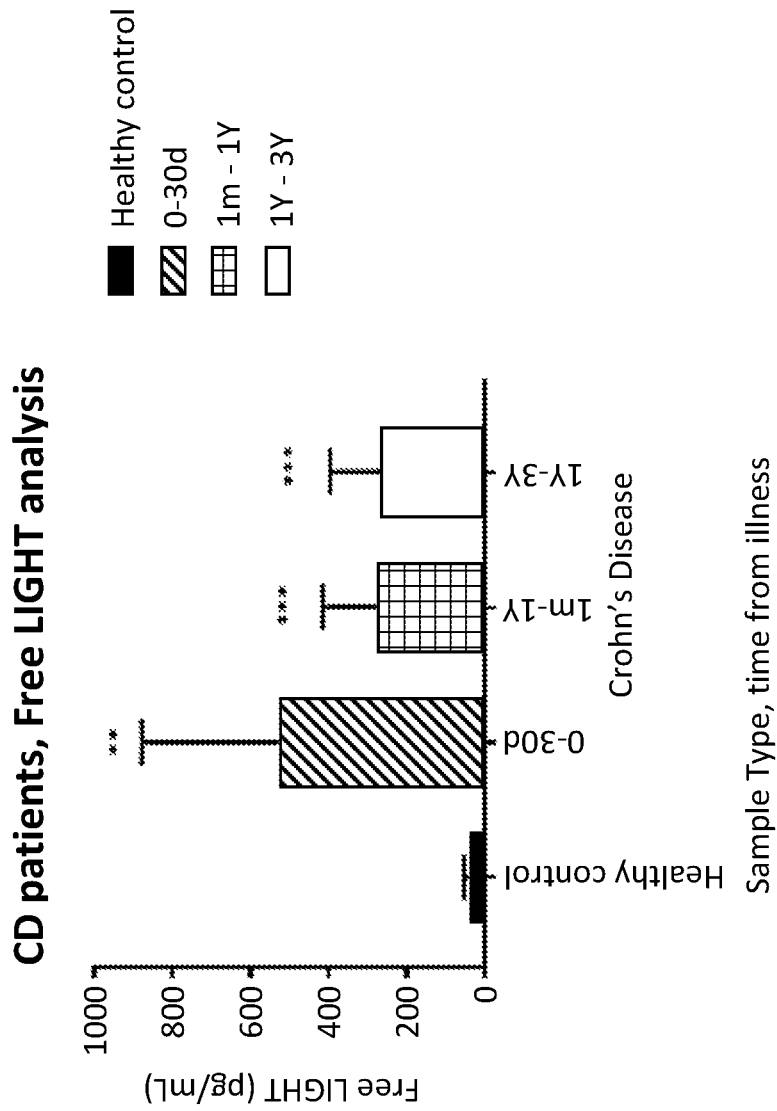
FIG. 5 shows free LIGHT levels in serum samples from 89 Crohn's Disease (CD) subjects were selected and grouped according to time from illness. 89 subjects and 10 healthy controls (gender and age matched) were measured using the free-LIGHT assay described herein using the candidate antibody pair. After excluding outliers, 62 samples and 7 controls were analyzed. Crohn's Disease subjects showed significantly high serum free LIGHT levels (527.93 µg/ml, average in subjects of 0-1 month from illness) than in healthy controls (40.43 µg/ml; P<0.0021). Free LIGHT serum levels also correlated with the disease programs. This suggests that Free LIGHT represents a potential target for the treatment of CD and free LIGHT assay can serve as a companion diagnostic for anti-LIGHT therapy.

FIG. 5 shows free LIGHT levels in serum samples from 89 Crohn's Disease (CD) subjects were selected and grouped according to time from illness. 89 subjects and 10 healthy controls (gender and age matched) were measured using the free-LIGHT assay described herein using the candidate antibody pair. After excluding outliers, 62 samples and 7 controls were analyzed. Crohn's Disease subjects showed significantly higher serum free LIGHT levels (527.93 µg/ml, average in subjects of 0-1 month from illness) than in healthy controls (40.43 µg/ml; P<0.0021). Free LIGHT serum levels also correlated with the disease programs. This suggests that Free LIGHT represents a potential target for the treatment of CD and free LIGHT assay can serve as a companion diagnostic for anti-LIGHT therapy.

Example 6

This study is an escalating dose, open-label, signal-finding study to evaluate the safety, tolerability, and short-term efficacy of an anti-LIGHT monoclonal antibody in adults with moderate to severe active Crohn's Disease who have failed prior treatment with an anti-TNFα agent, with and without loss of function mutations in decoy receptor 3 (DcR3). The anti-LIGHT antibody has a VH of SEQ ID NO. 8, and a VL of SEQ ID NO: 9.

Example 6.1—Study Objectives and Endpoints

The primary objective of this study is to evaluate the safety and tolerability of the anti-LIGHT monoclonal antibody administered by SQ injection to adults with moderate to severe, active CD who have failed prior treatment with an anti-tumor necrosis factor alpha (anti-TNFα) agent.

The secondary objectives of this study are to: estimate plasma concentrations of the anti-LIGHT monoclonal antibody administered by SQ injection to adults with moderate to severe, active CD; and to evaluate response to treatment with the anti-LIGHT monoclonal antibody administered by SQ injection to adults with moderate to severe, active CD.

Example 6.2—Study Design

This is a Phase 1b, multi-center, open-label, dose-escalation, signal-finding study to evaluate the safety, tolerability, PK and short-term efficacy of the anti-LIGHT monoclonal antibody in adults with moderate to severe, active CD who have previously failed anti-TNFα treatment.

Four subjects with Crohn's Disease who satisfy all eligibility criteria are enrolled in each of 2 dose cohorts. The first cohort receives the anti-LIGHT monoclonal antibody 1.0 mg/kg SQ every 14 (q14) days.

Dose escalation proceeds after completion of the first cohort based on review of cumulative safety, tolerability, pharmacokinetic, and efficacy data by Data Monitoring Committee and after a decision is made to progress to the second cohort. The estimated dose escalation for the second cohort is 3.0 mg/kg SQ q14 days, if permitted by safety data review.

Each subject's participation includes a screening period, which if required includes a 12-week wash-out period for subjects receiving biologic treatment or who have received biologic treatment within 12 weeks of the Screening Visit. For subjects requiring wash-out, there is optionally a 1- to 14-day time period between the screening visit and the start of the wash-out period, as necessary. With the exception of subjects requiring wash-out of the biologic certolizumab pegol (Cimzia), only those subjects without detectable biologic levels after 8 weeks of wash-out are allowed to enter the study after confirmation of undetectable levels; all other subjects (including those receiving certolizumab pegol [Cimzia]) are required to complete a full 12-week wash-out period. The wash-out period includes the time period from the last dose received prior to the Screening Visit. Subjects not requiring a biologic wash-out period are allowed to enter the study after review and confirmation of eligibility at screening. Screening is followed by an 8-week, open-label treatment period, and a safety follow-up visit approximately 4 weeks after the last dose. The maximum study duration is 26 weeks.

Study visits occur at screening and on Days 0, 7, 14, 21, 28, 35, 42, 49 and 56. The safety follow-up visit occurs on Day 84. The Schedule of Assessments is shown in Table 13.

TABLE 13

Schedule of Assessments

| Assessment or Procedure | Screening Period | | | | Open-Label Treatment Period | | | | | | | | | Safety Follow-up Visit 11 |
|---|---|---|---|---|---|---|---|---|---|---|---|---|---|---|
| | Visit 1 Week- 14 to-12 | Initial Phone Contact[a] | Visit for Testing Previous Biologics (if required) | Wash-out Phone Contact[b] | Visit 2[c] Pre-dose Day 0 | Visit 2[c] Dosing and Post-dose Day 0 | Visit 3 Day 7 | Visit 4 Day 14 | Visit 5 Day 21 | Visit 6 Day 28 | Visit 7 Day 35 | Visit 8 Day 42 | Visit 9 Day 49 | Visit 10/ET Visit Day 56 | Day 84 or 28 days after ET visit |
| Informed consent | X | | | | | | | | | | | | | | |
| Inclusion/exclusion criteria review | X | X | | | X | | | | | | | | | | |
| Testing for Previous Biologics | | | X[q] | | | | | | | | | | | | |
| Genotyping for DcR3 genes | X | | | | | | | | | | | | | | |
| Demographics/medical history[d] | X | | | | | | | | | | | | | | |
| Physical examination, incl. weight[e] | X | | | | X | | | X | | X | | X | | X | |
| Vital signs (BP, pulse, RR, T)[f] | X | | | | X | X | | X | | X | | X | | X | |
| TB testing[g] | X | | | | | | | | | | | | | | |
| 12-lead ECG | X | | | | | | | | | X | | | | X | |
| Clinical laboratory assessments[h] | X | | | | X | | | X | | X | | X | | X | |
| PK blood sampling[i] | | | | | X | | X | X | X | X | X | X | X | X | X |
| Blood draws for exploratory analyses[j] | | | | | X | | | | | X | | | | X | |
| Anti-drug antibody assessment | | | | | X | | | X | | X | | | | X | X |
| Urinalysis | X | | | | X | | | | | X | | | | X | |
| Pregnancy testing (females of childbearing potential)[k] | X | | | | X | | | | | X | | | | X | |
| Urine drug screen[l] | X | | | | | | | | | | | | | | |
| Stool sample[m] | X | | | | | | | | | X | | | | X | |
| CDAI | X | | | | X | | | X | | X | | X | | X | |
| IBD-Q | X | | | | X | | | | | | | | | X | |
| Endoscopy with biopsy and histology[n] | X | | | | | | | | | | | | | X | |
| Adverse event monitoring[o] | X | X | X | X | X | X | X | X | X | X | X | X | X | X | X |
| Concomitant medications | X | X | X | X | X | X | X | X | X | X | X | X | X | X | X |
| Provide/reconfirm access to subject diary (US sites) | X | | | | X | | X | X | X | X | X | X | X | X | |

TABLE 13-continued

| | | | | | | | | | | | | |
|---|---|---|---|---|---|---|---|---|---|---|---|---|
| Provide diary (ex-US sites) | X | | X | | X | X | X | X | X | X | X | X |
| Subject diary reviewed for completeness | | | X | | X | X | X | X | X | X | X | X |
| Assess individual subject stopping criteria | | | | X | X | X | X | X | X | X | X | X |
| Anti-LIGHT monoclonal antibody administration (on-site)[p] | | | | X | | X | | X | | X | | |

[a] Telephone visit is conducted for confirmation of eligibility and, as needed, initiates wash-out of current anti-TNFα treatment. If the subject is not receiving biologic treatment, they begin completing the subject diary and have visit 2 scheduled >7 days from the initial phone contact. The diary is completed up to the time of the visit.
[b] Telephone visit is conducted for confirmation whether additional wash-out time is required following receipt and review of the laboratory results. If the concentration level is not detectable, the subject begins completing the subject diary and has visit 2 scheduled >7 days from the washout phone contact. If the concentration level is detectable, the subject completes the full 12 week wash-out. Upon completion of the washout period, the subject begins completing the diary and has visit 2 scheduled >7 days from the end of the washout. The diary is completed up to the time of the visit.
[c] After Day 0 (Visit 2), visits at which the anti-LIGHT monoclonal antibody is administered occur every 14 ± 3 days. These visits are scheduled relative to Day 0 (Visit 2), which is the baseline visit.
[d] Medical history includes details regarding all CD-related surgical procedures and hospitalizations.
[e] A complete physical examination is performed at Visits 1, 2, 6, and 10/ET. Brief physical examinations are done at Visits 4 and 8. Height is measured at V2 only.
[f] Vitals are taken pre-and post-dose on Visit 2, 4, 6 and 8. Post-dose vitals are taken at least 60 minutes post-dose, immediately prior to discharge.
[g] TB testing includes QuantiFERON-TB Gold (QFT) blood testing or PPD skin testing. If the subject's PPD tine skin test is ≥5 mm, a chest x-ray is also be employed for TB assessment.
[h] Clinical laboratory assessments at Visits 1, 6, and 10/ET include: CBC with differential, hematology, serum albumin, CRP, liver panel, GGT. Anti-drug antibodies are measured at Visits 2, 6 and 10. Clinical laboratory assessments at Visits 2, 4, and, 8 include hematology and serum albumin.
[i] Pre-dose PK blood samples are obtained within 60 minutes prior to dose at Visits 2, 4, 6 and 8.
[j] Exploratory analyses examined LIGHT, cytokines, RNA sequencing, and flow cytometry.
[k] Serum β-hCG is conducted at Visit 1 and Urine β-hCG tests are conducted on Visits 2, 6 and 10.
[l] Screening for amphetamines, barbiturates, benzodiazepines, cocaine, opiates, phencyclidine, cannabinoids, propoxyphene, and methadone as warranted.
[m] Stool samples are obtained at Visits 1, 6 and 10/ET. C. difficile test is performed only at Visit 1. Fecal calprotectin is measured at all specified visits.
[n] Histological confirmation of disease is performed only at Visit 1. Documentation is provided to site for confirmation. Exploratory biomarker histology is completed for samples provided to study central laboratory provider.
[o] Adverse event monitoring begins at the time informed consent is signed.
[p] Subjects are required to remain in the clinic for at least 60 minutes after the anti-LIGHT monoclonal antibody administration for adverse event monitoring.
[q] Subjects requiring wash-out have a blood test performed at 8 weeks after the start of the wash-out period to confirm the previous biologic therapy is undetectable. If there is no previous biologic therapy detected, subjects continue onto Visit 2 and are not required to complete the full 12-week wash-out. If there are detectable levels of the previous biologic therapy, then subjects complete the full 12-week wash-out before proceeding to Visit 2. For subjects receiving certolizumab pegol (Cimzia) a 12-week wash-out is required.
BP = blood pressure;
CBC = complete blood count;
CDAI = Crohn's Disease Activity Index;
CRP = C-reactive protein;
DcR3 = decoy receptor 3;
GGT = gamma-glutamyl transferase;
ECG = electrocardiogram;
ET = early termination;
hCG = human chorionic gonadotropin;
LIGHT = Lymphotoxin-like, exhibits Inducible expression, and competes with Herpes Virus Glycoprotein D for Herpesvirus Entry Mediator, a receptor expressed by T lymphocytes;
PK = pharmacokinetic;
PPD = purified protein derivative;
RR = respiration rate;
T = temperature;
TB = tuberculosis;
TNFα = tumor necrosis factor alpha Study Periods The study includes a screening period, an open-label treatment period, and a safety follow-up visit. The 1.0 mg/kg dose cohort completes the study periods described below. Following a review of the safety data, a decision is made.

Screening Period

During the screening period (Week −14 to Day 0), all subjects are evaluated for their eligibility to participate in the study. At Visit 1, subjects sign the informed consent form before any study-related procedures or evaluations are conducted.

Demographic information is obtained along with medical history, including CD diagnostic information, CD-related procedures/surgeries and medication use history. Any existing conditions reported at the screening visit are recorded in the electronic case report form (eCRF); current medications are also recorded on the eCRF. Prior CD therapies (lifetime recall) are recorded in the eCRF with dates reflecting prior use. All safety assessments are conducted, including physical examinations (with weight measurements), vital signs (blood pressure, pulse, respiration rate and temperature), 12-lead ECGs, clinical laboratory tests, stool sample and urinalysis. A urine drug screening test (as warranted) and tuberculosis (TB) testing defined as either a purified protein derivative (PPD) skin reaction test or QuantiFERON-TB Gold (QFT) blood test, and as required by protocol, chest x-ray, are administered to all subjects. A serum β-human chorionic gonadotropin (β-hCG) test is to be administered to females of childbearing potential. The CDAI and the Inflammatory Bowel Disease Questionnaire (IBD-Q) are administered. Subjects undergo an endoscopy with biopsy and histology during the screening period. Subjects are provided access to a study diary (electronic or hard copy) to record their daily assessment of well-being, abdominal pain and stool frequency including loose and watery stools. The diary is completed for a minimum of 7 days immediately prior to initiation of open-label treatment as described in Table 13. Subjects record frequency of loose or watery stools and assess overall abdominal pain for each day. Finally, adverse events (AEs) are monitored.

Subjects who are taking a biologic treatment or who have received biologic treatment within 12 weeks of the Screening Visit but who are otherwise eligible for study participation based on review of all screening evaluations and results begin a wash-out period for these medications. With the exception of subjects requiring wash-out of the biologic certolizumab pegol (Cimzia), a blood test is administered to subjects undergoing wash-out 8 weeks after their last dose of biologic treatment to ensure that serum levels of any previous biologic treatments are below the level of detection. If it is confirmed that the levels of previous biologic treatment are undetectable, then the subject proceeds to Visit 2. If the test results indicate that the previous biologic treatment is detectable, the subject is required to complete a full 12-week wash-out period before proceeding to Visit 2. For subjects receiving the biologic certolizumab pegol (Cimzia) a 12-week wash-out is required.

Open-Label Treatment Period

Eligible subjects return to the clinic after the screening period (and wash-out period, if applicable) on Visit 2, which is Day 0 of the 8-week, open-label treatment period. Physical examinations including weight and vital sign assessments, clinical laboratory tests, urinalysis, and the CDAI are performed. A urine β-hCG test is administered to females of childbearing potential. Any AEs and concomitant medications are recorded. Blood is drawn for PK, ADA and exploratory analyses (including LIGHT, cytokines, RNA sequencing, and flow cytometry). Subjects record their daily assessment of well-being, abdominal pain and stool frequency including loose and watery stools in their study diary. Diary data is reviewed for completeness during each visit. Subjects are re-evaluated to determine whether they meet all inclusion criteria and do not satisfy any of the exclusion criteria.

Eligible subjects are then enrolled in the study and receive their first dose of the anti-LIGHT monoclonal antibody in the clinic. Subjects receive the anti-LIGHT monoclonal antibody as a SQ injection in the abdomen in a zone of 4 to 10 cm from the umbilicus with the injection site rotated with each subsequent dose. The dose of the anti-LIGHT monoclonal antibody is administered every 14 days (±3 days) for 8 weeks. Subjects are monitored for AEs during the administration of each dose and for 60 minutes after dosing.

Subject enrollment within a cohort is staggered by at least one day, in order to assess any delayed adverse events.

Subjects return to the clinic every 14 (±3) days (Visits 4, 6, 8, and 10) after the first anti-LIGHT monoclonal antibody dose for assessment of safety, PK, and efficacy and to receive the next dose of investigational product, as shown in Table 13. Additional weekly visits between dosing visits (Visits 3, 5, 7, and 9) occur at which time blood are drawn for PK analyses, subjects are provided access to a study diary (electronic or hard copy) for diary data collection, and AEs and concomitant medication use are recorded.

Prior to enrolling subjects in the second dose cohort, all subjects in the first cohort complete their participation in the study and safety data from those subjects is reviewed by the Data Monitoring Committee. A recommendation is provided by the DMC and a decision is made by the Sponsor as to whether subjects can be enrolled in the next dose cohort.

Safety Follow-up Visit

Approximately 28 days after the final dose, subjects have a safety follow-up visit. The safety follow-up visit is conducted in the clinic with the subject. Any AEs that occur in the time since the subject's last anti-LIGHT monoclonal antibody dose are recorded, along with any concomitant medication use.

Safety Data Review

Each investigator reviews all available safety data collected at their site on a weekly basis, and communicates any safety concerns to the sponsor medical monitor. The sponsor medical monitor reviews all relevant safety findings with the coordinating principal investigator and DMC as needed.

Special attention is paid to adverse drug reactions observed in the anti-LIGHT monoclonal antibody preclinical study as well as other common adverse reactions seen with other biologic treatments which include injection site reactions for the anti-LIGHT monoclonal antibody during preclinical observation. Special attention is paid to adverse reactions observed with other biologic treatments, which include: potential for increased infection including opportunistic infections (such as tuberculosis); hypersensitivity reactions (including anaphylaxis); immunogenicity; malignancy; impaired immunization; and CD exacerbation.

Data Monitoring Committee

An external, independent Data Monitoring Committee (DMC) comprising physicians, scientists and a biostatistician review the study data at regular intervals for the duration of the study which includes a meeting after the completion of each cohort and ad hoc meetings to assess individual exacerbations of Crohn's Disease meeting Common Terminology Criteria for Adverse Events (CTCAE) Grade 3 or greater. The DMC's role is to protect the interests of the subjects in the study and those still to be entered in the study by reviewing cumulative safety, tolerability, pharmacokinetic and efficacy data. The DMC's meeting schedule may be adjusted based on recommendations made by the DMC, the amount of incremental safety data, and other practical considerations. The data provided to the DMC may not be monitored and is not considered "clean" until the database is locked at the completion of the study.

Possible outcomes of the DMC review can include one of the following recommendations: study can continue; study can continue with modifications; and study is to be terminated.

Data Monitoring Committee recommendations are documented in meeting minutes which include, at a minimum: a list of meeting participants; a summary of data considered during the meeting; and a summary of the DMC recommendation regarding further dose cohorts, including any concerns raised.

The sponsor is responsible for the decision to continue, modify or terminate the study. A copy of the DMC meeting recommendation and sponsor decision are sent to the study sites upon completion and prior to administration of the next subject dose or initiation of the next cohort.

Individual Subject Stopping Criteria

The following individual subject stopping criteria are used during the study and are assessed starting post-dose at Visit 2. The individual subject is stopped from the study if the subject develops a CTCAE Grade 3 or higher of the following: injection site reactions; opportunistic infections (i.e., tuberculosis); hypersensitivity reactions (e.g. allergic reactions, anaphylaxis or cytokine release syndrome); malignancy; decreased white blood cell count; decreased neutrophil count; decreased platelets; colonic or ileal hemorrhage; colonic, ileal or small intestine obstruction; colonic, ileal or small intestine perforation; and colonic, ileal or small intestine stenosis.

A subject is also to be stopped if liver enzymes are: ALT or AST >8×ULN; ALT or AST >5×ULN for more than 2 consecutive weeks or; a single subject ALT or AST >3× ULN with the appearance of fatigue, nausea, vomiting, right upper quadrant pain or tenderness, fever, rash and or eosinophilia (>5%). Note that subjects who exhibit ALT or AST >3×ULN without appearance of any of the above symptoms are required to have repeat testing within 48-72 hours to confirm abnormality and determine direction (increase or decrease) from the original value. A subject is stopped if Hy's Law is detected (i.e. ALT or AST >3×ULN and total bilirubin >2×ULN and no other reason can be found to explain the combination of increased AT and TBL, such as viral hepatitis A, B, or C; preexisting or acute liver disease; or another drug capable of causing the observed injury).

Study Stopping Criteria

The following study stopping criteria are used during the study. The study is stopped if two or more subjects develop the same CTCAE Grade 3 or if one subject develops a CTCAE Grade 4 of the following: injection site reactions; opportunistic infections (i.e. tuberculosis); hypersensitivity reactions (e.g. allergic reactions, anaphylaxis or cytokine release syndrome); malignancy; decreased white blood cell count; decrease neutrophil count; or decreased platelets. The study is stopped if two individual subjects develop any of the following liver toxicities: ALT or AST >8×ULN; ALT or AST >5×ULN for more than consecutive 2 weeks; or ALT or AST >3×ULN with the appearance of fatigue, nausea, vomiting, right upper quadrant pain or tenderness, fever, rash and or eosinophilia (>5%).

The study is stopped if one subject meeting Hy's Law is detected (i.e. ALT or AST>3×ULN and total bilirubin >2×ULN and no other reason can be found to explain the combination of increased AT and TBL, such as viral hepatitis A, B, or C; preexisting or acute liver disease; or another drug capable of causing the observed injury).

Individual reports of exacerbations of Crohn's Disease CTCAE Grade 3 or greater, such as: colonic or ileal hemorrhage; colonic, ileal or small intestine obstruction; colonic, ileal or small intestine perforation; or colonic, ileal or small intestine stenosis are reviewed by the DMC at the first available date after report to determine if modifying the study or stopping the study is recommended.

Study Design Rationale

This is the second study in which the anti-LIGHT monoclonal antibody is administered to human subjects and the first study in subjects with treatment-resistant CD. The study is a pilot study using a dose-escalation design to characterize the safety and tolerability of 2 different doses of the anti-LIGHT monoclonal antibody (1.0 mg/kg and 3.0 mg/kg) in the target population. The dose escalation design allows for the evaluation of safety and tolerability in small numbers of subjects before proceeding to the next dose level. The open-label administration of the anti-LIGHT monoclonal antibody to all enrolled subjects minimizes the number of subjects exposed to the study procedures. The inclusion of PK blood draws and efficacy assessments allowed for preliminary assessments of plasma levels and efficacy, respectively.

No specific hypotheses are being tested in this pilot study. All data are to be summarized using descriptive statistics as appropriate.

Number of Subjects

Four subjects are enrolled in each of the 2 planned dose cohorts for a maximum of 8 study subjects. Subjects who withdraw from the study prematurely prior to a third dose are permitted to be replaced.

Treatment Assignment

The first cohort of subjects are assigned to the 1.0 mg/kg dose of the anti-LIGHT monoclonal antibody. Subjects are assigned to the second dose cohort, after the DMC review of the safety data from the first cohort, and provided study stopping criteria are not met.

Subject Inclusion Criteria

Subjects that meet all of the following inclusion criteria are eligible for enrollment in the study:

1. Subject is able to speak English fluently and provided written informed consent for this study.
2. Subject is male or female, >18 to 75 years of age.
3. Subject has a documented diagnosis of CD via endoscopy/colonoscopy and hi stologicalconfirmation.
4. Subject has moderate to severe, active CD as evidenced by Simple Endoscopy Score for Crohn's Disease (SES-CD) score of ≥7 and histological confirmation.
5. Subject has failed treatment with an approved therapeutic dose of an anti-TNFα monoclonal antibody treatment with either no initial response (primary non-responder) or an initial response to induction with subsequent lost response (secondary non-responder) as defined below.
6. Subject is permitted to receive concurrent treatment with an oral corticosteroid, and/orazathioprine or 6-mercaptopurine (6-MP) or methotrexate (MTX).
7. Subject agrees to be genotyped at the DcR3 locus.

A primary non-responder is defined as a subject for whom treatment with infliximab, adalimumab, or certolizumab pegol produced an inadequate initial response. Inadequate initial response symptom details occur >2 weeks after the last dose of induction therapy. The algorithm for defining inadequate initial response is shown below. Subjects categorized as primary non-responders meet both parts of the algorithm. Documentation required includes dates and doses of failed induction therapy and lack of response details around disease activity recorded by a treating clinician.

The following algorithm is used for inadequate initial response to current or prior therapy with infliximab, adalimumab, or certolizumab pegol. The subject has received induction doses of either infliximab (2 or 3 doses of >5 mg/kg), adalimumab (dose of 160 mg followed by a dose of >80 mg or, dose of 80 mg followed by a dose of >40 mg), or certolizumab pegol (2 or 3 doses of >400 mg); and the subject did not initially respond to these induction doses as documented by the presence of at least 1 of the following signs or symptoms related to Crohn's Disease activity: lack of improvement or worsening in stool frequency; lack of improvement or worsening in daily abdominal pain; occurrence, lack of improvement, or worsening of fever associated with Crohn's Disease; recurring drainage from a previously non-draining fistula or development of a new draining fistula; lack of improvement or worsening in rectal bleeding; or initiation or increase in antidiarrheal medication.

A secondary non-responder is defined as a subject for whom treatment with infliximab, adalimumab, or certolizumab pegol produced an initial response followed by a loss of response. Loss of response details occurs >2 weeks after last dose of maintenance therapy. The algorithm for defining loss of response is described below. Subjects categorized as secondary non-responders meet both parts of the algorithm. Documentation required includes dates and doses of induction and maintenance, initial response and subsequent loss of response including details around disease activity recorded by a treating clinician. The following is the algorithm for loss of response to prior therapy with infliximab, adalimumab, or certolizumab pegol. The subject responded to induction therapy at doses described above and received at least 2 maintenance doses of: infliximab (>5 mg/kg), adalimumab (dose >40 mg or, if failed as a pediatric dose of >20 mg), or certolizumab pegol (>400 mg); and the subject did not respond to these maintenance doses as documented by the presence of at least 1 of the following signs or symptoms related to Crohn's Disease activity: worsening in stool frequency; worsening in daily abdominal pain; occurrence, or worsening of fever associated with Crohn's Disease; recurring drainage from a previously non-draining fistula or development of a new draining fistula; worsening in rectal bleeding; or initiation or increase in antidiarrheal medication.

Subject Exclusion Criteria

Subjects who meet any of the following exclusion criteria are not eligible for enrollment in the study:

1. Subject has a diagnosis of ulcerative colitis (UC) or indeterminate colitis.
2. Subject is unable to tolerate or unwilling to undergo study procedures including endoscopy and biopsy during the study.
3. Subject has signs or symptoms of bowel obstruction with small bowel imaging supporting obstruction.
4. Subject has short bowel syndrome as determined by the investigator.
5. Subject has a current functional colostomy or ileostomy.
6. Subject had a surgical bowel resection within the past 6 months prior to screening or is planning any resection during the study period.
7. Clinical suspicion of intra-abdominal abscesses exist, in the opinion of the investigator.
8. Subject has concurrent bowel dysplasia or a history of bowel dysplasia in the 5 years prior to screening.
9. Subject has a known, active and/or positive test for *C. difficile* infection.
10. Subject has history of or current diagnosis of any cancer excluding cancers that have been cured by surgical excision (e.g., non melanoma skin cancers).
11. Subject has a history of a lymphoproliferative disorder, including lymphoma, or signs and symptoms suggestive of lymphoproliferative disease at any time.
12. Subject has history of or active TB infection or positive TB testing at screening.
13. Subject has known concurrent viral hepatitis, or acquired immune deficiency syndrome (AIDS) or known human immunodeficiency virus (HIV) infection.
14. Subject has been treated with natalizumab (TYSABRI®).
15. Subject has not completed his/her primary vaccination series (particularly hepatitis B, varicella, measles/mumps/rubella) unless immunity documented with blood titers.
16. Subject received any live attenuated vaccine, such as varicella-zoster, oral polio, orrubella, within 3 months prior to the baseline visit.
17. Subject has any of the following abnormal screening laboratory test results: clinically significant ECG abnormalities; aspartate transaminase (AST), alanine transaminase (ALT) or total bilirubin >ULN; hemoglobin <10 g/dL; absolute neutrophil count <1500 cell/mm$^3$, or; estimated glomerular filtration rate <60 mL/min/1.73 m$^2$.
18. Subject has abnormal vital signs during Screening (Visit 1) or prior to enrollment at the baseline visit (Visit 2).
19. Subject is pregnant or a nursing mother.
20. Subject is sexually active and not on effective contraception.
21. Subject has a history of drug abuse that may inhibit participation in the clinical study.
22. Subject has a current or recent history (within 6 months prior to screening) of significant and severe renal, hepatic, hematological, gastrointestinal (other than CD or conditions outlined above), endocrine, pulmonary, cardiac, or neurological disease.
23. Subject has any other clinically significant mental or physical illness or infection that, in the opinion of the investigator, might confound the results of the study, pose additional risk to the subject by their participation, or prevent or impede the subject from completing the study.
24. There is any concern on the part of the investigator regarding the subject's safety, compliance, or suitability with respect to his/her participation in the study.

Screen Failure

Subjects who fail inclusion and/or exclusion criteria are allowed be rescreened for the study with the prior approval of the sponsor's medical monitor. In the event of a rescreening, the first screening visit is entered into the eCRF as the Screening Visit (Visit 1) and the repeat assessments are entered into the eCRF as an unscheduled visit.

Subject Withdrawal Criteria

All subjects are advised that they are free to withdraw from participation in this study at any time, for any reason, and without prejudice. The investigator makes every reasonable attempt to keep subjects in the study; however, subjects are withdrawn from the study if they withdraw consent to participate. For subjects who fail to attend scheduled visits, the investigator attempts to contact them by telephone or other means to exclude the possibility of an AE being the cause of withdrawal. Should that be the cause, the AE is documented, reported, and followed.

The sponsor reserves the right to request the withdrawal of a subject due to protocol violations or other reasons.

The investigator also has the right to withdraw subjects from the study at any time for lack of therapeutic effect that is intolerable or otherwise unacceptable to the subject, for intolerable or unacceptable AEs, intercurrent illness, for meeting the individual subject stopping criteria, noncompliance with study procedures, administrative reasons, or in the investigator's opinion, to protect the subject's best interests.

If a subject is withdrawn before completing the study, the reason for withdrawal and the date of discontinuation are recorded on the appropriate eCRF. Whenever possible and reasonable, the evaluations that are conducted at the completion of the open-label treatment period (i.e., Visit 10) are performed at the time of early termination.

Subjects who withdraw prior to receiving the third dose of study drug, if any, are allowed to be replaced.

All samples are retained according to applicable rules and regulations. Blood and biopsy samples are stored and used for further analysis related to this research. Saliva samples are allowed to be used for purposes related to this research. Samples are given a unique code that includes no information that names the subject. Any remaining DNA samples are stored for future biomarker studies.

Example 6.3—Treatment of Subjects

Description of Investigational Product

Subjects in each dose cohort receive the investigational product as a single SQ injection in the abdomen in a zone of 4 to 10 cm from the umbilicus with the injection site rotated with each subsequent dose. The dose of the anti-LIGHT monoclonal antibody is administered on Days 0, 14, 28, and 42. After Day 0, injections occur within ±3 days of the scheduled 14-day intervals.

Subjects in the first dose cohort receive the anti-LIGHT monoclonal antibody 1.0 mg/kg for the entire 8-week, open-label treatment period. Data from this cohort are reviewed, after all subjects have completed the treatment period and its associated assessments and before the second cohort is enrolled. It is anticipated that there are a minimum of 2 weeks between subject last visit and the review of cumulative safety, tolerability, pharmacokinetic and efficacy data.

Eligible subjects in the second dose cohort receive the anti-LIGHT monoclonal antibody 3.0 mg/kg for the entire 8-week, open-label treatment period. Data from the second cohort are reviewed, after all subjects have completed the treatment period and its associated assessments.

Any quality issue noticed with the receipt or use of an investigational product provided by the sponsor (deficiency in condition, packaging, appearance, pertaining documentation, labeling, expiration date, etc.) is promptly communicated to the sponsor, who investigates.

A potential defect in the quality of investigational product provided by the sponsor may be subject to initiation of a recall procedure by the sponsor. In this case, the investigator is responsible for promptly addressing any request made by the sponsor, in order to recall the investigational product and eliminate potential hazards.

Permitted and Prohibited Therapies

All prior lifetime CD therapies as well as concomitant medications used (including over-the-counter medications and herbal supplements) are recorded in the source document and on the appropriate eCRF.

Permitted Therapies

Subjects are permitted to receive concurrent treatment with an oral corticosteroid, and/or azathioprine, 6-MP or MTX. Subjects are not allowed to have their dose of these medications increased during the study. If a dose increase of a concomitant permitted therapy is required, the subject is discontinued from the study utilizing the Early Termination visit procedures. Concurrent treatment with an oral corticosteroid, and/or azathioprine, 6-MP or MTX is defined as follows: Oral corticosteroid—Prednisone dose not exceeding 40 mg/day, with a stable dose for at least 2 weeks prior to baseline; Azathioprine or 6-MP—Azathioprine dose of at least 2 mg/kg/day or 6-MP dose of 1 to 1.5 mg/kg/day rounded to the nearest available tablet formulation, or a dose that is the highest tolerated for the subject, in the opinion of the investigator, for at least 8 weeks prior to baseline with a stable dose for at least 4 weeks prior to baseline; or MTX dose of 25 mg/week during study, either SQ, intramuscularly, or orally, for at least 8 weeks prior to baseline with a stable dose for at least 4 weeks prior to baseline.

Doses of these therapies are permitted to be decreased during the study; however, all doses are within the combinations and dose ranges specified above. These changes are recorded on the concomitant medication eCRF.

For subjects on corticosteroids at the time of study enrollment, weaning during the study is done according to the following rules: corticosteroid dose of >20 mg and a maximum taper rate per week of 10 mg; 10 to <20 mg and a maximum taper rate per week of 5 mg; or <10 mg and a maximum taper rate per week of 2.5 mg. If a deviation from the permitted concomitant therapy combinations, dose ranges or weaning schedule are necessary, the subject is withdrawn from study participation.

Prohibited Therapies

Concomitant use of biologic treatments during the study is prohibited including use of anakinra (KINERET®, Amgen), abatacept (ORENCIA®, Bristol-Myers Squibb), or tocilizumab (ACTEMRA®, Genentech). A wash-out period of up to 12 weeks is required prior to study enrollment (Visit 2) and after confirmation of eligibility from screening procedures performed at Visit 1 for all biologic treatments received within 12 weeks of the Screening Visit. Prior treatment with natalizumab (TYSABRI®, Biogen) excludes subjects from participation.

Vaccination with live or attenuated virus 3 months prior to screening and at any time during the study is prohibited.

Contraceptive Methods

Sexually active study participants agree to the use of effective contraceptive methods during the study and for the defined period after the end of study visit. Approved methods require double barrier according to the following algorithm: condom plus intra-uterine device or condom plus hormonal contraceptive. Should any subject be sterilized, the procedure for sterilization is required to have been completed more than 3 months prior to study screening visit.

A sexually active male participant is required to use one of the above-described double barrier contraceptive methods during the study and for 3 months after the end-of-study visit. A sexually active female participant is required use one of the above-described double barrier contraceptive methods during the study and for 1 month after the end-of-study visit.

Male subjects also agree not to donate sperm for the duration of the study and for up to 3 months after the end-of-study visit.

Study participants who are abstinent at the time of study entry agree to use the approved methods described in this section should they become sexually active during the study.

Treatment Compliance

Treatment with the anti-LIGHT monoclonal antibody is administered by study center personnel under direct medical supervision, and an appropriate record is made in the source data by the investigator or his/her delegate. The investigator or designee records the dosing information on the appropriate eCRF page. It is the investigator's responsibility to ensure that an accurate record of the administration of the investigational product is maintained.

Randomization and Blinding

All subjects receive the anti-LIGHT monoclonal antibody in an open-label manner.

Treatment after End of Study

After successful enrollment and subsequent completion of or early termination from the study, each subject is treated according to standard clinical practice. In order to support the subject's transition from the clinical study, after care medical expenses such as co-pays and out of pocket medical/treatment associated costs are covered in the total amount of $5,000.00 which may be used up to a total 6 months post-study exit. Aftercare payments are administered by a third-party vendor contracted by the Sponsor.

Example 6.4—Investigational Product Materials and Management

Investigational Product

The anti-LIGHT monoclonal antibody is the investigational product used in this study. It is administered in the dosage form 150 mg/mL solution. The unit dose is 1.0 mg/kg or 3.0 mg/kg. The route of administration is SQ injection in the abdomen in a zone of 4 to 10 cm from the umbilicus with the injection site rotated with each subsequent dose. It is in a colorless to slightly yellowish brown solution. It is manufactured by sanofi-aventis group.

Packaging

All packaging and labeling operations are performed by the sponsor or designee according to Good Manufacturing Practice and Good Clinical Practice (GCP) rules. The investigational product is sent to the study site by the sponsor or designee. Labeling is in the local language and dependent upon local regulations.

Labeling

The vial and the carton have affixed a label that meet the applicable regulatory requirements.

The investigator saves all unused or partially used medication vials and all empty packaging for final disposition locally (sites in Colombia and Israel) or by the sponsor (US sites). Syringes used for dosing are treated as biologic waste and disposed of properly.

Storage

All investigational product is stored between 2° and 8° C. and protected from light. Investigators or other authorized persons (e.g., pharmacists) are responsible for storing the investigational product provided by the sponsor in a secure and safe place in accordance with local regulations, labeling specifications, institutional policies and procedures.

Control of storage conditions for the investigational product provided by the sponsor, especially control of temperature (e.g., refrigerated storage) and daily temperature monitoring, and information on in-use stability and instructions for handling the investigational product are managed according to the rules provided by the sponsor.

Administration

The anti-LIGHT monoclonal antibody is administered by SQ injection in the abdomen in a zone of 4 to 10 cm from the umbilicus with the injection site rotated with each subsequent dose.

Accountability

The investigator maintains adequate records showing the receipt, administration, or other disposition of the investigational product including the date, lot identifier, dosage, volume administered to each subject, and identification of subjects (subject number and initials) who receive the investigational product. The investigator is not permitted to supply the investigational product to any other location or person except those named as sub-investigators on the Form FDA 1572, designated study personnel, and subjects in this study. The investigator is not permitted to dispense the investigational product from any study sites other than those listed on Form FDA 1572. If any of the investigational product is not dispensed; is lost, stolen, spilled, unusable; or was received in a damaged container, this information is documented and reported to sponsor and appropriate regulatory agencies, as required.

Upon completion of the study, unused investigational product is left in the original packaging for final disposition locally (sites in Colombia and Israel) or by the sponsor (US sites). Any partially used investigational product and all empty packaging (e.g., vials) is saved for final disposition locally (sites in Colombia and Israel) or by the sponsor (US sites) and returned to the sponsor's designee for destruction.

Handling and Disposal

Investigational product reconciliation is performed at the site by the investigator and the monitoring team using treatment log forms and documented on the site's investigational product inventory countersigned by the investigator and the monitoring team.

After reconciliation authorization by the sponsor, all used, partially used, and unused vials and all original packaging is disposed of locally (sites in Colombia and Israel) or by the sponsor (US sites). This process is provided to the site by the sponsor's designee.

Example 6.5—Study Procedures and Assessments

Subjects provide written informed consent before any study-related procedures are initiated, including the cessation of prohibited concomitant therapy.

For the timing of assessments and procedures throughout the study, refer to the Schedule of Assessments (see Table 13). Throughout the study, every reasonable effort is made by study personnel to follow the timing of assessments and procedures in the schedule of events for each subject. Visits performed after the Visit 2 baseline visit are scheduled relative to Visit 2 in order to maintain 56 days of open-label treatment and administration every 14 days±3 days). If a subject misses a study visit for any reason, the visit is rescheduled as soon as possible. Each study visit window after Visit 2 is ±3 days. Visit procedures are performed in the order shown however adjustments are allowed to be made to the order to accommodate site-specific requirements.

Study Periods and Visits: Screening (Visit 1, Week-14 to Day 0)

The subject is screened within 14 weeks before enrollment in the study. The following procedures are performed at screening:
1. Obtain written informed consent
2. Review inclusion/exclusion criteria
3. Conduct genotyping for DcR3 genes
4. Collect demographic information
5. Record medical and medication history
6. Perform a complete physical examination, including measurements of weight
7. Collect vital signs, including systolic and diastolic blood pressures, pulse, respiration rate and temperature
8. Perform 12-lead ECG
9. Collect blood samples for clinical laboratory tests
10. Perform QuantiFERON-TB Gold (QFT) blood test, or PPD tuberculosis skin test. If the subject's PPD tine skin test is >5 mm, a confirmatory chest x-ray is required.
11. Collect blood sample for β-hCG test (for females of childbearing potential only)
12. Collect stool sample for *C. difficile* and fecal calprotectin analyses
13. Collect urine sample for urinalysis
14. Collect urine sample for drug testing as warranted
15. Administer the CDAI
16. Administer the IBD-Q questionnaire
17. Conduct the endoscopy with biopsy
18. Assess and record any AEs and concomitant medications
19. Provide access to patient diary (electronic or hard copy) to record daily assessment of abdominal pain, general well-being and number of stools including loose or watery stool (e.g., 6 or 7 on Bristol stool form scale) and daily abdominal pain severity (scale of 0 to 10).

Note that stool samples are allowed to be obtained at any time during the visit. Subjects who fail to meet clinical laboratory entry requirements are allowed to be re-tested once as part of the screening period. Extensions of the screening window to accommodate clinical laboratories re-testing timeframes (excluding endoscopy with biopsy) are permitted but the total screening time, including endoscopy and wash-out, is not to exceed 16 weeks.

Study Periods and Visits: Eligibility Check/Wash-Out Period (Week-12 to Day 0)

Each subject receives a telephone call no later than Week −12 (ie, 12 weeks before the scheduled day of treatment initiation). This call confirms continued subject eligibility. For subjects not requiring a wash-out period after review and confirmation of suitability during this call, the subject is instructed to begin recording their daily abdominal pain rating, general well-being assessment and stool frequency including loose, watery stool frequency in their diary for a minimum of 7 days immediately prior to Visit 2. Once completed the subject returns >7 days from the initial phone call for Visit 2. Any changes in concomitant medication use and any newly occurring AEs since the last evaluation are recorded.

For subjects requiring a wash-out, if eligible the subject is asked to initiate wash-out of any current biologic treatment, as necessary. With the exception of subjects requiring wash-out of the biologic certolizumab pegol (Cimzia), a blood test is administered to subjects undergoing wash-out 8 weeks after their last dose of biologic treatment to ensure that serum levels of any previous biologic treatments are below the level of detection. If it is confirmed that the levels of previous biologic treatment are undetectable, then the subject is instructed to begin recording their daily abdominal pain rating, general well-being assessment and stool frequency including loose, watery stool frequency in their diary for a minimum of 7 days immediately prior to dosing. Once complete the subject returns >7 days from the washout phone call for their Visit 2. If the test results indicate that the previous biologic treatment was detectable, the subject is required to complete a full 12-week wash-out period. For subjects receiving the biologic certolizumab pegol (Cimzia) a 12-week wash-out is required. Upon completion of the washout period, the subject begins completing the diary and has Visit 2 scheduled >7 days from the end of the washout. The diary is completed up to the time of the visit. Any changes in concomitant medication use and any newly occurring AEs since the last evaluation are recorded.

If the subject is not eligible, the subject may have any changes in concomitant medication use and any newly occurring AEs since the last evaluation recorded and may be removed from screening.

Study Periods and Visits: Open-Label Treatment Period, Baseline Visit (Visit 2, Day 0)

Prior to administration of the first dose of investigational product on Day 0, the following procedures are performed:
1. Review inclusion/exclusion criteria to confirm continued eligibility or screen failure status.
   If the subject is still eligible for the study, the subsequent procedures are performed. If the subject is not eligible, any changes in concomitant medication use and any newly occurring AEs since the last evaluation are recorded and the subject is removed from screening.
2. Perform a complete physical examination, including measurements of height and weight
3. Collect vital signs, including systolic and diastolic blood pressures, pulse, respiration rate and temperature
4. Collect blood sample for clinical laboratory tests
5. Collect blood sample for plasma the anti-LIGHT monoclonal antibody concentration and PK analysis
6. Collect blood sample for plasma ADA analysis
7. Collect blood sample for exploratory analyses as defined in Table 13
8. Collect urine sample for urinalysis
9. Collect urine sample for urine β-hCG test (for females of childbearing potential only)
10. Administer the CDAI and IBD-Q
11. Review diary completion
12. Assess and record concomitant medications and newly occurring AEs since the last evaluation In addition, ongoing AEs from the previous visit are assessed and any change in their status is recorded.

After completing the assessments, subjects receive the anti-LIGHT monoclonal antibody by SQ injection in the abdomen in a zone of 4 to 10 cm from the umbilicus with the injection site rotated with each subsequent dose. Vital sign assessments are conducted within 60 minutes post-dosing.

Subjects remain in the clinic for 60 minutes after the investigational product has been administered. During this time, the following details are recorded:
1. Any AEs occurring after dosing
2. Any concomitant medications administered after dosing
3. Assess subject response and available results against individual stopping rules criteria.

After completion of the post-dosing assessments, the subject is permitted to leave the clinic.

Study Periods and Visits: Open-Label Treatment Period, Visit 3 (Day 7 [±3 days])

Subjects return to the clinic on Day 7 (±3 days), at which time the following procedures are performed:
1. Collect blood samples for plasma anti-LIGHT monoclonal antibody concentration and PK analyses
2. Assess and record any AEs and concomitant medications
3. Review diary completion
4. Assess subject response and available results against individual stopping rules criteria. In addition, any ongoing AEs from the previous visit are assessed and any change in their status was to be recorded.

Study Periods and Visits: Visit 4 (Day 14 [±3 days])

Subjects return to the clinic on Day 14 (±3 days), at which time the following procedures are performed prior to dosing:
1. Perform a brief physical examination, including measurement of weight
2. Collect vital signs, including systolic and diastolic blood pressures, pulse, respiration rate and temperature
3. Collect blood sample for clinical laboratory tests
4. Collect blood samples for plasma anti-LIGHT monoclonal antibody concentration, PK and ADA analyses
5. Administer the CDAI
6. Review diary completion
7. Assess and record concomitant medication use and any newly occurring AEs since the last evaluation In addition, ongoing AEs from the previous visit are assessed and any change in their status is recorded.

After completing these assessments, subjects receive the anti-LIGHT monoclonal antibody by SQ injection in the abdomen in a zone of 4 to 10 cm from the umbilicus with the injection site rotated with each subsequent dose. Vital sign assessments are conducted within 60 minutes post-dosing.

Subjects remain in the clinic for 60 minutes after the investigational product has been administered. During this time, the following details are recorded:
1. Any AEs occurring after dosing
2. Any concomitant medications administered after dosing.

After completion of the post-dosing assessments, the subject is permitted to leave the clinic.

Study Periods and Visits: Visit 5 (Day 21 [±3 days])

Subjects return to the clinic on Day 21 (±3 days), at which time the following procedures are performed:
1. Collect blood sample for plasma anti-LIGHT monoclonal antibody concentration and PK analysis
2. Assess and record any AEs and concomitant medications
3. Review diary completion
4. Assess subject response and available results against individual stopping rules criteria.

In addition, any ongoing AEs from the previous visit are assessed and any change in their status is recorded.

Study Periods and Visits: Visit 6 (Day 28 [±3 Days])

Subjects return to the clinic on Day 28 (±3 days), at which time the following procedures are performed prior to dosing:
1. Perform a complete physical examination, including vital sign assessment and measurement weight
2. Collect vital signs, including systolic and diastolic blood pressures, pulse, respiration rate and temperature
3. Perform 12-lead ECG
4. Collect blood sample for clinical laboratory tests
5. Collect blood samples for plasma anti-LIGHT monoclonal antibody concentration, PK and ADA analyses
6. Collect blood sample for exploratory analyses as defined in Table 13
7. Collect stool for fecal calprotectin analysis
8. Collect urine sample for urinalysis
9. Collect urine sample for urine β-hCG test (for females of childbearing potential only)
10. Administer the CDAI
11. Review diary completion
12. Assess and record concomitant medication use and any newly occurring AEs since the last evaluation In addition, any ongoing AEs from the previous visit are assessed and any change in their status is recorded.

After completing these assessments, subjects receive the anti-LIGHT monoclonal antibody by SQ injection in the abdomen in a zone of 4 to 10 cm from the umbilicus with the injection site rotated with each subsequent dose. Vital sign assessments are conducted within 60 minutes post-dosing.

Subjects remain in the clinic for 60 minutes after the investigational product has been administered. During this time, the following details are recorded:
1. Any AEs occurring after dosing
2. Any concomitant medications administered after dosing. NOTE: Stool samples may be obtained at any time during the visit
3. Assess subject response and available results against individual stopping rules criteria.

After completion of the post-dosing assessments, the subject is permitted to leave the clinic.

Study Periods and Visits: Visit 7 (Day 35 [±3 Days])

Subjects return to the clinic on Day 35 (±3 days), at which time the following procedures are performed:
1. Collect blood sample for pharmacokinetic analysis
2. Assess and record any AEs and concomitant medications
3. Review diary completion
4. Assess subject response and available results against individual stopping rules criteria.

In addition, any ongoing AEs from the previous visit are assessed and any change in their status is recorded.

Study Periods and Visits: Visit 8 (Day 42 [±3 days])

Subjects return to the clinic on Day 42 (±3 days), at which time the following procedures are performed prior to dosing:
1. Perform a brief physical examination, including measurement weight
2. Collect vital signs, including systolic and diastolic blood pressures, pulse, respiration rate and temperature
3. Collect blood sample for clinical laboratory tests
4. Collect blood sample for plasma anti-LIGHT monoclonal antibody concentration and PK analysis
5. Administer the CDAI
6. Review diary completion
7. Assess and record any AEs and concomitant medications In addition, any ongoing AEs from the previous visit are assessed and any change in their status is recorded.

After completing these assessments, subjects receive the anti-LIGHT monoclonal antibody by SQ injection in the abdomen in a zone of 4 to 10 cm from the umbilicus with the injection site rotated with each subsequent dose. Vital sign assessments are conducted within 60 minutes post-dosing.

Subjects remain in the clinic for 60 minutes after the investigational product is administered. During this time, the following details are recorded:
1. Any AEs occurring after dosing
2. Any concomitant medications administered after dosing.
3. Assess subject response and available results against individual stopping rules criteria.

After completion of the post-dosing assessments, the subject is permitted to leave the clinic.

Study Periods and Visits: Visit 9 (Day 42 [±3 days])

Subjects return to the clinic on Day 49 (±3 days), at which time the following procedures are performed:
1. Collect blood sample for plasma anti-LIGHT monoclonal antibody concentration and PK analysis
2. Assess and record any AEs and concomitant medications
3. Review diary completion In addition, any ongoing AEs from the previous visit are assessed and any change in their status is recorded Study Periods and Visits: Visit 10 (Day 56 [±3 days])

Subjects return to the clinic on Day 56 (±3 days), at which time the following procedures are performed:
1. Perform a complete physical examination, including measurement of weight
2. Collect vital signs, including systolic and diastolic blood pressures, pulse, respiration rate and temperature
3. Perform 12-lead ECG
4. Collect blood sample for clinical laboratory tests
5. Collect blood samples for plasma anti-LIGHT monoclonal antibody concentration, PK and ADA analysis
6. Collect blood sample for exploratory analyses as defined in Table 13
7. Collect stool for fecal calprotectin analysis
8. Collect urine sample for urinalysis
9. Collect urine sample for urine β-hCG test (for females of childbearing potential only)
10. Administer the CDAI
11. Review diary completion
12. Administer IBD-Q questionnaire
13. Conduct the endoscopy and biopsy 14. Assess and record any AEs and concomitant medications
15. Assess subject response and available results against individual stopping rules criteria.

In addition, any ongoing AEs from the previous visit are assessed and any change in their status is recorded.

Note that stool samples are allowed to be obtained at any time during the visit.

Early Termination

If a subject is withdrawn from the study for any reason, every effort is made to conduct all Day 56 (Visit 10) procedures and assessments.

Study Periods and Visits: Safety Follow-Up, Visit 11 (Day 84 [±3 Days])

Subjects return to clinic 28 days (±3 days) after Visit 10 or the early termination visit for a safety follow-up visit, as appropriate. Subjects have blood collected for plasma anti-LIGHT monoclonal antibody concentration, PK and ADA analyses. Any concomitant medications and newly occurring AEs since the last visit are recorded. In addition, ongoing AEs from the previous visit are assessed and any change in their status is recorded.

Study Duration

The overall study duration is approximately 26 weeks (including up to 14 weeks of screening [inclusive of wash-out of up to 12 weeks, if required], 56 days of open-label treatment, and a follow-up visit approximately 28 days after the final dose of investigational product).

The planned sequence and maximum duration of the study periods is as follows:
1. Screening period: approximately 14 weeks
2. Wash-out period, if applicable: Up to 12 weeks from the subject's last dose of biological treatment
3. Open-label treatment period: 56 days (beginning on Day 0 with doses administered q14 days)
4. Follow-up: 28 days after the last dose of investigational product. The maximum study duration for each subject is approximately 26 weeks.

The maximum treatment duration for each subject is approximately 56 days, with SQ injections beginning on Day 0 and continuing every 14 (±3) days through Day 42.

Note: Extensions of the screening window to accommodate clinical laboratory re-testing timeframes (excluding endoscopy with biopsy) are permitted but are not allowed to exceed a total screening time of 16 weeks.

Safety Assessments

Safety assessments include monitoring of AEs, clinical laboratory tests, vital signs measurements, physical examinations (including measurement of weight) and 12-lead ECG parameters. Demographic information and medical and medication histories are obtained at the screening visit.

All safety assessments are recorded on the appropriate eCRF.

Demographic/Medical History

Demographic information, a complete medical history (which includes surgical history), and medication history is collected at the screening visit by appropriate site staff as delegated by the PI and reviewed and verified by a qualified licensed physician, physician's assistant, or a nurse practitioner. The medical history is reviewed and recorded, including:
Date of birth
Sex
Race and ethnicity
Recent use of medication (30 days prior to enrollment for non-Crohn's associated indications and lifetime recall for all Crohn's associated medications)
CD past and ongoing treatments (recall past year)
CD-related surgical procedures and hospitalizations
History of respiratory, cardiovascular, renal, gastrointestinal, hepatic, endocrine, hematological, neurological, psychiatric, and other diseases; history of surgical procedures Vital Signs Vital signs, including systolic and diastolic blood pressure, pulse, and respiration rate, are collected as shown in the Schedule of Assessments (see Table 13). Vital signs are within the ranges listed below during Screening (Visit 1) and prior to enrollment at Visit 2:
Blood Pressure: 80/50 to 140/90 mm/Hg
Respiratory Rate: 8-20 breaths per minute
Pulse: 50-120 beats per minute
Temperature: 97.8° F. to 99.1° F. (36.5° C. to 37.3° C.)/average 98.6° F. (37° C.)

Vital signs are taken pre- and post-dose at Visits 2, 4, 6 and 8. Pre-dose vital signs are taken within 60 minutes before dosing. Post-dose vital signs are taken at least 60 minutes after dosing, prior to discharge. Additional blood pressure and pulse measurements are optionally performed, as determined by the investigator, in order to ensure appropriate monitoring of subject safety and accurate recording of vital sign measurements. Any changes from baseline deemed clinically significant by the investigator are recorded as AEs.

The same method of blood pressure measurement (auscultatory or oscillometric) is used and documented throughout the study for all subjects. In addition, the conditions of vital signs measurements are controlled and as consistent as possible in order to minimize variability of the readings. Measurements may be collected at a comfortable room temperature with little to no background noise, using the same (appropriately sized) cuff placed at the same location on the same arm. The cuff has had a bladder length that is 80% and a width that is at least 40% of arm circumference (a length-to-width ratio of 2:1).

The subject is asked to remove all clothing that covers the location of cuff placement. The subject may not have exercised or consumed caffeine, alcohol, or nicotine within 30 minutes of collection. The subject may be comfortably seated, with the legs uncrossed, with feet flat on the floor, and the back and arm supported, such that the middle of the cuff on the upper arm is at the level of the right atrium (the mid-point of the sternum). The subject is instructed to relax as much as possible for at least 5 minutes prior to collection. The subject may remain quiet during this time and throughout the measurement.

The bladder is deflated (calibrated for oscillometric method or manually by auscultatory method) at a rate of 2-3 mmHg/sec (and the first and last audible sounds recorded as systolic and diastolic pressures) after at least 5 minutes of rest.

The use of automated devices for measuring pulse is deemed acceptable, although, when done manually, pulse may be measured in the brachial/radial artery for at least 30 seconds. When the timing of these measurements coincides with a blood collection, blood pressure and pulse may be obtained prior to the nominal time of the blood collection.

Physical Examination

A complete physical examination, including measurements of weight, is conducted by a qualified licensed physician, physician's assistant, or a nurse practitioner at the screening visit and at Visits 2 (Day 0), 6 (Day 28) and 10

(Day 56). Brief physical examinations, including measurements of weight, are conducted at Visits 4 (Day 14), and 8 (Day 42) (see Table 13).

The complete physical examination includes a review of the following body systems:
General appearance
Skin
Head, eyes, ears, nose, and throat
Spine/neck/thyroid
Musculoskeletal
Respiratory
Cardiovascular
Neurological
Abdomen (including liver and kidneys)

Any abnormalities or changes in intensity from baseline noted during the review of body systems may be documented in the medical record and reported on the appropriate eCRF. If a new clinically significant abnormal finding is reported after the baseline examination, it is required to be captured as an AE and documented on the appropriate AE eCRF. In addition, resolution of any abnormal findings during the study are noted in the medical record and eCRF if clinically significant.

The brief physical examination is to include a review of general appearance, skin, head, eyes, ears, nose, and throat, abdomen, joints and perianal area at a minimum, with other systems reviewed as medically needed. Measurement of weight is also collected.

Subjects remove their shoes before measurements of weight (in kg) are taken.

Electrocardiogram

A standard 12-lead ECG is conducted by appropriate site staff as delegated by the PI and the results are reviewed and verified by the PI or a qualified licensed physician delegated by the PI as shown in the Schedule of Assessments (see Table 13).

The 12-lead ECG is performed after the subject has been supine for approximately 5 minutes. All ECG recordings are identified with the subject number, subject initials, date, and time of the recording and are included in the subject's study file.

The subject is asked to remove all clothing that covers the location of lead placement. The subject may not have exercised or consumed caffeine, alcohol, or nicotine within 30 minutes prior to collection.

In some cases, it may be appropriate to repeat abnormal ECGs to rule out improper lead placement as contributing to the ECG abnormality. Leads are placed in the same positions each time in order to achieve precise ECG recordings. One complete recording, including a 10-second rhythm strip, may be taken at each time point. It may be immediately assessed as a valid recording and if not valid, it may be repeated. All ECGs collected are entered in the eCRF.

All ECGs are performed using the equipment supplied by the site. ECG recordings are collected and a copy provided to the study sponsor.

The following parameters are recorded on the appropriate eCRF: heart rate, PR, respiration rate (RR), QRS, and QT interval; corrected QT intervals using both the Bazett (QTcB) and Fridericia (QTcF) formulas are also recorded. The investigator's assessment of the ECG tracing as normal or abnormal is required to be documented, and if abnormal, his/her determination of whether the abnormality is clinically significant is documented on the tracing and recorded in the eCRF.

All ECG values that, in the investigator's opinion, show clinically relevant or pathological changes during or after termination of the investigational product are discussed with the medical monitor and reported as AEs and followed.

Clinical Laboratory Tests

Samples for the following clinical laboratory tests are collected at the time points specified in the Schedule of Assessments (see Table 13).

TABLE 14

Clinical Laboratory Tests

| Test type | Description |
| --- | --- |
| Hematology | Hemoglobin, hematocrit, red blood cell count, red blood cell indices, mean corpuscular hemoglobin, mean corpuscular hemoglobin concentration, mean corpuscular volume, platelet count (or estimate), and white blood cell count including differential |
| Serum chemistry | Albumin, total bilirubin, total protein, calcium, alkaline phosphatase, alanine aminotransferase, aspartate aminotransferase, gamma-glutamyl transferase, blood urea nitrogen, creatinine, creatine kinase, glucose, sodium, potassium, chloride, bicarbonate, lactate dehydrogenase, uric acid, eGFR, and C-reactive protein |
| Other | ADAs; LIGHT, cytokines (e.g. IL-1 beta, IL-6, IL-8, and TNF-alpha, and other exploratory cytokines), flow cytometry analysis of peripheral blood leukocytes and RNA sequencing |
| Fecal chemistry | Fecal calprotectin, C. difficile |
| Urinalysis | pH, specific gravity, hemoglobin, white blood cells, red blood cells, glucose, casts, protein, ketones, epithelial cells, crystals, mucous threads, bacteria, yeast, color, and appearance |
| Serum & Urine β-hCG test | For women of childbearing potential only |
| Urine drug screen (screening visit only as warranted) | Amphetamines, barbiturates, benzodiazepines, cocaine, opiates, phencyclidine, cannabinoids, propoxyphene and methadone |
| Testing for previous biologics (for subjects requiring washout) | Commercial test to detect the serum concentrations of four of the common biologic drugs and biosimilars (infliximab [Remicade], infliximad-adba [Renflexis], infliximab-dyyb [Inflectra], adalimumab [Humira], adalimumab-adbm [Cyltezo], adalimumab-atto [Amjevita] vedolizumab [Entyvio] and ustekinumab [Stelara]). Note: Testing not required for certolizumab pego1 (Cimzia) as there is no commercially available test to determine serum concentration. |

Sampled Blood Volume

The sampled blood volume that is taken from each subject is shown in Table 15.

TABLE 15

Blood Samples Taken from Each Subject

| Assessment | | Sample Volume (mL) | Number of Samples | Total Volume (mL) |
| --- | --- | --- | --- | --- |
| Safety | Hematology | 2.0 | 6 | 12.0 |
| | Clinical chemistry | 3.5 | 6 | 21.0 |
| Anti-LIGHT monoclonal antibody concentration and PK analysis(Pre-dose Day 0) | | 2.0 | 2 | 4.0 |

TABLE 15-continued

Blood Samples Taken from Each Subject

| Assessment | Sample Volume (mL) | Number of Samples | Total Volume (mL) |
|---|---|---|---|
| Anti-LIGHT monoclonal antibody concentration and PK analysis | 2.0 | 9 | 18.0 |
| Anti-drug Antibodies (ADA) | 2.0 | 5 | 10.0 |
| Flow Cytometry | 3.0 | 3 | 9.0 |
| RNA sequencing | 2.5 | 3 | 7.5 |
| Cytokines | 3.5 | 3 | 10.5 |
| LIGHT | 2.0 | 3 | 6.0 |
| Testing for previous biologics | 6.0 | 1 | 6.0 |
| Total mL | — | — | 104.0 |

Tuberculosis (TB) Testing

All subjects are screened for tuberculosis using QuantiFERON-TB Gold (QFT) blood test, or tuberculin skin reaction test (PPD skin test) at screening. If the subject's PPD tine skin test is ≥5 mm, a chest x-ray is performed to rule out active or latent pulmonary TB infection. Subjects are excluded from the study if they have active or latent TB as demonstrated by any of the following:

A positive QFT test result or a positive PPD skin test reaction >10 mm.

Chest x-ray in which active or latent pulmonary TB cannot be ruled out.

Genotyping for Decoy Receptor 3

Two milliliters of saliva for genotyping are collected in a designated collection vehicle according to the manufacturer's instructions.

Deoxyribonucleic acid (DNA) is isolated from the saliva samples from each study subject and then evaluated for genetic alteration in TNFRSF6B encoding for the protein DcR3 or alterations in at least one DcR3 network gene. All genotyping is performed in a CLIA certified laboratory specified in the laboratory manual(s) and guidance(s). Any remaining DNA samples are stored for future biomarker studies.

LIGHT, Cytokines, RNA Sequencing and Flow Cytometry Exploratory Analyses

Blood samples are collected for exploratory analyses. Exploratory analyses include but are not limited to LIGHT biomarker, cytokines (e.g. IL-1 beta, IL-6, IL-8, TNF-alpha, and other exploratory cytokines), ribonucleic acid (RNA) sequencing; flow cytometry of peripheral blood leukocytes at visits specified in Table 13.

Testing for Previous Biologics

An adequate wash-out period is required to avoid the potential for confounding the effects related to dosing with the anti-LIGHT monoclonal antibody following the prior use of other biologics. In order to allow for a shorter wash-out period, commercial tests available to identify the serum concentrations of biologics are utilized. With the exception of Cimzia, a blood test is administered to subjects undergoing wash-out 8 weeks after their last dose of biologic treatment to ensure that serum levels of any previous biologic treatments are below the level of detection. If the serum concentration of biologic treatment is undetectable (i.e., below the level of quantification) according to the respective, CLIA-validated commercial test, then the subject is deemed to have completed the wash-out period and is permitted to proceed to Visit 2. If biologic treatment is detected, then the subject completes a full 12-week wash-out period prior to proceeding to Visit 2. For subjects receiving the biologic certolizumab pegol (Cimzia) a 12-week wash-out is required.

Specimen Handling Requirements

The transmission of infectious agents may occur through contact with contaminated needles, blood or blood products and/or laboratory specimens. Consequently, appropriate blood, body fluid and specimen precautions are employed by all study personnel involved in the collection and handling of specimens in both the clinic and laboratory settings. Refer to current recommendations of the appropriate authorities.

In addition to appropriate handling of subject samples, specific regulations exist regarding the shipment of biologic samples. Procedures and regulations for the packaging and shipping of infectious samples are outlined in the study Laboratory Manual(s). The investigator is responsible for ensuring that all study samples that are to be transported to another location are appropriately packed and shipped according to the applicable regulations.

Evaluation of Laboratory Values

The normal ranges of values for the clinical safety laboratory assessments are provided by the responsible laboratory and submitted to sponsor prior to the beginning of the study. They are regarded as the reference ranges upon which clinical decisions are made.

If a laboratory value is out of the reference range, it is not necessarily clinically relevant, with some exceptions. The investigator is required to evaluate the out-of-range values and record his/her assessment of their clinical relevance in the appropriate eCRF.

All laboratory values which, in the investigator's opinion, show clinically relevant or pathological changes during or after termination of the treatment are discussed with the medical monitor and reported as AEs and followed.

Example 6.6—Adverse Events

Adverse Event Collection

The investigator is responsible for the detection and documentation of events meeting the criteria and definitions of an AE or SAE described below. At each visit, the subject is allowed time to spontaneously report any issues since the last visit or evaluation. At each visit, the investigator monitors, asks about, and/or evaluates any AEs using non-leading questions, such as:

"How are you feeling?"

"Have you experienced any issues since your last visit?"

"Have you taken any new medications since your last visit?"

Any clinically relevant observations made during each visit are also considered AEs.

Definition of Adverse Events, Period of Observation and Recording of Adverse Events An AE is defined as any untoward medical occurrence in a clinical investigation subject administered a administered a pharmaceutical product that does not necessarily have a causal relationship with the product. An AE can therefore be any unfavorable and unintended sign (including a new, clinically important abnormal laboratory finding), symptom, or disease, temporally associated with the product, whether or not related to the product.

All AEs are collected from the time of the informed consent was signed until the final safety follow-up visit. This includes events occurring during the screening phase of the study, regardless of whether investigational product is administered. Where possible, a diagnosis rather than a list of symptoms is recorded. If a diagnosis has not been made, then each symptom is listed individually. All AEs are captured on the appropriate AE eCRF and in source documents. In addition to AEs, unexpected benefits outside the investigational product indication are also captured in the source documents and AE eCRF.

All AEs are followed to closure (ie, the subject's health has returned to his/her baseline status or all variables have returned to normal), regardless of whether the subject is still participating in the study. Closure indicates that an outcome is reached, stabilization is achieved (the investigator does not expect any further improvement or worsening of the event), or the event is otherwise explained. When appropriate, medical tests and examinations are performed so that resolution of an event(s) can be documented.

Severity is a classification of intensity whereas an SAE is an AE that meets serious criteria. The above-referenced CTCAE document may be referred to for full description of CTCAE terms and instrumental and self-care ADLs.

Relationship Categorization

A physician/investigator makes the assessment of relationship to the investigational product for each AE. The investigator decides whether, in his or her medical judgment, there is a reasonable possibility that the event could have been caused by the investigational product. If there is no valid reason for suggesting a relationship, then the AE is classified as "not related." Otherwise, the AE is categorized according to the guidelines below. The causality assessment is documented in the source document and the eCRF (Table 16).

TABLE 16

Assessment of Relationship to Investigational Product

| Relationship | Description |
| --- | --- |
| Not Related | Exposure to Investigational Product (IP) has not occurred. OR The administration of IP and the occurrence of the AE are not reasonably related in time. OR The AE is considered likely to be related to an etiology other than the use of the IP, that is, there are no facts/evidence or arguments to suggest a causal relationship to the IP. |
| Possibly Related | The administration of the IP and the occurrence of the AE are reasonably related in time. AND The AE could not be explained equally well by factors or causes other than exposure to IP. |
| Probably Related | The administration of the IP and the occurrence of the AE are reasonably related in time. AND The AE is more likely explained by exposure to IP than by other factors or causes. |

Severity of Adverse Events

The severity of AEs is recorded during the course of the event, including the start and stop dates for each change in severity. An event that changes in severity is captured as a new event. Worsening of pre-treatment events after initiation of the investigational product are recorded as new AEs. For example, if the subject experiences mild, intermittent headaches prior to dosing with investigational product and the headache intensity increases to moderate after the first dose of investigational product, a new AE of moderate intermittent headaches is recorded in the source documents and eCRF.

The medical assessment of clinical severity of an AE is determined using the definitions outlined in Common Terminology Criteria for Adverse Events (CTCAE), Version 4.0 (Published May 28, 2009 with Version 4.0.3 on Jun. 14, 2010 by the US Department of Health and Human Services, National Institutes of Health, National Cancer Institute). Grade 1 is defined as mild; asymptomatic or mild symptoms; or clinical or diagnostic observations only; or intervention not indicated. Grade 2 is defined as moderate; or minimal, local or non-invasive intervention indicated; or limiting age-appropriate instrumental activities of daily living (ADL). Grade 3 is defined as severe or medically significant but not immediately life-threatening; or hospitalization or prolongation of hospitalization indicated; or disabling; or limiting self-care ADL. Grade 4 is defined as life-threatening consequences; or urgent intervention indicated. Grade 5 is death related to AE.

Outcome at the Time of Last Observation

The outcome of an AE at the time of last observation is classified as: recovered/resolved; recovered/resolved with sequelae; recovering/resolving; not recovered/not resolved; fatal; or unknown.

Reporting of Serious Adverse Events

Initial and follow-up SAE reports may be completed by the investigator and sent to the sponsor and the CRO within 24 hours of the first awareness of a SAE. The investigator completes, signs and dates the appropriate SAE form and verifies the accuracy of the information against corresponding source documents. No source documents are sent with the SAE form. This SAE information (form) is sent to the CRO pharmacovigilance department, with a copy to the sponsor's medical monitor by e-mail or fax.

Definition of Serious Adverse Event

An SAE is any untoward medical occurrence, whether considered to be related to investigational product or not, that at any dose: results in death; is life-threatening; requires inpatient hospitalization or prolongation of existing hospitalization; results in persistent or significant disability/incapacity; is a congenital anomaly; or is an important medical event.

Note that the term "life-threatening" in the definition of "serious" refers to an event in which the subject was at risk of death at the time of the event; it does not refer to an event which hypothetically might have caused death if it were more severe.

Note that inpatient hospitalization is defined as 24 hours in a hospital or an overnight stay. An elective hospital admission to treat a condition present before exposure to the test drug, or a hospital admission for a diagnostic evaluation of an AE, does not qualify the condition or event as an SAE. Further, an overnight stay in the hospital that is only due to transportation, organization, or accommodation problems and without medical background does not need to be considered an SAE.

Note that a congenital anomaly in an infant born to a mother who was exposed to the investigational product during pregnancy is an SAE. However, a newly diagnosed pregnancy in a subject that has received an investigational product is not considered an SAE unless it is suspected that the investigational product interacted with a contraceptive method and led to the pregnancy.

Note that medical and scientific judgment may be exercised in deciding whether it is appropriate to consider other situations serious, such as important medical events that may not be immediately life-threatening or result in death or hospitalization but may jeopardize the subject or may require intervention to prevent one of the other outcomes listed in the definition above. Examples of such events are intensive treatment in an emergency room or at home for allergic bronchospasm, blood dyscrasias or convulsions that do not result in hospitalization, or development of drug dependency or drug abuse.

Serious Adverse Event Collection Time Frames

All SAEs, regardless of the relationship to study, are collected from the time the subject signs the informed consent until the subject's last visit (office or telephone contact). The investigator or designee reports all SAEs promptly to the CRO and sponsor's medical monitor within 24 hours of first becoming aware of the event.

Any SAE(s), regardless of relationship to IP, discovered by the investigator at any interval after the study has completed is reported to the CRO and sponsor's medical monitor within 24 hours of the first awareness of the event.

Serious Adverse Event Onset and Resolution Dates

The onset date of the SAE is defined as the date the event meets serious criteria. The resolution date is the date the event no longer meets serious criteria, the date symptoms resolve or the event is considered chronic. In the case of hospitalization, the hospital admission and discharge dates are considered respectively, the onset and resolution dates of the SAE.

Any signs or symptoms experienced by the subject after signing the informed consent form, or leading up to the onset date of the SAE or following the resolution date of the SAE are recorded as AEs.

Fatal Outcome

An outcome of "fatal" may only be selected when the AE results in death. If more than 1 AE is possibly related to the subject's death, "fatal" outcome is indicated for each such AE.

Any AE that resulted in the subject's death was required have "fatal" checked as an outcome with the date of death recorded as the resolution date. Adverse events resulting in death may be reported within 24 hours as SAEs, if not already reported as such.

For other AEs ongoing at the time of death that did not contribute to the subject's death, the outcome is considered "not resolved" with no resolution date recorded.

Adverse Events of Special Interest and Adverse Drug Reactions

There are no events from research to date which qualify as an adverse event of special interest. Adverse drug reactions observed in the anti-LIGHT monoclonal antibody pre-clinical study include injection site reactions.

Adverse drug reactions with other biologic agents include: potential for increased infection (including opportunistic infections such as tuberculosis); hypersensitivity reactions (including anaphylaxis); immunogenicity; malignancy; impaired immunization; or CD exacerbation.

Pregnancy

All females of childbearing potential who participate in the study are counseled on the need to practice adequate birth control and on the importance of avoiding pregnancy during study participation. Study participants are instructed to contact the investigator or study staff immediately if pregnancy occurs or is suspected.

Pregnancy testing is also conducted prior to administration of investigational product on every female of childbearing potential. Any female who is found to be pregnant at the screening visit is excluded from the study and considered a screening failure.

The investigator reports the pregnancy of any female (study participant or female partner of male study participant) who becomes pregnant during investigational product treatment or within 7 days of discontinuing the investigational product. The pregnancy is reported within 24 hours of awareness to the CRO. The investigator contacts the designated individual(s) who receive SAE notification and record information related to the pregnancy on the designated form provided by the sponsor or its designee.

Early termination visit assessments are conducted as soon as possible after learning of the pregnancy. The investigator is also responsible for following the pregnancy until delivery or termination. These findings are reported on the Exposure in Utero form/other designated form and forwarded to the designated individual(s). The event meets the SAE criterion only if it results in a spontaneous abortion or a congenital anomaly.

Example 6.7—Abuse, Misuse, Overdose, and Medication Error

Abuse, misuse, overdose or medication error involving the investigational product, as defined below, is reported to the sponsor using the SAE reporting procedures whether or not they result in an AE or SAE. The 24-hour reporting period from time of first awareness does not apply to an abuse, misuse, overdose, or medication error event(s) unless the abuse, misuse, overdose, or medication error event results in a SAE.

TABLE 17

Definitions of Abuse, Misuse, Overdose, and Medication Error

| Category | Definition |
|---|---|
| Abuse | Persistent or sporadic intentional intake of IP when used for a non- medical purpose (for example, to get high, for potential psychoactive effects) in a manner that would be detrimental to the individual and/or society |
| Misuse | Intentional use of IP other than as directed or indicated at any dose. This includes where IP is not used as directed at the dose prescribed in the protocol. |
| Overdose | Intentional or unintentional intake of a dose of IP exceeding the dose prescribed to the subject as part of the study. |
| Medication Error | Error made in prescribing, dispensing, administration and/or use of IP. A medication error is reportable to the sponsor or its designee if it involves: Administration and/or use of an unassigned treatment (for example, incorrect IP kit used by subject) Administration and/or use of expired IP. |

IP = investigational product
Note
that an abuse, misuse, overdose or medication error event can meet more than 1 category. Missing doses are not considered medication error events and do not need to be reported.

Example 6.8—Anti-LIGHT Monoclonal Antibody Concentration, Pharmacokinetic and Anti-Drug Antibody Assessments Pharmacokinetics are calculated from the plasma concentrations of the anti-LIGHT monoclonal antibody.
Blood Sample Collection and Analysis Blood samples are collected within 60 minutes prior to the administration of the anti-LIGHT monoclonal antibody on Days 0, 14, 28 and 42 (Visits 2, 4, 6, and 8 respectively) and at any time on Days 7, 21, 35, 49, 56, and 84 (Visits 3, 5, 7, 9, 10, and 11) and processed to plasma. Time of PK samples is recorded in the electronic CRF. A total of 1.0 mL plasma (0.5 mL per PK and ADA sample) is collected from each subject to measure plasma concentrations of the anti-LIGHT monoclonal antibody or ADA samples. Pharmacokinetic and ADA samples are processed according to the methods and directions set forward in the Laboratory Manual(s) and guidance(s).

Pharmacokinetic and ADA plasma sample analysis is performed by a specified laboratory according to their SOPs using a validated enzyme-linked immunosorbent assay (ELISA).

Example 6.9—Assessment of Efficacy

Crohn's Disease Activity Index

The CDAI is completed by a qualified licensed physician, physician's assistant, or a nurse practitioner at the times shown in the Schedule of Assessments (see Table 13). Site personnel conducting the CDAI derive individual and total scores, with standard weights calculated as follows: standard weight for men=(height in m)2×22.1; standard weight for women=(height in m)2×20.8.

Information on abdominal pain and frequency of loose and watery stools is taken from subject diary information. The same individual complies the CDAI for a given subject throughout the study, whenever possible.

The CDAI was developed by the National Cooperative Crohn's Disease Study group and published in 1976 by Best et al. (1976) (Best et al., Development of a Crohn's disease activity index, National Cooperative Crohn's Disease Study, Gastroenterol., 1976:70; 439-44) to determine variables that best predicted disease activity. A total of 8 items were identified (abdominal pain, number of liquid stools, general well-being, extraintestinal complication, use of antidiarrheal drugs, abdominal mass, hematocrit, and body weight). Each item is scored on individual parameter criteria. Total CDAI scores can range from 0 to approximately 600 with higher scores indicating more active disease. The CDAI has been the most frequently used efficacy scale for interventional studies in CD (Sostegni et al., Review: Crohn's disease: monitoring disease activity, Aliment Pharmacolo Ther., 2003:17 (Suppl. 2) 11-17).

Endoscopy with Biology and Histology

All subjects who enroll in the study undergo an endoscopy with biopsy at screening and again at Day 56 (Visit 10) or at early termination. Screening endoscopies are optionally performed either as a stand-alone endoscopy for purposes of this protocol or as a clinically-required endoscopy, provided consenting procedures for this study are completed prior to endoscopy.

Endoscopy evaluation uses the SES-CD. The SES-CD is a simple, easy-to-use endoscopic scoring system developed specifically for CD. It assesses 4 variables: size of ulcers, percentage of ulcerated surface, percentage of affected surface and the presence of narrowing across 4 categories per variable on a scale of 0 to 3 (Daperno M, D'Haens G, Van Assche G et al. Development and validation of a new, simplified endoscopic activity score for Crohn's disease: the SES-CD. Gastroinest Endosc. 2004 October; 60(4):505-12). Biopsies taken at screening are assessed for histological confirmation of disease. Each subject has screening and Visit 10/ET biopsy samples retained for evaluation of exploratory parameters (which may include but is not limited to DcR3, LIGHT, HVEM and LTβR) which could optionally occur after study completion.

Patient-Reported Assessment of Well-being, Abdominal Pain and Stool Frequency

All subjects who enroll in the study report their daily assessment of well-being, abdominal pain and stool frequency including loose and/or watery stools via a diary (electronic or hard copy). Abdominal pain is assessed on a scale of 0 to 3 with higher values indicating greater pain severity. The stool frequency including number of loose and/or watery stools per day, equivalent to a score of a 6 or 7 on the Bristol Stool Scale, is recorded.

Loose stools are described as fluffy pieces with ragged edges, a mushy stool. Watery stools are described as watery, no solid pieces (O'Donnell et al., Detection of pseudodiarrhoea by simple clinical assessment of intestinal transit rate, Br. Med. J. 1990; 300:439-40).

Quality of Life Assessment—Inflammatory Bowel Disease Questionnaire

The IBD-Q is a 32 item questionnaire validated to measure quality of life in Crohn's Disease. The IBD-Q assesses the dimensions of bowel function, emotional status, systemic symptoms and social function (Guyatt et al., A new measure of health status for clinical trials in inflammatory bowel disease, *Gastroenterol.*, 1989:96; 804-10). The IBD-Q is completed by all subjects at screening (Visit 1), before dosing (Visit 2), and at the end of the open-label treatment period or early termination (Visit 10/ET) (see Table 13).

Example 6.10—Statistics

Pharmacokinetic, efficacy and quality of life data is summarized with traditional descriptive statistics. Continuous variables are summarized with N, mean, standard deviation, and range. Categorical variables are summarized by frequencies and percentages.

No formal inferential analyses are planned.

The Safety Population includes all subjects who enroll in the study and receive any amount of investigational product. The Pharmacokinetic Population includes all subjects who receive their assigned dose of the anti-LIGHT monoclonal antibody and for whom the anti-LIGHT monoclonal antibody plasma concentration data is available. The Efficacy Population includes all subjects who have a baseline and at least 1 post-baseline efficacy score.

Analyses of efficacy focus on the Efficacy Population. Results of endpoints (e.g., CDAI, SES-CD, abdominal pain and loose/watery stool frequency, and IBD-Q) are summarized by visit for each cohort, both as raw scores and the change from baseline value. CDAI individual and total scores are derived programmatically using recorded data from patient diary, responses to CDAI questions, laboratory tests, and physical exam results.

Quantitative endoscopy and biopsy results are also summarized for both the Baseline and End of study visits.

Analyses of safety data are focused on the Safety Population.

Safety variables include treatment-emergent AEs (TE-AEs), clinical laboratory results, vital signs measurements, ECG results, and physical examination findings.

Adverse events are coded using Medical Dictionary for Regulatory Affairs (MedDRA) version 20. TEAEs are defined as any AE having first onset or worsening in severity after the first administration of IP. TEAEs are classified by system organ class (SOC) and preferred term and summarized by the number of subjects reporting each event for each cohort and overall. Similar summaries are produced for SAEs, AEs leading to discontinuation, and AEs with at least a possible relationship to the investigational product. The intensity of AEs and the relationship to the investigational product are also summarized for each SOC and preferred term.

For clinical laboratory tests, descriptive summaries of actual (absolute) values and change from baseline values are presented by cohort for each study visit. The number of subjects with clinical laboratory values below, within, or above normal ranges at each study visit are tabulated (shift tables) for each clinical laboratory test by cohort.

Vital signs (systolic and diastolic blood pressure, pulse, and respiratory rate) and ECG results are summarized by visit and cohort using appropriate descriptive statistics. The number and percentage of subjects with abnormal ECG findings is summarized by cohort for each study visit.

Data in this open-label study is monitored continually.

This is the first use of the anti-LIGHT monoclonal antibody in the intended population of patients with CD resistant to anti-TNFα monoclonal antibodies. The sample size of the study was based on feasibility.

Example 7

Presented herein in Example 7 are certain results of the study conducted according to the methods as described in Example 6.

Three timepoint serum samples were obtained from the two patients who have completed anti-LIGHT antibody treatment in the study described in Example 6. Healthy adult donors (n=30 controls) had an average pre-treatment free LIGHT level of 202 μg/mL. The first patient had an elevated plasma pre-treatment free LIGHT level of 455 μg/mL. After treatment with the anti-LIGHT antibody (having a VH of SEQ ID NO. 8, and a VL of SEQ ID NO: 9) subcutaneous (SQ) every (q) 2 weeks, the subject's plasma free LIGHT levels were found to be in the normal range; free-LIGHT levels were 15 and 24 μg/mL on days 28 and 56, respectively. The second patient had an elevated plasma pre-treatment free LIGHT level of 193 μg/mL. After treatment with the anti-LIGHT antibody subcutaneous (SQ) every (q) 2 weeks, the subject's plasma free LIGHT levels were found to be in the normal range; free-LIGHT levels were 42 and 29 μg/mL on days 28 and 56, respectively. These data show that in the outpatient setting even relatively low doses of the anti-LIGHT antibody can decrease plasma free LIGHT levels, and that the free LIGHT levels can stay decreased.

Moreover, the first patient's clinical improvement was seen to correlate with this reduction. Simple Endoscopic Score for Crohn's Disease (SES-CD) the first patient's score decreased with treatment. An SES-CD Score of: 0-2 means remission; 3-6 means mild; 7-15 means moderate; and >15 means severe. The first patient's SES-CD score was 11 at screening and was 4 at day 56.

Example 8

Figure 11:
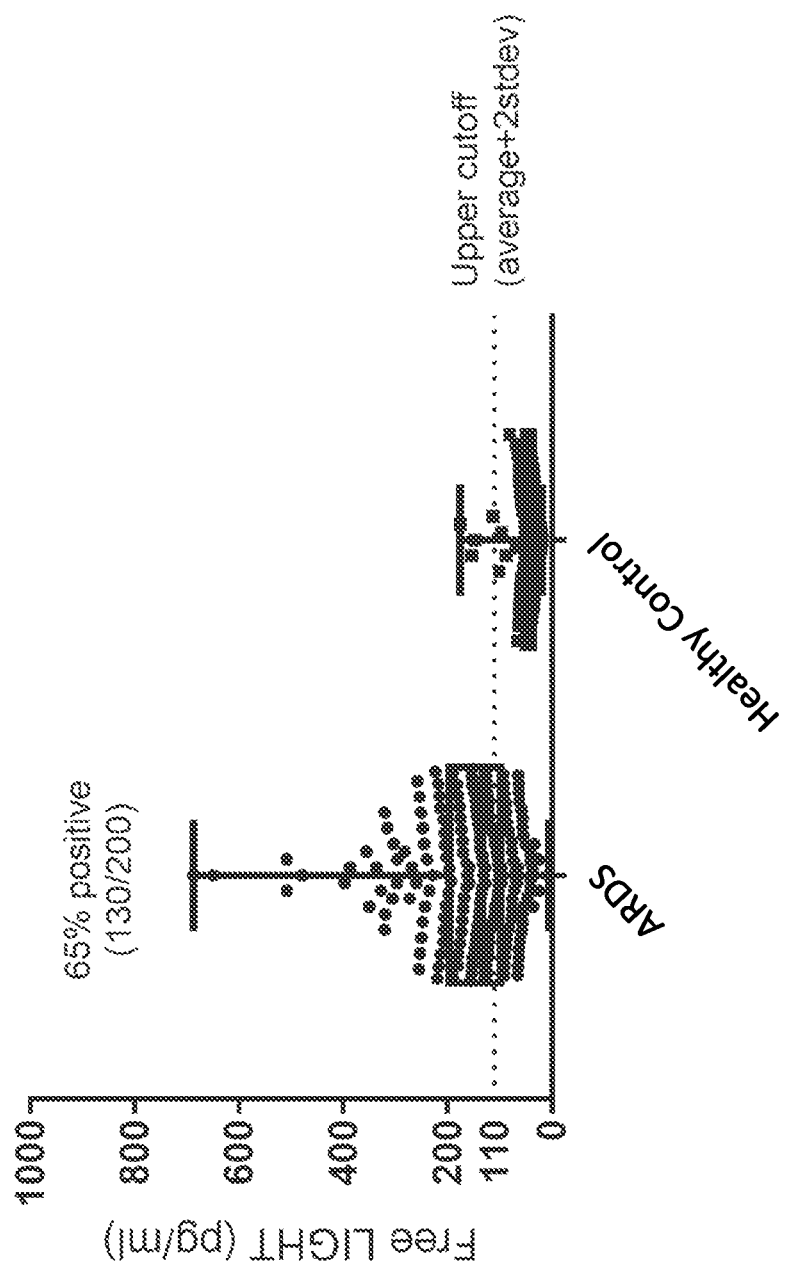
FIG. 11 shows a box plot generated from data from LIGHT testing using the free LIGHT assay described herein performed on samples from ARDS patients and compared to healthy donor LIGHT levels. There are 79 healthy control data points.

LIGHT testing using the free LIGHT assay described herein was performed on samples from ARDS patients and compared to healthy donor LIGHT levels. The preliminary data shows elevated LIGHT levels in the ARDS population compared to healthy donor levels. A box plot generated on this data is shown in FIG. 11.

The following Table 18 provides the sequences referred to in this application.

TABLE 18

Table of Sequences

| SEQ ID NO | DESCRIPTION | SEQUENCE |
|---|---|---|
| 1 | Human DcR3 amino acid sequence | MRALEGPGLS LLCLVLALPA LLPVPAVRGV AETPTYPWRD AETGERLVCA QCPPGTFVQR PCRRDSPTTC GPCPPRHYTQ FWNYLERCRY CNVLCGEREE EARACHATHN RACRCRTGFF AHAGFCLEHA SCPPGAGVIA PGTPSQNTQC QPCPPGTFSA SSSSSEQCQP HRNCTALGLA LNVPGSSSHD TLCTSCTGFP LSTRVPGAEE CERAVIDFVA FQDISIKRLQ RLLQALEAPE GWGPTPRAGR AALQLKLRRR LTELLGAQDG ALLVRLLQAL RVARMPGLER SVRERFLPVH |
| 2 | Heavy Chain (HC) CDR1 antibody F19 | GYNWH |
| 3 | HC CDR2 antibody F19 | EITHSGSTNYNPSLKS |
| 4 | HC CDR3 antibody F19 | EIAVAGTGYYGMDV |
| 5 | LC CDR1 antibody F19 | RASQGINSAFA |
| 6 | LC CDR2 antibody F19 | DASSLES |
| 7 | LC CDR3 antibody F19 | QQFNSYPLT |
| 8 | Heavy chain variable region antibody F19 | QVQLQQWGAG LLKPSETLSL TCAVYGGSFS GYNWHWIRQP PGKGLEWIGE ITHSGSTNYN PSLKSRVTIS VDTSKNQFSL KLSSVTAADT AVYYCVREIA VAGTGYYGMD VWGQGTTVTV SSASTKGPSV FPLAPCSRST SESTAALGCL VKDYFPEPVT VSWNSGALTS GVHTFPAVLQ SSGLYSLSSV VTVPSSSLGT KTYTCNVDHK PSNTKVDKRV ESKYGPPCPP CPAPEFEGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLG |
| 9 | Light chain variable region antibody F19 | AIQLTQSPSS LSASVGDRVT ITCRASQGIN SAFAWYQQKP GKAPKLLIYD ASSLESGVPS RFSGSGSGTD FTLTISSLQP EDFATYYCQQ FNSYPLTFGG GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 10 | Alternative LC CDR1 antibody F19 | RASRGINSAFA |
| 11 | Alternative LC CDR2 antibody F19 | DASSLES |
| 12 | Alternative LC CDR3 antibody F19 | QQFNSYPLT |
| 13 | Alternative LC CDR1 antibody F19 | RVSQGISSYLN |
| 14 | Alternative LC CDR2 antibody F19 | SASNLQS |

TABLE 18-continued

Table of Sequences

| SEQ ID NO | DESCRIPTION | SEQUENCE |
|---|---|---|
| 15 | Alternative LC CDR3 antibody F19 | ARTNAPPT |
| 16 | Alternative LC CDR1 antibody F19 | RMSQGISSYLA |
| 17 | Alternative LC CDR2 antibody F19 | AASTLQS |
| 18 | Alternative LC CDR3 antibody F19 | QQYYSFPYT |
| 19 | Alternative LC CDR1 antibody F19 | RASQGVSSYLA |
| 20 | Alternative LC CDR2 antibody F19 | DASNRAT |
| 21 | Alternative LC CDR3 antibody F19 | QQRSNWHP |
| 22 | HC CDR1 antibody E1 | RFNMN |
| 23 | HC CDR2 antibody E1 | YISSSSYTIYYADSVKG |
| 24 | HC CDR3 antibody E1 | SIAAFDY |
| 25 | LC CDR1 antibody E1 | RASQGISSALA |
| 26 | LC CDR2 antibody E1 | DASSLES |
| 27 | LC CDR3 antibody E1 | QQFNSYRT |
| 28 | Alternative LC CDR1 antibody E1 | RASQSVSSSYLT |
| 29 | Alternative LC CDR2 antibody E1 | GASSRAT |
| 30 | Alternative LC CDR3 antibody E1 | QQYGSSMYT |
| 31 | Alternative LC CDR1 antibody E1 | RASQSVSSSYLA |
| 32 | Alternative LC CDR2 antibody E1 | GASNRAT |
| 33 | Alternative LC CDR3 antibody E1 | QQYGSSPWT |
| 34 | HC CDR1 antibody E13 | NAWMS |
| 35 | HC CDR2 antibody E13 | RIKSKIDGGTTDYAAPVKG |

TABLE 18-continued

Table of Sequences

| SEQ ID NO | DESCRIPTION | SEQUENCE |
|---|---|---|
| 36 | HC CDR3 antibody E13 | AMAGAFGF |
| 37 | LC CDR1 antibody E13 | RASQSVSSSYLA |
| 38 | LC CDR2 antibody E13 | GASSRAT |
| 39 | LC CDR3 antibody E13 | QQYGSSPMYT |
| 40 | HC CDR1 antibody E63 | SGGYYWS |
| 41 | HC CDR2 antibody E63 | YIYYSGSTNYNPSLKS |
| 42 | HC CDR3 antibody E63 | WITMFRGVGFDP |
| 43 | LC CDR1 antibody E63 | RASQSIGSSLH |
| 44 | LC CDR2 antibody E63 | YASQSFS |
| 45 | LC CDR3 antibody E63 | RQSSSLPLT |
| 46 | HC CDR1 antibody F23 | GYYWN |
| 47 | HC CDR2 antibody F23 | EINQYNPSLKS |
| 48 | HC CDR3 antibody F23 | EIAIADKGYYGLDV |
| 49 | LC CDR1 antibody F23 | RASQGISSALA |
| 50 | LC CDR2 antibody F23 | DASSLES |
| 51 | LC CDR3 antibody F23 | QQFNSYPLT |
| 52 | HC CDR1 | SYYIH |
| 53 | HC CDR2 | PGSDITKYNEKFKG |
| 54 | HC CDR3 | GISTYSAMDF |
| 55 | LC CDR1 | KASQDVGTAVA |
| 56 | LC CDR2 | WASTRHT |
| 57 | LC CDR3 | QQYSSYPLT |
| 58 | HC variable region | QVQLVQSGAE VKKPGASVKV SCKASGYTFT SYYIHWVRQA PGQRLEWMGW IFPGSDITKY NEKFKGRVTI TRDTSASTAY MELSSLRSED TAVYYCARED YGISTYSAMD FWGQGTLVTV SS |
| 59 | LC variable region | DIQLTQSPSF LSASVGDRVT ITCKASQDVG TAVAWYQQKP GKAPKLLIYW ASTRHTGVPS RFSGSGSGTE FTLTISSLQP EDFATYYCQQ YSSYPLTFGQ GTKVEIKR |
| 60 | HC CDR1 of 18E04 | HFDIN |
| 61 | HC CDR2 of 18E04 | WMNPDSDNTDYAQEFQG |

TABLE 18-continued

Table of Sequences

| SEQ ID NO | DESCRIPTION | SEQUENCE |
|---|---|---|
| 62 | HC CDR3 of 18E04 | GGTTLDY |
| 63 | LC CDR1 of 18E04 | SGDALPKKYAY |
| 64 | LC CDR2 of 18E04 | EDSKRPS |
| 65 | LC CDR3 of 18E04 | YSTDSSDNHVI |
| 66 | HC CDR1 of 98C07 | DYYMS |
| 67 | HC CDR2 of 98C07 | YISRSSFIYYSESVKG |
| 68 | HC CDR3 of 98C07 | WELSPFDY |
| 69 | LC CDR1 of 98C07 | RASQGISNYLA |
| 70 | LC CDR2 of 98C07 | AASSLQS |
| 71 | LC CDR3 of 98C07 | QQYNTYPFT |
| 72 | HC CDR1 of 1C02 | YYGIS |
| 73 | HC CDR2 of 1C02 | WISANSGNTNYAQKFQG |
| 74 | HC CDR3 of 1C02 | GGVAVLEY |
| 75 | LC CDR1 of 1C02 | WASQGISSYLA |
| 76 | LC CDR2 of 1C02 | VASTLQS |
| 77 | LC CDR3 of 1C02 | QQLKIYPLT |
| 78 | HC CDR1 of 1C06 | DYYMN |
| 79 | HC CDR2 of 1C06 | DISSRDNTIYYADSVKG |
| 80 | HC CDR3 of 1C06 | ARERGFGDYFGMDV |
| 81 | LC CDR1 of 1C06 | RASQDISSALA |
| 82 | LC CDR2 of 1C06 | DASSLES |
| 83 | LC CDR3 of 1C06 | QQFNTYPLT |

SEQUENCE LISTING

```
Sequence total quantity: 83
SEQ ID NO: 1                    moltype = AA   length = 300
FEATURE                         Location/Qualifiers
REGION                          1..300
                                note = misc_feature - Human DcR3 amino acid sequence
source                          1..300
                                mol_type = protein
                                organism = Homo sapiens
SEQUENCE: 1
MRALEGPGLS LLCLVLALPA LLPVPAVRGV AETPTYPWRD AETGERLVCA QCPPGTFVQR   60
PCRRDSPTTC GPCPPRHYTQ FWNYLERCRY CNVLCGEREE EARACHATHN RACRCRTGFF  120
AHAGFCLEHA SCPPGAGVIA PGTPSQNTQC QPCPPGTFSA SSSSSEQCQP HRNCTALGLA  180
LNVPGSSSHD TLCTSCTGFP LSTRVPGAEE CERAVIDFVA FQDISIKRLQ RLLQALEAPE  240
GWGPTPRAGR AALQLKLRRR LTELLGAQDG ALLVRLLQAL RVARMPGLER SVRERFLPVH  300

SEQ ID NO: 2                    moltype = AA   length = 5
FEATURE                         Location/Qualifiers
REGION                          1..5
                                note = Synthetic: Heavy Chain (HC) CDR1 antibody F19
source                          1..5
                                mol_type = protein
                                organism = synthetic construct
SEQUENCE: 2
GYNWH                                                                5

SEQ ID NO: 3                    moltype = AA   length = 16
FEATURE                         Location/Qualifiers
REGION                          1..16
                                note = Synthetic: HC CDR2 antibody F19
source                          1..16
                                mol_type = protein
                                organism = synthetic construct
SEQUENCE: 3
EITHSGSTNY NPSLKS                                                   16

SEQ ID NO: 4                    moltype = AA   length = 14
FEATURE                         Location/Qualifiers
REGION                          1..14
                                note = Synthetic: HC CDR3 antibody F19
source                          1..14
                                mol_type = protein
                                organism = synthetic construct
SEQUENCE: 4
EIAVAGTYY GMDV                                                      14

SEQ ID NO: 5                    moltype = AA   length = 11
FEATURE                         Location/Qualifiers
REGION                          1..11
                                note = Synthetic: LC CDR1 antibody F19
source                          1..11
                                mol_type = protein
                                organism = synthetic construct
SEQUENCE: 5
RASQGINSAF A                                                        11

SEQ ID NO: 6                    moltype = AA   length = 7
FEATURE                         Location/Qualifiers
REGION                          1..7
                                note = Synthetic: LC CDR2 antibody F19
source                          1..7
                                mol_type = protein
                                organism = synthetic construct
SEQUENCE: 6
DASSLES                                                              7

SEQ ID NO: 7                    moltype = AA   length = 9
FEATURE                         Location/Qualifiers
REGION                          1..9
                                note = Synthetic: LC CDR3 antibody F19
source                          1..9
                                mol_type = protein
                                organism = synthetic construct
SEQUENCE: 7
QQFNSYPLT                                                            9

SEQ ID NO: 8                    moltype = AA   length = 448
FEATURE                         Location/Qualifiers
REGION                          1..448
```

```
                            note = Synthetic: Heavy chain variable region antibody F19
source                      1..448
                            mol_type = protein
                            organism = synthetic construct
SEQUENCE: 8
QVQLQQWGAG LLKPSETLSL TCAVYGGSFS GYNWHWIRQP PGKGLEWIGE ITHSGSTNYN   60
PSLKSRVTIS VDTSKNQFSL KLSSVTAADT AVYYCVREIA VAGTGYYGMD VWGQGTTVTV  120
SSASTKGPSV FPLAPCSRST SESTAALGCL VKDYFPEPVT VSWNSGALTS GVHTFPAVLQ  180
SSGLYSLSSV VTVPSSSLGT KTYTCNVDHK PSNTKVDKRV ESKYGPPCPP CPAPEFEGGP  240
SVFLFPPKPK DTLMISRTPE VTCVVVDVSQ EDPEVQFNWY VDGVEVHNAK TKPREEQFNS  300
TYRVVSVLTV LHQDWLNGKE YKCKVSNKGL PSSIEKTISK AKGQPREPQV YTLPPSQEEM  360
TKNQVSLTCL VKGFYPSDIA VEWESNGQPE NNYKTTPPVL DSDGSFFLYS RLTVDKSRWQ  420
EGNVFSCSVM HEALHNHYTQ KSLSLSLG                                    448

SEQ ID NO: 9                moltype = AA   length = 214
FEATURE                     Location/Qualifiers
REGION                      1..214
                            note = Synthetic: Light chain variable region antibody F19
source                      1..214
                            mol_type = protein
                            organism = synthetic construct
SEQUENCE: 9
AIQLTQSPSS LSASVGDRVT ITCRASQGIN SAFAWYQQKP GKAPKLLIYD ASSLESGVPS   60
RFSGSGSGTD FTLTISSLQP EDFATYYCQQ FNSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 10               moltype = AA   length = 11
FEATURE                     Location/Qualifiers
REGION                      1..11
                            note = Synthetic: Alternative LC CDR1 antibody F19
source                      1..11
                            mol_type = protein
                            organism = synthetic construct
SEQUENCE: 10
RASRGINSAF A                                                        11

SEQ ID NO: 11               moltype = AA   length = 7
FEATURE                     Location/Qualifiers
REGION                      1..7
                            note = Synthetic: Alternative LC CDR2 antibody F19
source                      1..7
                            mol_type = protein
                            organism = synthetic construct
SEQUENCE: 11
DASSLES                                                              7

SEQ ID NO: 12               moltype = AA   length = 9
FEATURE                     Location/Qualifiers
REGION                      1..9
                            note = Synthetic: Alternative LC CDR3 antibody F19
source                      1..9
                            mol_type = protein
                            organism = synthetic construct
SEQUENCE: 12
QQFNSYPLT                                                            9

SEQ ID NO: 13               moltype = AA   length = 11
FEATURE                     Location/Qualifiers
REGION                      1..11
                            note = Synthetic: Alternative LC CDR1 antibody F19
source                      1..11
                            mol_type = protein
                            organism = synthetic construct
SEQUENCE: 13
RVSQGISSYL N                                                        11

SEQ ID NO: 14               moltype = AA   length = 7
FEATURE                     Location/Qualifiers
REGION                      1..7
                            note = Synthetic: Alternative LC CDR2 antibody F19
source                      1..7
                            mol_type = protein
                            organism = synthetic construct
SEQUENCE: 14
SASNLQS                                                              7

SEQ ID NO: 15               moltype = AA   length = 8
FEATURE                     Location/Qualifiers
```

```
REGION                  1..8
                        note = Synthetic: Alternative LC CDR3 antibody F19
source                  1..8
                        mol_type = protein
                        organism = synthetic construct
SEQUENCE: 15
ARTNAPPT                                                                       8

SEQ ID NO: 16           moltype = AA   length = 11
FEATURE                 Location/Qualifiers
REGION                  1..11
                        note = Synthetic: Alternative LC CDR1 antibody F19
source                  1..11
                        mol_type = protein
                        organism = synthetic construct
SEQUENCE: 16
RMSQGISSYL A                                                                  11

SEQ ID NO: 17           moltype = AA   length = 7
FEATURE                 Location/Qualifiers
REGION                  1..7
                        note = Synthetic: Alternative LC CDR2 antibody F19
source                  1..7
                        mol_type = protein
                        organism = synthetic construct
SEQUENCE: 17
AASTLQS                                                                        7

SEQ ID NO: 18           moltype = AA   length = 9
FEATURE                 Location/Qualifiers
REGION                  1..9
                        note = Synthetic: Alternative LC CDR3 antibody F19
source                  1..9
                        mol_type = protein
                        organism = synthetic construct
SEQUENCE: 18
QQYYSFPYT                                                                      9

SEQ ID NO: 19           moltype = AA   length = 11
FEATURE                 Location/Qualifiers
REGION                  1..11
                        note = Synthetic: Alternative LC CDR1 antibody F19
source                  1..11
                        mol_type = protein
                        organism = synthetic construct
SEQUENCE: 19
RASQGVSSYL A                                                                  11

SEQ ID NO: 20           moltype = AA   length = 7
FEATURE                 Location/Qualifiers
REGION                  1..7
                        note = Synthetic: Alternative LC CDR2 antibody F19
source                  1..7
                        mol_type = protein
                        organism = synthetic construct
SEQUENCE: 20
DASNRAT                                                                        7

SEQ ID NO: 21           moltype = AA   length = 8
FEATURE                 Location/Qualifiers
REGION                  1..8
                        note = Synthetic: Alternative LC CDR3 antibody F19
source                  1..8
                        mol_type = protein
                        organism = synthetic construct
SEQUENCE: 21
QQRSNWHP                                                                       8

SEQ ID NO: 22           moltype = AA   length = 5
FEATURE                 Location/Qualifiers
REGION                  1..5
                        note = Synthetic: HC CDR1 antibody E1
source                  1..5
                        mol_type = protein
                        organism = synthetic construct
SEQUENCE: 22
RFNMN                                                                          5

SEQ ID NO: 23           moltype = AA   length = 17
```

```
FEATURE              Location/Qualifiers
REGION               1..17
                     note = Synthetic: HC CDR2 antibody E1
source               1..17
                     mol_type = protein
                     organism = synthetic construct
SEQUENCE: 23
YISSSSYTIY YADSVKG                                                        17

SEQ ID NO: 24        moltype = AA  length = 7
FEATURE              Location/Qualifiers
REGION               1..7
                     note = Synthetic: HC CDR3 antibody E1
source               1..7
                     mol_type = protein
                     organism = synthetic construct
SEQUENCE: 24
SIAAFDY                                                                    7

SEQ ID NO: 25        moltype = AA  length = 11
FEATURE              Location/Qualifiers
REGION               1..11
                     note = Synthetic: LC CDR1 antibody E1
source               1..11
                     mol_type = protein
                     organism = synthetic construct
SEQUENCE: 25
RASQGISSAL A                                                              11

SEQ ID NO: 26        moltype = AA  length = 7
FEATURE              Location/Qualifiers
REGION               1..7
                     note = Synthetic: LC CDR2 antibody E1
source               1..7
                     mol_type = protein
                     organism = synthetic construct
SEQUENCE: 26
DASSLES                                                                    7

SEQ ID NO: 27        moltype = AA  length = 8
FEATURE              Location/Qualifiers
REGION               1..8
                     note = Synthetic: LC CDR3 antibody E1
source               1..8
                     mol_type = protein
                     organism = synthetic construct
SEQUENCE: 27
QQFNSYRT                                                                   8

SEQ ID NO: 28        moltype = AA  length = 12
FEATURE              Location/Qualifiers
REGION               1..12
                     note = Synthetic: Alternative LC CDR1 antibody E1
source               1..12
                     mol_type = protein
                     organism = synthetic construct
SEQUENCE: 28
RASQSVSSSY LT                                                             12

SEQ ID NO: 29        moltype = AA  length = 7
FEATURE              Location/Qualifiers
REGION               1..7
                     note = Synthetic: Alternative LC CDR2 antibody E1
source               1..7
                     mol_type = protein
                     organism = synthetic construct
SEQUENCE: 29
GASSRAT                                                                    7

SEQ ID NO: 30        moltype = AA  length = 9
FEATURE              Location/Qualifiers
REGION               1..9
                     note = Synthetic: Alternative LC CDR3 antibody E1
source               1..9
                     mol_type = protein
                     organism = synthetic construct
SEQUENCE: 30
QQYGSSMYT                                                                  9
```

-continued

```
SEQ ID NO: 31          moltype = AA  length = 12
FEATURE                Location/Qualifiers
REGION                 1..12
                       note = Synthetic: Alternative LC CDR1 antibody E1
source                 1..12
                       mol_type = protein
                       organism = synthetic construct
SEQUENCE: 31
RASQSVSSSY LA                                                                 12

SEQ ID NO: 32          moltype = AA  length = 7
FEATURE                Location/Qualifiers
REGION                 1..7
                       note = Synthetic: Alternative LC CDR2 antibody E1
source                 1..7
                       mol_type = protein
                       organism = synthetic construct
SEQUENCE: 32
GASNRAT                                                                        7

SEQ ID NO: 33          moltype = AA  length = 9
FEATURE                Location/Qualifiers
REGION                 1..9
                       note = Synthetic: Alternative LC CDR3 antibody E1
source                 1..9
                       mol_type = protein
                       organism = synthetic construct
SEQUENCE: 33
QQYGSSPWT                                                                      9

SEQ ID NO: 34          moltype = AA  length = 5
FEATURE                Location/Qualifiers
REGION                 1..5
                       note = Synthetic: HC CDR1 antibody E13
source                 1..5
                       mol_type = protein
                       organism = synthetic construct
SEQUENCE: 34
NAWMS                                                                          5

SEQ ID NO: 35          moltype = AA  length = 19
FEATURE                Location/Qualifiers
REGION                 1..19
                       note = Synthetic: HC CDR2 antibody E13
source                 1..19
                       mol_type = protein
                       organism = synthetic construct
SEQUENCE: 35
RIKSKIDGGT TDYAAPVKG                                                          19

SEQ ID NO: 36          moltype = AA  length = 8
FEATURE                Location/Qualifiers
REGION                 1..8
                       note = Synthetic: HC CDR3 antibody E13
source                 1..8
                       mol_type = protein
                       organism = synthetic construct
SEQUENCE: 36
AMAGAFGF                                                                       8

SEQ ID NO: 37          moltype = AA  length = 12
FEATURE                Location/Qualifiers
REGION                 1..12
                       note = Synthetic: LC CDR1 antibody E13
source                 1..12
                       mol_type = protein
                       organism = synthetic construct
SEQUENCE: 37
RASQSVSSSY LA                                                                 12

SEQ ID NO: 38          moltype = AA  length = 7
FEATURE                Location/Qualifiers
REGION                 1..7
                       note = Synthetic: LC CDR2 antibody E13
source                 1..7
                       mol_type = protein
                       organism = synthetic construct
SEQUENCE: 38
GASSRAT                                                                        7
```

```
SEQ ID NO: 39              moltype = AA   length = 10
FEATURE                    Location/Qualifiers
REGION                     1..10
                           note = Synthetic: LC CDR3 antibody E13
source                     1..10
                           mol_type = protein
                           organism = synthetic construct
SEQUENCE: 39
QQYGSSPMYT                                                                 10

SEQ ID NO: 40              moltype = AA   length = 7
FEATURE                    Location/Qualifiers
REGION                     1..7
                           note = Synthetic: HC CDR1 antibody E63
source                     1..7
                           mol_type = protein
                           organism = synthetic construct
SEQUENCE: 40
SGGYYWS                                                                     7

SEQ ID NO: 41              moltype = AA   length = 16
FEATURE                    Location/Qualifiers
REGION                     1..16
                           note = Synthetic: HC CDR2 antibody E63
source                     1..16
                           mol_type = protein
                           organism = synthetic construct
SEQUENCE: 41
YIYYSGSTNY NPSLKS                                                          16

SEQ ID NO: 42              moltype = AA   length = 12
FEATURE                    Location/Qualifiers
REGION                     1..12
                           note = Synthetic: HC CDR3 antibody E63
source                     1..12
                           mol_type = protein
                           organism = synthetic construct
SEQUENCE: 42
WITMFRGVGF DP                                                              12

SEQ ID NO: 43              moltype = AA   length = 11
FEATURE                    Location/Qualifiers
REGION                     1..11
                           note = Synthetic: LC CDR1 antibody E63
source                     1..11
                           mol_type = protein
                           organism = synthetic construct
SEQUENCE: 43
RASQSIGSSL H                                                               11

SEQ ID NO: 44              moltype = AA   length = 7
FEATURE                    Location/Qualifiers
REGION                     1..7
                           note = Synthetic: LC CDR2 antibody E63
source                     1..7
                           mol_type = protein
                           organism = synthetic construct
SEQUENCE: 44
YASQSFS                                                                     7

SEQ ID NO: 45              moltype = AA   length = 9
FEATURE                    Location/Qualifiers
REGION                     1..9
                           note = Synthetic: LC CDR3 antibody E63
source                     1..9
                           mol_type = protein
                           organism = synthetic construct
SEQUENCE: 45
RQSSSLPLT                                                                   9

SEQ ID NO: 46              moltype = AA   length = 5
FEATURE                    Location/Qualifiers
REGION                     1..5
                           note = Synthetic: HC CDR1 antibody F23
source                     1..5
                           mol_type = protein
                           organism = synthetic construct
SEQUENCE: 46
```

```
GYYWN                                                                            5

SEQ ID NO: 47           moltype = AA  length = 11
FEATURE                 Location/Qualifiers
REGION                  1..11
                        note = Synthetic: HC CDR2 antibody F23
source                  1..11
                        mol_type = protein
                        organism = synthetic construct
SEQUENCE: 47
EINQYNPSLK S                                                                    11

SEQ ID NO: 48           moltype = AA  length = 14
FEATURE                 Location/Qualifiers
REGION                  1..14
                        note = Synthetic: HC CDR3 antibody F23
source                  1..14
                        mol_type = protein
                        organism = synthetic construct
SEQUENCE: 48
EIAIADKGYY GLDV                                                                 14

SEQ ID NO: 49           moltype = AA  length = 11
FEATURE                 Location/Qualifiers
REGION                  1..11
                        note = Synthetic: LC CDR1 antibody F23
source                  1..11
                        mol_type = protein
                        organism = synthetic construct
SEQUENCE: 49
RASQGISSAL A                                                                    11

SEQ ID NO: 50           moltype = AA  length = 7
FEATURE                 Location/Qualifiers
REGION                  1..7
                        note = Synthetic: LC CDR2 antibody F23
source                  1..7
                        mol_type = protein
                        organism = synthetic construct
SEQUENCE: 50
DASSLES                                                                          7

SEQ ID NO: 51           moltype = AA  length = 9
FEATURE                 Location/Qualifiers
REGION                  1..9
                        note = Synthetic: LC CDR3 antibody F23
source                  1..9
                        mol_type = protein
                        organism = synthetic construct
SEQUENCE: 51
QQFNSYPLT                                                                        9

SEQ ID NO: 52           moltype = AA  length = 5
FEATURE                 Location/Qualifiers
REGION                  1..5
                        note = Synthetic: HC CDR1
source                  1..5
                        mol_type = protein
                        organism = synthetic construct
SEQUENCE: 52
SYYIH                                                                            5

SEQ ID NO: 53           moltype = AA  length = 14
FEATURE                 Location/Qualifiers
REGION                  1..14
                        note = Synthetic: HC CDR2
source                  1..14
                        mol_type = protein
                        organism = synthetic construct
SEQUENCE: 53
PGSDITKYNE KFKG                                                                 14

SEQ ID NO: 54           moltype = AA  length = 10
FEATURE                 Location/Qualifiers
REGION                  1..10
                        note = Synthetic: HC CDR3
source                  1..10
                        mol_type = protein
                        organism = synthetic construct
```

```
SEQUENCE: 54
GISTYSAMDF                                                              10

SEQ ID NO: 55           moltype = AA  length = 11
FEATURE                 Location/Qualifiers
REGION                  1..11
                        note = Synthetic: LC CDR1
source                  1..11
                        mol_type = protein
                        organism = synthetic construct
SEQUENCE: 55
KASQDVGTAV A                                                            11

SEQ ID NO: 56           moltype = AA  length = 7
FEATURE                 Location/Qualifiers
REGION                  1..7
                        note = Synthetic: LC CDR2
source                  1..7
                        mol_type = protein
                        organism = synthetic construct
SEQUENCE: 56
WASTRHT                                                                 7

SEQ ID NO: 57           moltype = AA  length = 9
FEATURE                 Location/Qualifiers
REGION                  1..9
                        note = Synthetic: LC CDR3
source                  1..9
                        mol_type = protein
                        organism = synthetic construct
SEQUENCE: 57
QQYSSYPLT                                                               9

SEQ ID NO: 58           moltype = AA  length = 122
FEATURE                 Location/Qualifiers
REGION                  1..122
                        note = Synthetic: HC variable region
source                  1..122
                        mol_type = protein
                        organism = synthetic construct
SEQUENCE: 58
QVQLVQSGAE VKKPGASVKV SCKASGYTFT SYYIHWVRQA PGQRLEWMGW IFPGSDITKY        60
NEKFKGRVTI TRDTSASTAY MELSSLRSED TAVYYCARED YGISTYSAMD FWGQGTLVTV       120
SS                                                                     122

SEQ ID NO: 59           moltype = AA  length = 108
FEATURE                 Location/Qualifiers
REGION                  1..108
                        note = Synthetic: LC variable region
source                  1..108
                        mol_type = protein
                        organism = synthetic construct
SEQUENCE: 59
DIQLTQSPSF LSASVGDRVT ITCKASQDVG TAVAWYQQKP GKAPKLLIYW ASTRHTGVPS        60
RFSGSGSGTE FTLTISSLQP EDFATYYCQQ YSSYPLTFGQ GTKVEIKR                    108

SEQ ID NO: 60           moltype = AA  length = 5
FEATURE                 Location/Qualifiers
REGION                  1..5
                        note = Synthetic: HC CDR1 of 18E04
source                  1..5
                        mol_type = protein
                        organism = synthetic construct
SEQUENCE: 60
HFDIN                                                                   5

SEQ ID NO: 61           moltype = AA  length = 17
FEATURE                 Location/Qualifiers
REGION                  1..17
                        note = Synthetic: HC CDR2 of 18E04
source                  1..17
                        mol_type = protein
                        organism = synthetic construct
SEQUENCE: 61
WMNPDSDNTD YAQEFQG                                                      17

SEQ ID NO: 62           moltype = AA  length = 7
FEATURE                 Location/Qualifiers
REGION                  1..7
```

```
                                    note = Synthetic: HC CDR3 of 18E04
source                              1..7
                                    mol_type = protein
                                    organism = synthetic construct
SEQUENCE: 62
GGTTLDY                                                                          7

SEQ ID NO: 63                       moltype = AA  length = 11
FEATURE                             Location/Qualifiers
REGION                              1..11
                                    note = Synthetic: LC CDR1 of 18E04
source                              1..11
                                    mol_type = protein
                                    organism = synthetic construct
SEQUENCE: 63
SGDALPKKYA Y                                                                    11

SEQ ID NO: 64                       moltype = AA  length = 7
FEATURE                             Location/Qualifiers
REGION                              1..7
                                    note = Synthetic: LC CDR2 of 18E04
source                              1..7
                                    mol_type = protein
                                    organism = synthetic construct
SEQUENCE: 64
EDSKRPS                                                                          7

SEQ ID NO: 65                       moltype = AA  length = 11
FEATURE                             Location/Qualifiers
REGION                              1..11
                                    note = Synthetic: LC CDR3 of 18E04
source                              1..11
                                    mol_type = protein
                                    organism = synthetic construct
SEQUENCE: 65
YSTDSSDNHV I                                                                    11

SEQ ID NO: 66                       moltype = AA  length = 5
FEATURE                             Location/Qualifiers
REGION                              1..5
                                    note = Synthetic: HC CDR1 of 98C07
source                              1..5
                                    mol_type = protein
                                    organism = synthetic construct
SEQUENCE: 66
DYYMS                                                                            5

SEQ ID NO: 67                       moltype = AA  length = 16
FEATURE                             Location/Qualifiers
REGION                              1..16
                                    note = Synthetic: HC CDR2 of 98C07
source                              1..16
                                    mol_type = protein
                                    organism = synthetic construct
SEQUENCE: 67
YISRSSFIYY SESVKG                                                               16

SEQ ID NO: 68                       moltype = AA  length = 8
FEATURE                             Location/Qualifiers
REGION                              1..8
                                    note = Synthetic: HC CDR3 of 98C07
source                              1..8
                                    mol_type = protein
                                    organism = synthetic construct
SEQUENCE: 68
WELSPFDY                                                                         8

SEQ ID NO: 69                       moltype = AA  length = 11
FEATURE                             Location/Qualifiers
REGION                              1..11
                                    note = Synthetic: LC CDR1 of 98C07
source                              1..11
                                    mol_type = protein
                                    organism = synthetic construct
SEQUENCE: 69
RASQGISNYL A                                                                    11

SEQ ID NO: 70                       moltype = AA  length = 7
FEATURE                             Location/Qualifiers
```

```
REGION                  1..7
                        note = Synthetic: LC CDR2 of 98C07
source                  1..7
                        mol_type = protein
                        organism = synthetic construct
SEQUENCE: 70
AASSLQS                                                                 7

SEQ ID NO: 71           moltype = AA   length = 9
FEATURE                 Location/Qualifiers
REGION                  1..9
                        note = Synthetic: LC CDR3 of 98C07
source                  1..9
                        mol_type = protein
                        organism = synthetic construct
SEQUENCE: 71
QQYNTYPFT                                                               9

SEQ ID NO: 72           moltype = AA   length = 5
FEATURE                 Location/Qualifiers
REGION                  1..5
                        note = Synthetic: HC CDR1 of 1C02
source                  1..5
                        mol_type = protein
                        organism = synthetic construct
SEQUENCE: 72
YYGIS                                                                   5

SEQ ID NO: 73           moltype = AA   length = 17
FEATURE                 Location/Qualifiers
REGION                  1..17
                        note = Synthetic: HC CDR2 of 1C02
source                  1..17
                        mol_type = protein
                        organism = synthetic construct
SEQUENCE: 73
WISANSGNTN YAQKFQG                                                      17

SEQ ID NO: 74           moltype = AA   length = 8
FEATURE                 Location/Qualifiers
REGION                  1..8
                        note = Synthetic: HC CDR3 of 1C02
source                  1..8
                        mol_type = protein
                        organism = synthetic construct
SEQUENCE: 74
GGVAVLEY                                                                8

SEQ ID NO: 75           moltype = AA   length = 11
FEATURE                 Location/Qualifiers
REGION                  1..11
                        note = Synthetic: LC CDR1 of 1C02
source                  1..11
                        mol_type = protein
                        organism = synthetic construct
SEQUENCE: 75
WASQGISSYL A                                                            11

SEQ ID NO: 76           moltype = AA   length = 7
FEATURE                 Location/Qualifiers
REGION                  1..7
                        note = Synthetic: LC CDR2 of 1C02
source                  1..7
                        mol_type = protein
                        organism = synthetic construct
SEQUENCE: 76
VASTLQS                                                                 7

SEQ ID NO: 77           moltype = AA   length = 9
FEATURE                 Location/Qualifiers
REGION                  1..9
                        note = Synthetic: LC CDR3 of 1C02
source                  1..9
                        mol_type = protein
                        organism = synthetic construct
SEQUENCE: 77
QQLKIYPLT                                                               9

SEQ ID NO: 78           moltype = AA   length = 5
```

```
                    -continued
FEATURE             Location/Qualifiers
REGION              1..5
                    note = Synthetic: HC CDR1 of 1C06
source              1..5
                    mol_type = protein
                    organism = synthetic construct
SEQUENCE: 78
DYYMN                                                          5

SEQ ID NO: 79       moltype = AA  length = 17
FEATURE             Location/Qualifiers
REGION              1..17
                    note = Synthetic: HC CDR2 of 1C06
source              1..17
                    mol_type = protein
                    organism = synthetic construct
SEQUENCE: 79
DISSRDNTIY YADSVKG                                             17

SEQ ID NO: 80       moltype = AA  length = 14
FEATURE             Location/Qualifiers
REGION              1..14
                    note = Synthetic: HC CDR3 of 1C06
source              1..14
                    mol_type = protein
                    organism = synthetic construct
SEQUENCE: 80
ARERGFGDYF GMDV                                                14

SEQ ID NO: 81       moltype = AA  length = 11
FEATURE             Location/Qualifiers
REGION              1..11
                    note = Synthetic: LC CDR1 of 1C06
source              1..11
                    mol_type = protein
                    organism = synthetic construct
SEQUENCE: 81
RASQDISSAL A                                                   11

SEQ ID NO: 82       moltype = AA  length = 7
FEATURE             Location/Qualifiers
REGION              1..7
                    note = Synthetic: LC CDR2 of 1C06
source              1..7
                    mol_type = protein
                    organism = synthetic construct
SEQUENCE: 82
DASSLES                                                        7

SEQ ID NO: 83       moltype = AA  length = 9
FEATURE             Location/Qualifiers
REGION              1..9
                    note = Synthetic: LC CDR3 of 1C06
source              1..9
                    mol_type = protein
                    organism = synthetic construct
SEQUENCE: 83
QQFNTYPLT                                                      9
```

What is claimed is:

1. A method of treating pneumonia associated with COVID-19 comprising administering to a human subject in need thereof an effective amount of an anti-LIGHT antibody comprising a heavy chain and a light chain variable region comprising a CDR-H1 having the sequence of SEQ ID NO: 2, CDR-H2 having the sequence of SEQ ID NO: 3, CDR-H3 having the sequence of SEQ ID NO: 4, CDR-L1 having the sequence of SEQ ID NO: 5, CDR-L2 having the sequence of SEQ ID NO: 6, and CDR-L3 having the sequence of SEQ ID NO: 7.

2. The method of claim 1, wherein administration of the anti-LIGHT antibody reduces serum free-LIGHT levels in the subject.

3. The method of claim 1, wherein a single dose of about 16 mg/kg of the anti-LIGHT antibody is administered.

4. The method of claim 1, wherein the subject has received, or is currently receiving, an anti-COVID-19 therapy comprising a corticosteroid and/or remdesivir.

5. The method of claim 1, wherein administration of the anti-LIGHT antibody reduces the subject's risk of mortality by equal to or greater than 50% at 28 days and/or 60 days after administration.

6. The method of claim 1, where the subject is 60 years of age or older.

7. The method of claim 1, wherein administration of the anti-LIGHT antibody reduces the subject's risk of respiratory failure.

8. A method of treating respiratory failure associated with COVID-19 pneumonia comprising administering to a human subject in need thereof an effective amount of an anti-LIGHT antibody comprising a heavy chain and a light chain variable region comprising a CDR-H1 having the sequence of SEQ ID NO: 2, CDR-H2 having the sequence of SEQ ID NO: 3, CDR-H3 having the sequence of SEQ ID NO: 4, CDR-L1 having the sequence of SEQ ID NO: 5, CDR-L2 having the sequence of SEQ ID NO: 6, and CDR-L3 having the sequence of SEQ ID NO: 7.

\* \* \* \* \*